United States Patent
Picking et al.

(10) Patent No.: US 11,464,843 B2
(45) Date of Patent: Oct. 11, 2022

(54) USE OF THE SALMONELLA SPP TYPE III SECRETION PROTEINS AS A PROTECTIVE VACCINATION

(71) Applicants: The Board of Regents for Oklahoma State University, Stillwater, OK (US); University of Kansas, Lawrence, KS (US)

(72) Inventors: Wendy L. Picking, Lawrence, KS (US); William D. Picking, Lawrence, KS (US)

(73) Assignees: The Board of Regents for Oklahoma State University, Stillwater, OK (US); University of Kansas, Lawrence, KS (US)

( * ) Notice: Subject to any disclaimer, the term of this patent is extended or adjusted under 35 U.S.C. 154(b) by 0 days.

(21) Appl. No.: 16/752,802

(22) Filed: Jan. 27, 2020

(65) Prior Publication Data
US 2020/0306355 A1    Oct. 1, 2020

Related U.S. Application Data

(63) Continuation of application No. 15/950,735, filed on Apr. 11, 2018, now Pat. No. 10,548,962, which is a continuation-in-part of application No. 15/013,454, filed on Feb. 2, 2016, now Pat. No. 9,950,053, which is a continuation-in-part of application No. 14/437,535, filed as application No. PCT/US2013/066105 on Oct. 22, 2013, now abandoned.

(60) Provisional application No. 61/716,911, filed on Oct. 22, 2012.

(51) Int. Cl.
C07K 14/255    (2006.01)
A61K 39/112    (2006.01)
A61K 39/00     (2006.01)

(52) U.S. Cl.
CPC .... *A61K 39/0275* (2013.01); *A61K 2039/543* (2013.01); *A61K 2039/552* (2013.01); *A61K 2039/55505* (2013.01); *A61K 2039/55544* (2013.01); *A61K 2039/55572* (2013.01); *A61K 2039/70* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,982,538 A | 1/1991 | Horstketter |
| 5,034,506 A | 7/1991 | Summerton et al. |
| 5,138,045 A | 8/1992 | Cook et al. |
| 5,168,062 A | 12/1992 | Stinski |
| 5,218,105 A | 6/1993 | Cook et al. |
| 5,258,498 A | 11/1993 | Huston et al. |
| 5,283,187 A | 2/1994 | Aebischer et al. |
| 5,385,839 A | 1/1995 | Stinski |
| 5,459,255 A | 10/1995 | Cook et al. |
| 6,083,486 A | 7/2000 | Weissleder et al. |
| 7,094,410 B2 | 8/2006 | Reisfeld et al. |
| 7,927,870 B2 | 4/2011 | Volkin et al. |
| 8,039,007 B2 | 10/2011 | Rappuoli et al. |
| 9,950,053 B2 | 4/2018 | Picking et al. |
| 10,548,962 B2 | 2/2020 | Picking et al. |
| 2004/0009191 A1 | 1/2004 | Lowery et al. |
| 2008/0260776 A1 | 10/2008 | Bumann et al. |
| 2013/0149329 A1 | 6/2013 | Picking et al. |
| 2016/0220655 A1 | 8/2016 | Picking et al. |

FOREIGN PATENT DOCUMENTS

| | | | |
|---|---|---|---|
| WO | WO9522618 | 8/1995 | |
| WO | WO199718225 | 5/1997 | |
| WO | WO200059537 | 10/2000 | |
| WO | WO2002088346 | 11/2002 | |
| WO | WO-2005116062 A1 * | 12/2005 | ........... C07K 14/245 |

OTHER PUBLICATIONS

Felgner, P. et al, "Lipofection: a highly efficient, lipid-mediated DNA-transfection procedure", Proc. Natl. Acad. Sci., USA, vol. 84, pp. 7413-7417, (Nov. 1987).
Malone, R. et al, "Cationic liposome-mediated RNA transfection", Proc. Natl. Acad. Sci., USA, vol. 86, pp. 6077-6081, (Aug. 1989).
Leventis, R. et al, "Interactions of mammalian cells with lipid dispersions containing novel metabolizable cationic amphiphiles", Biochim. Biophys. Acta, vol. 1023(1), pp. 124-132, (Mar. 1990).
Behr, J. et al, "Efficient gene transfer into mammalian primary endocrine cells with lipopolyamine-coated DNA", Proc. Natl. Acad. Sci., USA, vol. 86, pp. 6982-6986, (Sep. 1989).
Medina, E. et al, "Pathogenicity island 2 mutants of salmonella typhimurium are efficient carriers for heterologous antigens and enable modulation of immune responses", Infection and Immunity, vol. 67(3), pp. 1093-1099, Mar. 1, 1999).
Oberhauser, B. et al, "Effective incorporation of 2'-O-methyl-oligoribonucleotides into liposomes and enhanced cell association through modification and thiocholesterol", Nucl. Acids Res, vol. 20(3), pp. 533-538, (1992).
Kabanov, A. et al, "A new class of antivirals: antisense oligonucleotides combined with a hydrophobic substituent effectively inhibit virus reproduction and synthesis of virus-specific proteins in MDCK cells", FEBS Lett, vol. 259(2), pp. 327-330, (Jan. 1990).
O'Garra, A., "Cytokines induce the development of functionally heterogeneous T helper cell subsets", Immunity, vol. 8, pp. 275-283, (Mar. 1998).

(Continued)

*Primary Examiner* — Gary B Nickol
*Assistant Examiner* — Lakia J Jackson-Tongue
(74) *Attorney, Agent, or Firm* — Meunier Carlin & Curfman LLC

(57) ABSTRACT

Antigenic molecules and compositions described herein protect against infection by typhoidal and non-typhoidal *Salmonella* serovars. Methods of immunization comprise the use of the antigenic molecules.

2 Claims, 19 Drawing Sheets

Specification includes a Sequence Listing.

(56) References Cited

OTHER PUBLICATIONS

Saison-Behmoaras, T. et al, "Short modified antisense olionucleotides directed against Ha-ras point mutation induce selective cleavage of the nMRA and inhibit T24 cells proliferation", EMBO J., vol. 10(5), pp. 1111-1118, (May 1991).
Pollard, H. et al, "Polyethylenimine but not cationic lipids promotes transgene delivery to the nucleus in mammalian cells", J. Biol. Chem., vol. 273(13), pp. 7507-7511, (Mar. 1998).
Krumlauf, R. et al, "Developmental regulation of alpha-fetoprotein genes in transgenic mice", Mol. Cell. Biol., vol. 5 (7), pp. 1639-1648, (Jul. 1985).
Letsinger, R., "Cholesteryl-conjugated oligonucleotides: synthesis, properties, and activity as inhibitors of replication of human immunodeficiency virus in cell cultures", Proc. Natl. Acad. Sci., USA, vol. 86, pp. 6553-6556, (Sep. 1989).
Shea, R. et al, "Snythesis, hybridization properties and antiviral activity of lipid-oligodeoxynucleotide conjugates", Nucl. Acids Res., vol. 18(13), pp. 3777-3783, (Jun. 1990).
Oppenheim, J. et al, "Prospects for Cytokine and chemokine biotherapy", Clin. Cancer Res., vol. 12(3), pp. 2682-2686, (Dec. 1997).
Henikoff, S. et al, "Amino acid substitution matrices from protein blocks", Proc. Natl. Acad. Sci., USA, vol. 89, pp. 10915-10919, (Nov. 1992).
Chen, Y. et al, "Expression of ssDNA in mammalian cells", BioTechniques, vol. 34(1), pp. 161-171, (Jan. 2003).
Curiel, D. et al, "Adenovirus enhancement of transferrin-polylysine-mediated gene delivery", PNAS, vol. 88(19), pp. 8850-8854, (Oct. 1991).
Geller, A. et al, "An HSV-1 vector expressing tyrosine hydroxylase causes production and release of I-DPOA from cultured rat striatal cells", J. Neurochem., vol. 64(2), pp. 487-496, (Feb. 1995).
Alexander, W. et al, "Expression of the c-myc oncogene under control of an immunoglobulin enhancer in Eu-myc transgenic mice", Mol. Cell. Biol., vol. 7, pp. 1436-14-44, (Apr. 1987).
Geller, A. et al, "Infection of cultured central nervous system neurons with a defective herpes simplex virus 1 vector results in stable expression of *Escherichia coli* beta-galactosidase", Proc. Natl. Acad. Sci, USA, vol. 87(3), pp. 1149-1153, (Feb. 1990).
Geller, A. et al, "Long-term increases in neurotransmitter release from neuronal cells expressing a constitutively active adenylate cyclase from a herpes simplex virus type 1 vector", Proc. Natl. Acad. Sci., USA, vol. 90(16), pp. 7603-7607, (1993).
Birket, S. et al, "Preparation and characterization of translocator/chaperone complexes and their component proteins from shigella flexneri", Biochemistry, vol. 46(27), pp. 8128-8137, (Jun. 2007).
Ito, A. et al, "Synthetic Cationic Amphiphiles for liposome-mediated DNA transfection", Biochem. Intl., vol. 22(2), pp. 235-241, (Oct. 1990).
Yang, Y. et al, "Cellular and humoral immune responses to viral antigens create barriers to lung-directed gene therapy with recombinant adenoviruses", J. Virol., vol. 69(4), pp. 2004-2015, (Apr. 1995).
Kaplitt, M. et al, "Long-term gene expression and phenotypic correction using adeno-associated virus vectors in the mammalian brain", Nat Genet., vol. 8(2), pp. 148-154, (Oct. 1994).
Davis, H, et al, "Direct gene transfer into skeletal muscle in vivo: factors affecting efficiency of transfer and stability of expression", Hum Gene Ther, vol. 4(2), pp. 151-159, (1993).
Sambrook, D. et al, "Molecular cloning: a laboratory manual", Cold Spring Harbor Laboratory Press, (1989).
Chen, X. et al, "Impact of detergent on biophysical properties and immune response of the IpaDB fusion protein, a candidate subunit vaccine against Shigella species", Infect. Immunol., 83:1:292-299, (2015).
Felgner, P. et al, "Cationic liposome-mediated transfection", Bethesda Res. Lab. Focus, vol. 11, pp. 21-25, (1989).
Pinkert, C. et al, "An albumin enhancer located 10 kb upstream functions along with its promoter to direct efficient, liver-specific expression in transgenic mice", Genes and Devel., vol. 1, pp. 268-276, (1987).
Quantin, B. et al, "Adenovirus as an expression vector in muscle cells in vivo", Proc. Natl. Acad. Sci., USA, vol. 89, pp. 2581-2584, (1992).
Stratford-Perricadet, L. et al, "Widespread long-term gene transfer to mouse skeletal muscles and heart", J. Clin. Invest., vol. 90, pp. 626-630, (Aug. 1992).
Choudhari, S. et al, "Studies of the conformational stability of invasion plasmid antigen B from Shigella", Protein Society., vol. 22(5), pp. 666-670, (2013).
Choudhari, S. et al, "Biophysical characterization of the type III secretion tip proteins and the tip proteins attached to bacterium-like particles", J. Pharm. Sci., doi: 10.1002/jps.24047, (Jun. 2014).
Martinez-Becerra, F. et al, "Parenteral immunization with IpaB/IpaD protects mice against lethal pulmonary infection by Shigella", Vaccine, 31(24), pp. 2667-2672, (2013b).
Wagner, M. et al, "Nucleotide sequence of the thymidine kinase gene of herpes simplex virus type 1", Proc. Natl. Acad. Sci., USA, vol. 78(3), pp. 1441-1445, (Mar. 1981).
Mosmann, T. et al, "The expanding universe of T-cell subsets: Th1, Th2 and more", Immunol. Today, vol. 17(3), pp. 138-146 , (1996).
Villa-Komaroff, L. et al, "A bacterial clone synthesizing proinsulin", Proc. Natl. Acad. Sci., USA, vol. 75(8), pp. 3727-3731, (Aug. 1978).
Deboer, H. et al, "The tac promoter: a functional hybrid derived from the trp and lac promoters", Proc. Natl. Acad. Sci., USA, vol. 80, pp. 21-25, (Jan. 1983).
Swift, G. et al, "Tissue-specific expression of the rate pancreatic elastase I gene in transgenic mice", Cell, vol. 38, pp. 639-646, (Oct. 1984).
Abbas, A. et al, "Functional diversity of helper T lymphocytes", Nature, vol. 383, p. 787-793, (Oct. 1996).
Shani, M. et al, "Tissue-specific and developmentally regulated expression of a Chimeric actin-globin gene in transgenic mice", Molecular and Cellular Biology, vol. 6(7), pp. 2624-2631, (Jul. 1986).
Banchereau, J. et al, "Dentritic cells and the control of immunity", Nature, vol. 392, p. 245-252, (Mar. 1988).
Gebeyehu, G. et al, "Novel biotinylated nucleotide—analogs for labeling and colorrmetric detection of DNA", Nucleic Acids Research, vol. 15(11), pp. 4513-4534, (1987).
Mason, A. et al, "The hypogonadal mouse: reproductive functions restored by gene therapy", Science, vol. 234, No. 4782, pp. 1372-1378, (Dec. 1986).
Wigler, M. et al, "Transfer of purified herpes virus thymidine kinase gene to cultured mouse cells", Cell, vol. 11, No. 1, pp. 223-232, (1977).
Kelsey, G. et al, "Species- and tissue-specific expression of human alpha1-antitrypsin in transgenic mice", Genes and Devel., vol. 1, pp. 161-171, (1987).
S-J Lee et al, "Identification of a common immune signature in murine and human systemic Salmonellosis", PNAS, vol. 109(13), pp. 4998-5003 (Mar. 27, 2012).
Nielsen, P. et al, "Sequence-selective recognition of DNA by strand displacement with a thymine-substituted polyamide", Science, vol. 254, pp. 1497-1500, (Dec. 1991).
Letsinger, R. et al, "Cholersteryl-conjugated oligonucleotides: Synthesis, properties, and activity as inhibitors of replication of human immunodeficiency virus in cell culture", Proc. Natl. Acad. Sci. USA, vol. 86, pp. 6553-6556, (Sep. 1989).

\* cited by examiner

Figures 10A-B
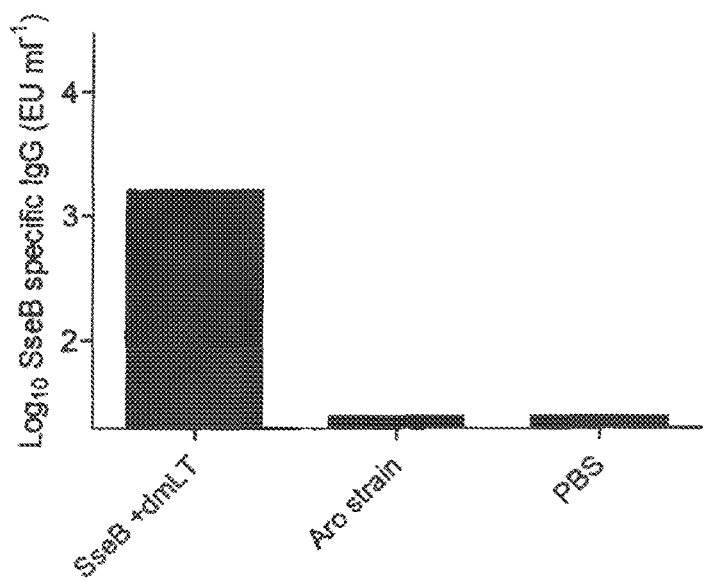
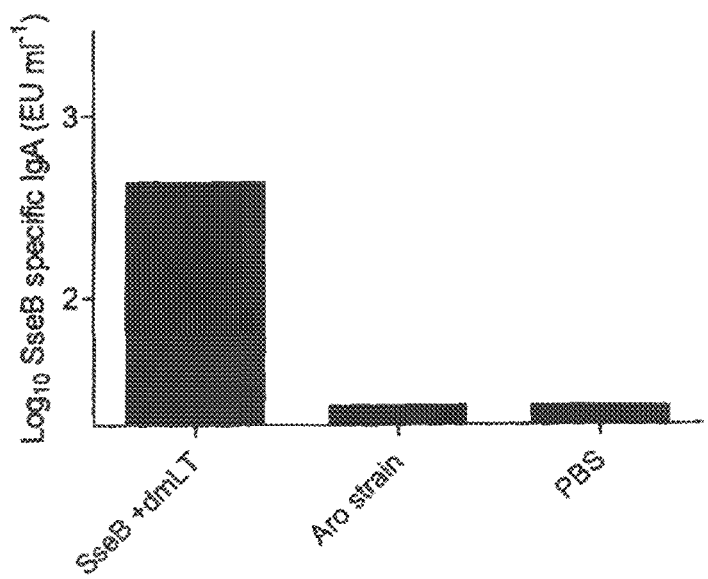

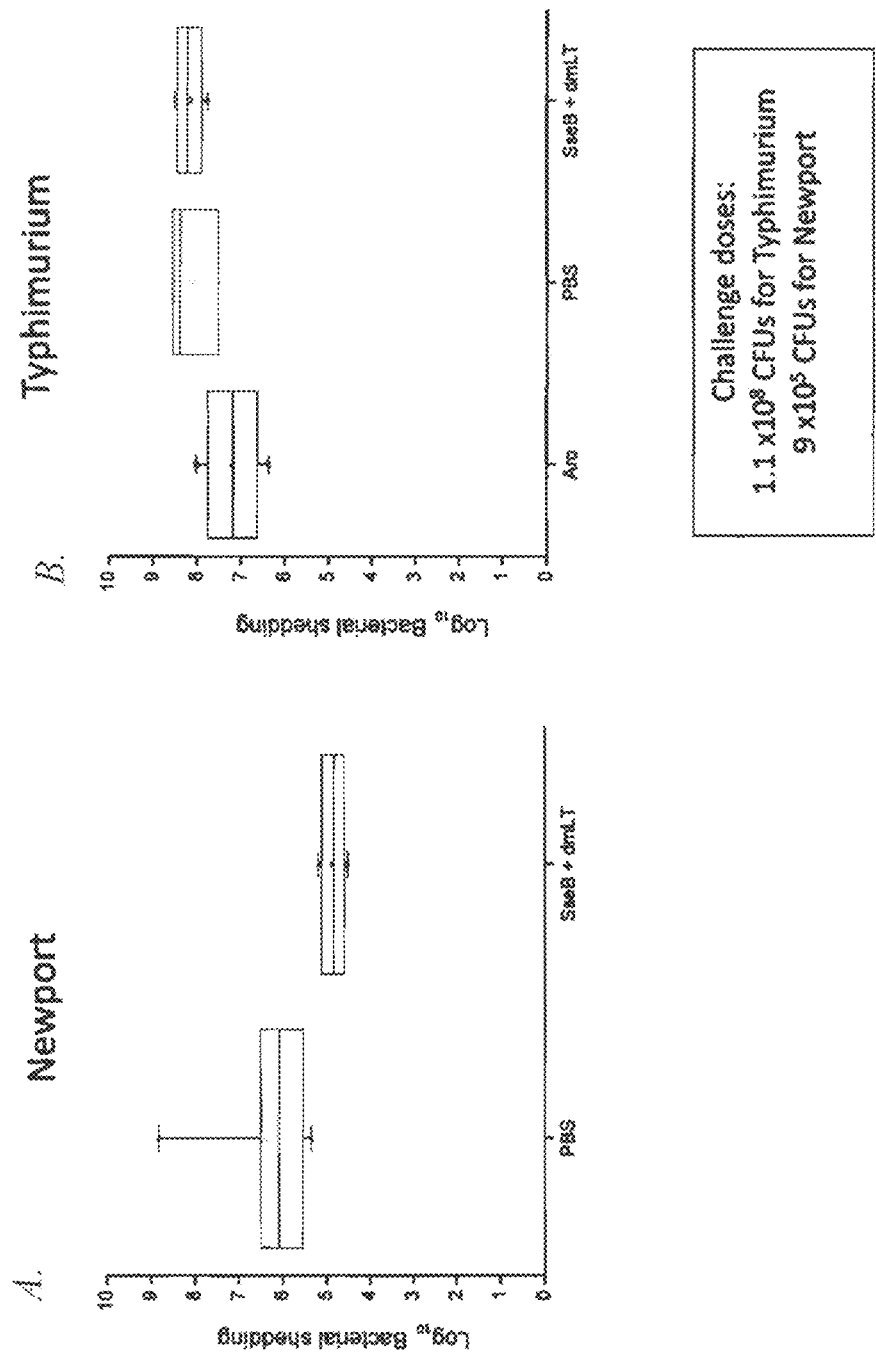
Figures 11A-B

*A.* MVNDASSISRSGYTQNPRLAEAAFEGVRKNTDFLKAADKAFKDVVATKAGDLKAGTKS
GESAINTVGLKPPTDAAREKLSSEGQLTLLLGKLMTLLGDVSLSQLESRLAVWQAMIES
QKEMGIQVSKEFQTALGEAQEATDLYEASIKKTDTAKSVYDAATKKLTQAQNKLQSLDP
ADPGYAQAEAAVEQAGKEATEAKEALDKATDATVKAGTDAKAKAEKADNILTKFQGTA
NAASQNQVSQGEQDNLSNVARLTMLMAMFIEIVGKNTEESLQNDLALFNALQEGRQAE
MEKKSAEFQEETRKAEETNRIMGCIGKVLGALLTIVSVVAAVFTGGASLALAAVGLAVM
VADEIVKAATGVSFIQQALNPIMEHVLKPLMELIGKAITKALEGLGVDKKTAEMAGSIVGA
IVAAIAMVAVIVVVAVVGKGAAAKLGNALSKMMGETIKKLVPNVLKQLAQNGSKLFTQG
MQRITSGLGNVGSKMGLQTNALSKELVGNTLNKVALGMEVTNTAAQSAGGVAEGVFIK
NASEALADFMLARFAMDQIQQWLKQSVEIFGENQKVTAELQKAMSSAVQQNADASRFI
LRQSRA (SEQ ID NO: 1)

*B.* ttatgcgcgactctggcgcagaataaaaacgcgaagcatccgcattttgctgtaccgcagaagacatggcttttgcagttccg
ccgttaccttctggttttcaccaaatattctacggattgtttaagccactgctgaatctgatccatggcaaaaacgggcgagcat
aaaatcagcaagcgcctcgctggcatttttaataaatacgccctcggcaacaccaccggctgactgggctgcggtattcgtg
actlccatgcccaacgccactttattlagggtattacctaccagctctttacttaaggcattcgtttgcaggcccatcttgctaccc
acattacccagaccgctagtaatacgttgcatcccctgggtaaagagtttgctgccgtttgcgccaactgtttcagcacgtta
ggcaccaacttcttaatcgttlcgcccatcattttgctcagcgcgttacccagtttcgccgccgcgcctttcccgacaactgcga
ccaccacaatgaccgccaccatggcaatagcggcgacaatcgcaccaacaatgctgccggccatctctgccgttttcttat
cgacgcctaatccttccagcgctttggtaatcgccttgccaatcagctccattaacggcttcagcacatgctccataatcgggt
ttagcgcctgctgaataaaacgacactcccgtcgccgcctlcacaatticatcggccaccattaccgcaagtcccaccgcag
ccagcgccagactcgccccaccggtaaaaacagcggccacaacgctgacaatggttagcagcgcgccgaggactttcc
cgatacatcccataatgcggttcgtttcctcggctttgcgcgtctcttctggaattcagccgatttctttccatctccgcctgacg
cccttcctgcaaggcgttgaaaagcgcaagatcgtttttgcaggcttcttccgtattttgcccacaatctcaataaacatggcc
atgagcatagtgaggcgggcgacatttgacagattatcctgctcaccctgggaaacctgattctgagaggcggcattagcc
gttcctggaatttggtcagaatgttatccgctttctcggctttgctttggcgtctgtgcctgctttaaccgtcgcatccgtggctt
atctaaggcctctttcgcctctgtcgcttctttccggcctgttctaccgcgcgcttcagcttgtgcatagccgggtcagccgggtc
cagcgattgcaatttattttgcgcctgcgtcagttttttggtcgcagcgtcataaacactcttggcgggtatccgtcttttgatactgg
cttcatagagatccgtcgcctcctgagcctctcccagagccgtctggaattcttcgataccctgaatcccatctctttttgtgact
caatcatgcctgccataccgccagacgagactccagttgagacagcgaaacatcgcccagtagggtcattaacttgcca
agcagtaatgtcaattgccctlcgctggagagttttccgggcggcgtccgtaggcggcttagacccaccgtattaatagc
gctctcgccggactttgttccggcttaaggtcgcccgctttcgttgccaccacatctttaaaagcttatccgccgctttaaaaa
gtccgtgttcttacgaacgccttcaaaaagccgcctcagcgaggcgcggattttgggtatatccgctacggctaatgctacttgc
gtcatttaccat (SEQ ID NO: 2)

*Figures 12A-B*

C. MLNIQNYSASPHPGIVAERPQTPSASEHAEIAVVPSTTEHRGTDIISLSQAATKIQQAQQ
TLQSTPPISEENNDERTLARQQLTSSLNALAKSGVSLSAEQNENLRSTFSARRRPYLAL
RLWPARTTISDAEIWDMVSQNISAIGDSYLGVYENVVAVYTDFYQAFSDILSKMGGWLS
PGKDGNTIKLNVDSLKSEISSLINKYTQINKNTILFPSQTGSGMTTATKAEAEQWIKELNL
PDSCLKASGSGYVVLVDTGPLSKMVSDLNGIGSGSALELDNAKYQAWQSGFKAQEEN
LKTTLQTLTQKYSNANSLYDNLVKVLSSTISSSLETAKSFLQG (SEQ ID NO: 3)

D. atgcttaatattcaaaattattcgcttctcctcatccggggatcgttgccgaacggccgcagactccttcggcgagcgagca
cgccgagattgccgtggtaccgtctaccacagaacatcgcggcacagatatcattcattatcgcaggcggctactaaaatc
cagcaggcacagcagacgctgcagtcaacgccacgatttctgaagagaataatgacgagcgcacgctggcgcgcca
acagtgaccagcagcctgaatgcgctggcgaagtccggcgtgtcattatccgcagaacaaaatgagaacctgcggagc
acgtttctgcgcgacgtcggcctatttagcgcttcgcctatggccagcgagaacaaccattctgatgctgagattgggata
tggtttccaaaatatatcggcgataggtgacagctacctggcgtttatgaaaacgttgtcgcagtctataccgatttttatca
ggccttcagtgatattctttccaaaatggggaggctggttatcgcctggtaaggatgcaaataccattaagctaaatgttgactc
acttaaaagtgaaataagtagtttaattaataaatacactcaaataaataaaaatacgattttatttccctcgcaaactggcag
cggaatgacaacagcaacgaaagcggaagctgagcagtggattaaagaattgaatttaccggacagctgtcaaaggc
gtctggttctggttatgtcgtactggtggatacggggccactgagcaaaatggttagcgatcttaatggaataggatcgggttc
agcccttgaactggataacgccaaatatcaagcctggcagtcgggttttaaagcacaggaagaaaaatctgaaaaccaca
ttacagacgctgacgcaaaaatatagcaatgccaattcattgtacgacaacctggtaaaagtgctgagcagtacgataagt
agcagcctggaaacgccaaaagcttcctgcaaggataa (SEQ ID NO: 4)

E. MSSGNILWGSQNPIVFKNSFGVSNADTGSQDDLSQQNPFAEGYGVLLILLMVIQAIANN
KFIEVQKNAERARNTQEKSNEMDEVIAKAAKGDAKTKEEVPEDVIKYMRDNGILIDGMTI
DDYMAKYGDHGKLDKGGLQAIKAALDNDANRNTDLMSQGQITIQKMSQELNAVLTQLT
GLISKWGEISSMIAQKTYS (SEQ ID NO: 5)

F. atgtcttcaggaaacatctatggggaagtcaaaaccctattgtgtttaaaaatagcttcggcgtcagcaacgctgataccgg
gagccaggatgacttatcccagcaaaatccgtttgccgaagggtatggtgtttgcttattctccttatggttattcaggctatcgc
aaataataaattattgaagtccagaagaacgctgaacgtgccagaaatacccaggaaaagtcaaatgagatggatgag
gtgattgctaaagcagccaaaggggatgctaaaaccaaagaggaggtgcctgaggatgtaattaaatacatgcgtgata
atggtattctcatcgatggtatgaccattgatgattatatggctaaatatgcgatcatgggaagctggataaaggtggcctac
aggcgatcaaagcggcttggataatgacgccaaccggaataccgatcttatgagtcaggggcagataacaattcaaaa
aatgtctcaggagcttaacgctgtccttacccaactgacagggcttatcagtaagtgggggaaatttccagtatgatagcg
cagaaaacgtactcatga (SEQ ID NO: 6)

*Figures 12C-F*

MLNIQNYSASPHPGIVAERPQTPSASEHAEIAVVPSTTEHRGTDIISLSQAATKIQQAQQ
TLQSTPPISEENNDERTLARQQLTSSLNALAKSGVSLSAEQNENLRSTFSARRRPYLAL
RLWPARTTISDAEIWDMVSQNISAIGDSYLGVYENVVAVYTDFYQAFSDILSKMGGWLS
PGKDGNTIKLNVDSLKSEISSLINKYTQINKNTILFPSQTGSGMTTATKAEAEQWIKELNL
PDSCLKASGSGYVVLVDTGPLSKMVSDLNGIGSGSALELDNAKYQAWQSGFKAQEEN
LKTTLQTLTQKYSNANSLYDNLVKVLSSTISSSLETAKSFLQGVDMVNDASSISRSGYTQ
NPRLAEAAFEGVRKNTDFLKAADKAFKDVVATKAGDLKAGTKSGESAINTVGLKPPTDA
AREKLSSEGQLTLLLGKLMTLLGDVSLSQLESRLAVWQAMIESQKEMGIQVSKEFQTAL
GEAQEATDLYEASIKKTDTAKSVYDAATKKLTQAQNKLQSLDPADPGYAQAEAAVEQA
GKEATEAKEALDKATDATVKAGTDAKAKAEKADNILTKFQGTANAASQNQVSQGEQDN
LSNVARLTMLMAMFIEIVGKNTEESLQNDLALFNALQEGRQAEMEKKSAEFQEETRKAE
ETNRIMGCIGKVLGALLTIVSVVAAVFTGGASLALAAVGLAVMVADEIVKAATGVSFIQQ
ALNPIMEHVLKPLMELIGKAITKALEGLGVDKKTAEMAGSIVGAIVAAIAMVAVIVVVAVV
GKGAAAKLGNALSKMMGETIKKLVPNVLKQLAQNGSKLFTQGMQRITSGLGNVGSKM
GLQTNALSKELVGNTLNKVALGMEVTNTAAQSAGGVAEGVFIKNASEALADFMLARFA
MDQIQQWLKQSVEIFGENQKVTAELQKAMSSAVQQNADASRFILRQSRA
(SEQ ID NO: 7)

*Figure 13A*

```
ATGCTTAATATTCAAAATTATTCCGCTTCTCCTCATCCGGGGATCGTTGCCGAACGGCCGCAGACTCCCT
CGGCGAGCGAGCACGTCGAGACTGCCGTGGTACCGTCTACCACAGAACATCGCGGTACAGATATCATTTC
ATTATCGCAGGCGGCTACTAAAATCCACCAGGCACAGCAGACGCTGCAGTCAACGCCACCGATCTCTGAA
GAGAATAATGACGAGCGCACGCTGGCGCGCCAGCAGTTGACCAGCAGCCTGAATGCGCTGGCGAAGTCCG
GCGTGTCATTATCCGCAGAACAAAATGAGAACCTGCGGAGCGCGTTTCTGCGCCGACGTCGGCCTTATT
TAGCGCTTCGCCTATGGCGCAGCCGAGAACAACCATTTCTGATGCTGAGATTTGGGATATGGTTTCCCAA
AATATATCGGCGATAGGTGACAGCTATCTGGGCGTTTATGAAAACGTTGTCGCAGTCTATACCGATTTTT
ATCAGGCCTTCAGTGATATTCTTTCCAAAATGGGAGGCTGGTTATTACCAGGTAAGGACGGTAATACCGT
TAAGCTAGATGTTACCTCACTCAAAAATGATTTAAACAGTTTAGTCAATAAATATAATCAAATAAACAGT
AATACCGTTTTATTTCCAGCGCAGTCAGGCAGCGGCGTTAAAGTAGCCACTGAAGCGGAAGCGAGACAGT
GGCTCAGTGAATTGAATTTACCGAATAGCTGCCTGAAATCTTATGGATCCGGTTATGTCGTCACCGTTGA
TCTGACGCCATTACAAAAATGGTTCAGGATATTGATGGTTTAGGCGCGCCGGGAAAAGACTCAAAACTC
GAAATGGATAACGCCAAATATCAAGCCTGGCAGTCGGGTTTTAAAGCGCAGGAAGAAATATGAAAACCA
CATTACAGACGCTGACGCAAAAATATAGCAATGCCAATTCATTGTACGACAACCTGGTAAAAGTGCTGAG
CAGTACGATAAGTAGCAGCCTGGAAACCGCCAAAAGCTTCCTGCAAGGAGTCGACATGGTAAATGACGCA
AGTAGCATTAGCCGTAGCGGATATACCCAAAATCCGCGCCTCGCTGAGGCGGCTTTTGAAGGCGTTCGTA
AGAACACGGACTTTTTAAAAGCGGCGGATAAAGCTTTTAAAGATGTGGTGGCAACGAAAGCGGGCGACCT
TAAAGCCGGAACAAAGTCCGGCGAGAGCGCTATTAATACGGTGGGTCTAAAGCCGCCTACGGACGCCGCC
CGGGAAAAACTCTCCAGCGAAGGGCAATTGACATTACTGCTTGGCAAGTTAATGACCCTACTGGGCGATG
TTTCGCTGTCTCAACTGGAGTCTCGTCTGGCGGTATGGCAGGCGATGATTGAGTCACAAAAAGAGATGGG
GATTCAGGTATCGAAAGAATTCCAGACGGCTCTGGGAGAGGCTCAGGAGGCGACGGATCTCTATGAAGCC
AGTATCAAAAAGACGGATACCGCCAAGAGTGTTTATGACGCTGCGACCAAAAAACTGACGCAGGCGCAAA
ATAAATTGCAATCGCTGGACCCGGCTGACCCCGGCTATGCACAAGCTGAAGCCGCGGTAGAACAGGCCGG
AAAAGAAGCGACAGAGGCGAAAGAGGCCTTAGATAAGGCCACGGATGCGACGGTTAAAGCAGGCACAGAC
GCCAAAGCGAAAGCCGAGAAAGCGGATAACATTCTGACCAAATTCCAGGGAACGGCTAATGCCGCCTCTC
AGAATCAGGTTTCCCAGGGTGAGCAGGATAATCTGTCAAATGTCGCCCGCCTCACTATGCTCATGGCCAT
GTTTATTGAGATTGTGGGCAAAAATACGGAAGAAAGCCTGCAAAACGATCTTGCGCTTTTCAACGCCTTG
CAGGAAGGGCGTCAGGCGGAGATGGAAAAGAAATCGGCTGAATTCCAGGAAGAGACGCGCAAAGCCGAGG
AAACGAACCGCATTATGGGATGTATCGGGAAAGTCCTCGGCGCGCTGCTAACCATTGTCAGCGTTGTGGC
CGCTGTTTTTACCGGTGGGGCGAGTCTGGCGCTGGCTGCGGTGGGACTTGCGGTAATGGTGGCCGATGAA
ATTGTGAAGGCGGCGACGGGAGTGTCGTTTATTCAGCAGGCGCTAAACCCGATTATGGAGCATGTGCTGA
AGCCGTTAATGGAGCTGATTGGCAAGGCGATTACCAAAGCGCTGGAAGGATTAGGCGTCGATAAGAAAAC
GGCAGAGATGGCCGGCAGCATTGTTGGTGCGATTGTCGCCGCTATTGCCATGGTGGCGGTCATTGTGGTG
GTCGCAGTTGTCGGGAAAGGCGCGGCGGCGAAACTGGGTAACGCGCTGAGCAAAATGATGGGCGAAACGA
TTAAGAAGTTGGTGCCTAACGTGCTGAAACAGTTGGCGCAAAACGGCAGCAAACTCTTTACCCAGGGGAT
GCAACGTATTACTAGCGGTCTGGGTAATGTGGGTAGCAAGATGGGCCTGCAAACGAATGCCTTAAGTAAA
GAGCTGGTAGGTAATACCCTAAATAAAGTGGCGTTGGGCATGGAAGTCACGAATACCGCAGCCCAGTCAG
CCGGTGGTGTTGCCGAGGGCGTATTTATTAAAAATGCCAGCGAGGCGCTTGCTGATTTATGCTCGCCCG
TTTTGCCATGGATCAGATTCAGCAGTGGCTTAAACAATCCGTAGAAATATTTGGTGAAAACCAGAAGGTA
ACGGCGGAACTGCAAAAAGCCATGTCTTCTGCGGTACAGCAAAATGCGGATGCTTCGCGTTTTATTCTGC
GCCAGAGTCGCGCATAA (SEQ ID NO: NO:8)
```

Figure 13B

SEQUENCE LISTING

<160> NUMBER OF SEQ ID NOS: 25

<210> SEQ ID NO 1
<211> LENGTH: 593
<212> TYPE: PRT
<213> ORGANISM: Salmonella enterica

<400> SEQUENCE: 1

```
Met Val Asn Asp Ala Ser Ser Ile Ser Arg Ser Gly Tyr Thr Gln Asn
1               5                   10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Leu Gly Lys Leu Met Thr Leu Leu
                85                  90                  95

Gly Asp Val Ser Leu Ser Gln Leu Glu Ser Arg Leu Ala Val Trp Gln
            100                 105                 110

Ala Met Ile Glu Ser Gln Lys Glu Met Gly Ile Gln Val Ser Lys Glu
        115                 120                 125

Phe Gln Thr Ala Leu Gly Glu Ala Gln Glu Ala Thr Asp Leu Tyr Glu
    130                 135                 140

Ala Ser Ile Lys Lys Thr Asp Thr Ala Lys Ser Val Tyr Asp Ala Ala
145                 150                 155                 160

Thr Lys Lys Leu Thr Gln Ala Gln Asn Lys Leu Gln Ser Leu Asp Pro
                165                 170                 175

Ala Asp Pro Gly Tyr Ala Gln Ala Glu Ala Ala Val Glu Gln Ala Gly
            180                 185                 190

Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
    210                 215                 220

Asn Ile Leu Thr Lys Phe Gln Gly Thr Ala Asn Ala Ala Ser Gln Asn
225                 230                 235                 240

Gln Val Ser Gln Gly Glu Gln Asp Asn Leu Ser Asn Val Ala Arg Leu
                245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
    290                 295                 300
```

Arg Lys Ala Glu Glu Thr Asn Arg Ile Met Gly Cys Ile Gly Lys Val
305                 310                 315                 320

Leu Gly Ala Leu Leu Thr Ile Val Ser Val Ala Ala Val Phe Thr
            325                 330                 335

Gly Gly Ala Ser Leu Ala Leu Ala Ala Val Gly Leu Ala Val Met Val
            340                 345                 350

Ala Asp Glu Ile Val Lys Ala Ala Thr Gly Val Ser Phe Ile Gln Gln
            355                 360                 365

Ala Leu Asn Pro Ile Met Glu His Val Leu Lys Pro Leu Met Glu Leu
370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
                405                 410                 415

Ile Ala Met Val Ala Val Ile Val Val Ala Val Val Gly Lys Gly
                420                 425                 430

Ala Ala Ala Lys Leu Gly Asn Ala Leu Ser Lys Met Met Gly Glu Thr
            435                 440                 445

Ile Lys Lys Leu Val Pro Asn Val Leu Lys Gln Leu Ala Gln Asn Gly
450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
                485                 490                 495

Leu Val Gly Asn Thr Leu Asn Lys Val Ala Leu Gly Met Glu Val Thr
            500                 505                 510

Asn Thr Ala Ala Gln Ser Ala Gly Gly Val Ala Glu Gly Val Phe Ile
            515                 520                 525

Lys Asn Ala Ser Glu Ala Leu Ala Asp Phe Met Leu Ala Arg Phe Ala
530                 535                 540

Met Asp Gln Ile Gln Gln Trp Leu Lys Gln Ser Val Glu Ile Phe Gly
545                 550                 555                 560

Glu Asn Gln Lys Val Thr Ala Glu Leu Gln Lys Ala Met Ser Ser Ala
                565                 570                 575

Val Gln Gln Asn Ala Asp Ala Ser Arg Phe Ile Leu Arg Gln Ser Arg
            580                 585                 590

Ala

<210> SEQ ID NO 2
<211> LENGTH: 1782
<212> TYPE: DNA
<213> ORGANISM: Salmonella enterica

<400> SEQUENCE: 2

```
ttatgcgcga ctctggcgca gaataaaacg cgaagcatcc gcattttgct gtaccgcaga      60
agacatggct ttttgcagtt ccgccgttac cttctggttt tcaccaaata tttctacgga     120
ttgtttaagc cactgctgaa tctgatccat ggcaaaacgg gcgagcataa aatcagcaag     180
cgcctcgctg gcattttaa taaatacgcc tcggcaaca ccaccggctg actgggctgc       240
ggtattcgtg acttccatgc caacgccac tttatttagg gtattaccta ccagctcttt      300
acttaaggca ttcgtttgca ggcccatctt gctacccaca ttcccagac cgctagtaat     360 acgttgcatc ccctgggtaa agagtttgct gccgttttgc gccaactgtt tcagcacgtt     420
```

```
aggcaccaac ttcttaatcg tttcgcccat cattttgctc agcgcgttac ccagtttcgc    480
cgccgcgcct ttcccgacaa ctgcgaccac acaatgacc gccaccatgg caatagcggc     540
gacaatcgca ccaacaatgc tgccggccat ctctgccgtt ttcttatcga cgcctaatcc    600
ttccagcgct ttggtaatcg ccttgccaat cagctccatt aacggcttca gcacatgctc    660
cataatcggg tttagcgcct gctgaataaa cgacactccc gtcgccgcct tcacaatttc    720
atcggccacc attaccgcaa gtcccaccgc agccagcgcc agactcgccc caccggtaaa    780
aacagcggcc acaacgctga caatggttag cagcgcgccg aggactttcc cgatacatcc    840
cataatgcgg ttcgtttcct cggctttgcg cgtctcttcc tggaattcag ccgatttctt    900
ttccatctcc gcctgacgcc cttcctgcaa ggcgttgaaa agcgcaagat cgttttgcag    960
gctttcttcc gtattttgc ccacaatctc aataaacatg ccatgagca tagtgaggcg     1020 ggcgacattt gacagattat cctgctcacc ctgggaaacc tgattctgag aggcggcatt    1080
agccgttccc tggaatttgg tcagaatgtt atccgctttc tcggcttccg ctttggcgtc    1140
tgtgcctgct ttaaccgtcg catccgtggc cttatctaag gcctctttcg cctctgtcgc    1200 ttctttccg gcctgttcta ccgcggcttc agcttgtgca tagccggggt cagccgggtc     1260
cagcgattgc aatttatttt cgcctgcgt cagtttttg gtcgcagcgt cataaacact      1320
cttggcggta ccgtcttttt tgatactggc ttcatagaga tccgtcgcct cctgagcctc    1380
tcccagagcc gtctggaatt cttttcgatac ctgaatcccc atctcttttt gtgactcaat   1440
catcgcctgc cataccgcca gacgagactc cagttgagac agcgaaacat cgcccagtag    1500
ggtcattaac ttgccaagca gtaatgtcaa ttgcccttcg ctggagagtt tttcccgggc    1560
ggcgtccgta ggcggcttta gacccaccgt attaatagcg ctctcgccgg actttgttcc    1620
ggctttaagg tcgcccgctt tcgttgccac cacatcttta aaagctttat ccgccgcttt    1680
taaaaagtcc gtgttcttac gaacgccttc aaaagccgcc tcagcgaggc gcggattttg    1740
ggtatatccg ctacggctaa tgctacttgc gtcatttacc at                       1782
```

<210> SEQ ID NO 3
<211> LENGTH: 339
<212> TYPE: PRT
<213> ORGANISM: Salmonella enterica

<400> SEQUENCE: 3

```
Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Ala Glu Ile Ala
            20                  25                  30

Val Val Pro Ser Thr Thr Glu His Arg Gly Thr Asp Ile Ile Ser Leu
        35                  40                  45

Ser Gln Ala Ala Thr Lys Ile Gln Gln Ala Gln Thr Leu Gln Ser
    50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Thr Phe Ser Ala Arg
            100                 105                 110

Arg Arg Pro Tyr Leu Ala Leu Arg Leu Trp Pro Ala Arg Thr Thr Ile
        115                 120                 125
```

Ser Asp Ala Glu Ile Trp Asp Met Val Ser Gln Asn Ile Ser Ala Ile
130                 135                 140

Gly Asp Ser Tyr Leu Gly Val Tyr Glu Asn Val Ala Val Tyr Thr
145                 150                 155                 160

Asp Phe Tyr Gln Ala Phe Ser Asp Ile Leu Ser Lys Met Gly Gly Trp
                165                 170                 175

Leu Ser Pro Gly Lys Asp Gly Asn Thr Ile Lys Leu Asn Val Asp Ser
            180                 185                 190

Leu Lys Ser Glu Ile Ser Ser Leu Ile Asn Lys Tyr Thr Gln Ile Asn
        195                 200                 205

Lys Asn Thr Ile Leu Phe Pro Ser Gln Thr Gly Ser Gly Met Thr Thr
210                 215                 220

Ala Thr Lys Ala Glu Ala Glu Gln Trp Ile Lys Glu Leu Asn Leu Pro
225                 230                 235                 240

Asp Ser Cys Leu Lys Ala Ser Gly Ser Gly Tyr Val Val Leu Val Asp
                245                 250                 255

Thr Gly Pro Leu Ser Lys Met Val Ser Asp Leu Asn Gly Ile Gly Ser
            260                 265                 270

Gly Ser Ala Leu Glu Leu Asp Asn Ala Lys Tyr Gln Ala Trp Gln Ser
        275                 280                 285

Gly Phe Lys Ala Gln Glu Glu Asn Leu Lys Thr Thr Leu Gln Thr Leu
290                 295                 300

Thr Gln Lys Tyr Ser Asn Ala Asn Ser Leu Tyr Asp Asn Leu Val Lys
305                 310                 315                 320

Val Leu Ser Ser Thr Ile Ser Ser Ser Leu Glu Thr Ala Lys Ser Phe
                325                 330                 335

Leu Gln Gly

<210> SEQ ID NO 4
<211> LENGTH: 1020
<212> TYPE: DNA
<213> ORGANISM: Salmonella enterica

<400> SEQUENCE: 4
atgcttaata ttcaaaatta ttccgcttct cctcatccgg ggatcgttgc cgaacggccg      60
cagactcctt cggcgagcga gcacgccgag attgccgtgg taccgtctac cacagaacat     120
cgcggcacag atatcatttc attatcgcag gcggctacta aaatccagca ggcacagcag     180
acgctgcagt caacgccacc gatttctgaa gagaataatg acgagcgcac gctggcgcgc     240
caacagttga ccagcagcct gaatgcgctg gcgaagtccg gcgtgtcatt atccgcagaa     300
caaaatgaga acctgcggag cacgtttttct gcgcgacgtc ggccttattt agcgcttcgc     360
ctatggccag cgagaacaac catttctgat gctgagattt gggatatggt ttcccaaaat     420
atatcggcga taggtgacag ctacctgggc gtttatgaaa acgttgtcgc agtctatacc     480 gattttttatc aggccttcag tgatattctt tccaaaatgg gaggctggtt atcgcctggt     540
aaggatggaa ataccattaa gctaaatgtt gactcactta aaagtgaaat aagtagttta     600
attaataaat acactcaaat aaataaaaat acgatttttat ttccctcgca aactggcagc     660
ggaatgacaa cagcaacgaa agcggaagct gagcagtgga ttaagaatt gaatttaccg     720 gacagctgtc taaaggcgtc tggttctggt tatgtcgtac tggtggatac ggggccactg     780
agcaaaatgg ttagcgatct taatggaata ggatcgggtt cagcccttga actggataac     840
gccaaatatc aagcctggca gtcgggtttt aaagcacagg aagaaaatct gaaaaccaca     900

-continued

| | | |
|---|---|---|
| ttacagacgc tgacgcaaaa atatagcaat gccaattcat tgtacgacaa cctggtaaaa | 960 | |
| gtgctgagca gtacgataag tagcagcctg gaaaccgcca aaagcttcct gcaaggataa | 1020 | |

<210> SEQ ID NO 5
<211> LENGTH: 196
<212> TYPE: PRT
<213> ORGANISM: Salmonella enterica

<400> SEQUENCE: 5

Met Ser Ser Gly Asn Ile Leu Trp Gly Ser Gln Asn Pro Ile Val Phe
1               5                   10                  15

Lys Asn Ser Phe Gly Val Ser Asn Ala Asp Thr Gly Ser Gln Asp Asp
            20                  25                  30

Leu Ser Gln Gln Asn Pro Phe Ala Glu Gly Tyr Gly Val Leu Leu Ile
        35                  40                  45

Leu Leu Met Val Ile Gln Ala Ile Ala Asn Asn Lys Phe Ile Glu Val
    50                  55                  60

Gln Lys Asn Ala Glu Arg Ala Arg Asn Thr Gln Glu Lys Ser Asn Glu
65                  70                  75                  80

Met Asp Glu Val Ile Ala Lys Ala Lys Gly Asp Ala Lys Thr Lys
                85                  90                  95

Glu Glu Val Pro Glu Asp Val Ile Lys Tyr Met Arg Asp Asn Gly Ile
            100                 105                 110

Leu Ile Asp Gly Met Thr Ile Asp Asp Tyr Met Ala Lys Tyr Gly Asp
        115                 120                 125

His Gly Lys Leu Asp Lys Gly Gly Leu Gln Ala Ile Lys Ala Ala Leu
    130                 135                 140

Asp Asn Asp Ala Asn Arg Asn Thr Asp Leu Met Ser Gln Gly Gln Ile
145                 150                 155                 160

Thr Ile Gln Lys Met Ser Gln Glu Leu Asn Ala Val Leu Thr Gln Leu
                165                 170                 175

Thr Gly Leu Ile Ser Lys Trp Gly Glu Ile Ser Ser Met Ile Ala Gln
            180                 185                 190

Lys Thr Tyr Ser
        195

<210> SEQ ID NO 6
<211> LENGTH: 591
<212> TYPE: DNA
<213> ORGANISM: Salmonella enterica

<400> SEQUENCE: 6

| | | |
|---|---|---|
| atgtcttcag gaaacatctt atggggaagt caaaacccta ttgtgtttaa aaatagcttc | 60 | |
| ggcgtcagca acgctgatac cgggagccag gatgacttat cccagcaaaa tccgtttgcc | 120 | |
| gaagggtatg gtgttttgct tattctcctt atggttattc aggctatcgc aaataataaa | 180 | |
| tttattgaag tccagaagaa cgctgaacgt gccagaaata cccaggaaaa gtcaaatgag | 240 | |
| atggatgagg tgattgctaa agcagccaaa ggggatgcta aaaccaaaga ggaggtgcct | 300 | |
| gaggatgtaa ttaaatacat gcgtgataat ggtattctca tcgatggtat gaccattgat | 360 | |
| gattatatgg ctaaatatgg cgatcatggg aagctggata aggtggcct acaggcgatc | 420 | |
| aaagcggctt tggataatga cgccaaccgg aataccgatc ttatgagtca ggggcagata | 480 | |
| acaattcaaa aaatgtctca ggagcttaac gctgtcctta cccaactgac agggcttatc | 540 | |
| agtaagtggg gggaaatttc cagtatgata gcgcagaaaa cgtactcatg a | 591 | |

-continued

```
<210> SEQ ID NO 7
<211> LENGTH: 934
<212> TYPE: PRT
<213> ORGANISM: Artificial Sequence
<220> FEATURE:
<223> OTHER INFORMATION: Description of Artificial Sequence: Synthetic
      SipD-SipB chimera

<400> SEQUENCE: 7

Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Ala Glu Ile Ala
            20                  25                  30

Val Val Pro Ser Thr Thr Glu His Arg Gly Thr Asp Ile Ile Ser Leu
        35                  40                  45

Ser Gln Ala Ala Thr Lys Ile Gln Gln Ala Gln Gln Thr Leu Gln Ser
    50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Thr Phe Ser Ala Arg
            100                 105                 110

Arg Arg Pro Tyr Leu Ala Leu Arg Leu Trp Pro Ala Arg Thr Thr Ile
        115                 120                 125

Ser Asp Ala Glu Ile Trp Asp Met Val Ser Gln Asn Ile Ser Ala Ile
    130                 135                 140

Gly Asp Ser Tyr Leu Gly Val Tyr Glu Asn Val Ala Val Tyr Thr
145                 150                 155                 160

Asp Phe Tyr Gln Ala Phe Ser Asp Ile Leu Ser Lys Met Gly Gly Trp
                165                 170                 175

Leu Ser Pro Gly Lys Asp Gly Asn Thr Ile Lys Leu Asn Val Asp Ser
            180                 185                 190

Leu Lys Ser Glu Ile Ser Ser Leu Ile Asn Lys Tyr Thr Gln Ile Asn
        195                 200                 205

Lys Asn Thr Ile Leu Phe Pro Ser Gln Thr Gly Ser Gly Met Thr Thr
    210                 215                 220

Ala Thr Lys Ala Glu Ala Glu Gln Trp Ile Lys Glu Leu Asn Leu Pro
225                 230                 235                 240

Asp Ser Cys Leu Lys Ala Ser Gly Ser Gly Tyr Val Val Leu Val Asp
                245                 250                 255

Thr Gly Pro Leu Ser Lys Met Val Ser Asp Leu Asn Gly Ile Gly Ser
            260                 265                 270

Gly Ser Ala Leu Glu Leu Asp Asn Ala Lys Tyr Gln Ala Trp Gln Ser
        275                 280                 285

Gly Phe Lys Ala Gln Glu Glu Asn Leu Lys Thr Thr Leu Gln Thr Leu
    290                 295                 300

Thr Gln Lys Tyr Ser Asn Ala Asn Ser Leu Tyr Asp Asn Leu Val Lys
305                 310                 315                 320

Val Leu Ser Ser Thr Ile Ser Ser Leu Glu Thr Ala Lys Ser Phe
                325                 330                 335

Leu Gln Gly Val Asp Met Val Asn Asp Ala Ser Ser Ile Ser Arg Ser
            340                 345                 350
```

```
Gly Tyr Thr Gln Asn Pro Arg Leu Ala Glu Ala Ala Phe Glu Gly Val
            355                 360                 365

Arg Lys Asn Thr Asp Phe Leu Lys Ala Ala Asp Lys Ala Phe Lys Asp
    370                 375                 380

Val Val Ala Thr Lys Ala Gly Asp Leu Lys Ala Gly Thr Lys Ser Gly
385                 390                 395                 400

Glu Ser Ala Ile Asn Thr Val Gly Leu Lys Pro Pro Thr Asp Ala Ala
                405                 410                 415

Arg Glu Lys Leu Ser Ser Glu Gly Gln Leu Thr Leu Leu Gly Lys
            420                 425                 430

Leu Met Thr Leu Leu Gly Asp Val Ser Leu Ser Gln Leu Glu Ser Arg
        435                 440                 445

Leu Ala Val Trp Gln Ala Met Ile Glu Ser Gln Lys Glu Met Gly Ile
    450                 455                 460

Gln Val Ser Lys Glu Phe Gln Thr Ala Leu Gly Glu Ala Gln Glu Ala
465                 470                 475                 480

Thr Asp Leu Tyr Glu Ala Ser Ile Lys Lys Thr Asp Thr Ala Lys Ser
                485                 490                 495

Val Tyr Asp Ala Ala Thr Lys Lys Leu Thr Gln Ala Gln Asn Lys Leu
            500                 505                 510

Gln Ser Leu Asp Pro Ala Asp Pro Gly Tyr Ala Gln Ala Glu Ala Ala
        515                 520                 525

Val Glu Gln Ala Gly Lys Glu Ala Thr Glu Ala Lys Glu Ala Leu Asp
530                 535                 540

Lys Ala Thr Asp Ala Thr Val Lys Ala Gly Thr Asp Ala Lys Ala Lys
545                 550                 555                 560

Ala Glu Lys Ala Asp Asn Ile Leu Thr Lys Phe Gln Gly Thr Ala Asn
                565                 570                 575

Ala Ala Ser Gln Asn Gln Val Ser Gln Gly Glu Gln Asp Asn Leu Ser
            580                 585                 590

Asn Val Ala Arg Leu Thr Met Leu Met Ala Met Phe Ile Glu Ile Val
        595                 600                 605

Gly Lys Asn Thr Glu Glu Ser Leu Gln Asn Asp Leu Ala Leu Phe Asn
    610                 615                 620

Ala Leu Gln Glu Gly Arg Gln Ala Glu Met Glu Lys Lys Ser Ala Glu
625                 630                 635                 640

Phe Gln Glu Glu Thr Arg Lys Ala Glu Thr Asn Arg Ile Met Gly
                645                 650                 655

Cys Ile Gly Lys Val Leu Gly Ala Leu Leu Thr Ile Val Ser Val Val
            660                 665                 670

Ala Ala Val Phe Thr Gly Gly Ala Ser Leu Ala Leu Ala Ala Val Gly
        675                 680                 685

Leu Ala Val Met Val Ala Asp Glu Ile Val Lys Ala Ala Thr Gly Val
    690                 695                 700

Ser Phe Ile Gln Gln Ala Leu Asn Pro Ile Met Glu His Val Leu Lys
705                 710                 715                 720

Pro Leu Met Glu Leu Ile Gly Lys Ala Ile Thr Lys Ala Leu Glu Gly
                725                 730                 735

Leu Gly Val Asp Lys Lys Thr Ala Glu Met Ala Gly Ser Ile Val Gly
            740                 745                 750

Ala Ile Val Ala Ala Ile Ala Met Val Ala Val Ile Val Val Ala
        755                 760                 765
```

Val Val Gly Lys Gly Ala Ala Ala Lys Leu Gly Asn Ala Leu Ser Lys
770                 775                 780

Met Met Gly Glu Thr Ile Lys Lys Leu Val Pro Asn Val Leu Lys Gln
785                 790                 795                 800

Leu Ala Gln Asn Gly Ser Lys Leu Phe Thr Gln Gly Met Gln Arg Ile
            805                 810                 815

Thr Ser Gly Leu Gly Asn Val Gly Ser Lys Met Gly Leu Gln Thr Asn
            820                 825                 830

Ala Leu Ser Lys Glu Leu Val Gly Asn Thr Leu Asn Lys Val Ala Leu
            835                 840                 845

Gly Met Glu Val Thr Asn Thr Ala Ala Gln Ser Ala Gly Gly Val Ala
850                 855                 860

Glu Gly Val Phe Ile Lys Asn Ala Ser Glu Ala Leu Ala Asp Phe Met
865                 870                 875                 880

Leu Ala Arg Phe Ala Met Asp Gln Ile Gln Gln Trp Leu Lys Gln Ser
            885                 890                 895

Val Glu Ile Phe Gly Glu Asn Gln Lys Val Thr Ala Glu Leu Gln Lys
            900                 905                 910

Ala Met Ser Ser Ala Val Gln Gln Asn Ala Asp Ala Ser Arg Phe Ile
            915                 920                 925

Leu Arg Gln Ser Arg Ala
    930

<210> SEQ ID NO 8
<211> LENGTH: 2817
<212> TYPE: DNA
<213> ORGANISM: Artificial Sequence
<220> FEATURE:
<223> OTHER INFORMATION: Description of Artificial Sequence: Synthetic
      nucleic acid sequence encoding SipD-SipB chimera

<400> SEQUENCE: 8
atgcttaata ttcaaaatta ttccgcttct cctcatccgg ggatcgttgc cgaacggccg      60
cagactccct cggcgagcga gcacgtcgag actgccgtgg taccgtctac cacagaacat     120
cgcggtacag atatcatttc attatcgcag gcggctacta aaatccacca ggcacagcag     180
acgctgcagt caacgccacc gatctctgaa gagaataatg acgagcgcac gctggcgcgc     240
cagcagttga ccagcagcct gaatgcgctg gcgaagtccg gcgtgtcatt atccgcagaa     300
caaaatgaga acctgcggag cgcgtttttct gcgccgacgt cggccttatt tagcgcttcg     360 cctatgcgc agccgagaac aaccatttct gatgctgaga tttgggatat ggtttcccaa     420
aatatatcgg cgataggtga cagctatctg ggcgtttatg aaaacgttgt cgcagtctat     480
accgattttt atcaggcctt cagtgatatt ctttccaaaa tgggaggctg gttattacca     540
ggtaaggacg gtaataccgt taagctagat gttacctcac tcaaaaatga tttaaacagt     600
ttagtcaata atataatca ataaacagt aataccgttt tatttccagc gcagtcaggc     660
agcggcgtta agtagccac tgaagcgaa gcgagacagt ggctcagtga attgaattta     720
ccgaatagct gcctgaaatc ttatggatcc ggttatgtcg tcaccgttga tctgacgcca     780
ttacaaaaaa tggttcagga tattgatggt ttaggcgcgc cgggaaaaga ctcaaaactc     840
gaaatggata acgccaaata tcaagcctgg cagtcgggtt ttaaagcgca ggaagaaaat     900
atgaaaacca cattacagac gctgacgcaa aaatatagca tgccaattc attgtacgac     960 aacctggtaa aagtgctgag cagtacgata agtagcagcc tggaaccgc caaaagcttc    1020 ctgcaaggag tcgacatggt aaatgacgca agtagcatta gccgtagcgg atatacccaa    1080

```
aatccgcgcc tcgctgaggc ggcttttgaa ggcgttcgta agaacacgga cttttaaaa      1140
gcggcggata aagcttttaa agatgtggtg gcaacgaaag cgggcgacct taaagccgga     1200
acaaagtccg gcgagagcgc tattaatacg gtgggtctaa agccgcctac ggacgccgcc    1260
cgggaaaaac tctccagcga agggcaattg acattactgc ttggcaagtt aatgaccta     1320
ctgggcgatg tttcgctgtc tcaactggag tctcgtctgg cggtatggca ggcgatgatt    1380
gagtcacaaa aagagatggg gattcaggta tcgaaagaat tccagacggc tctgggagag    1440
gctcaggagg cgacggatct ctatgaagcc agtatcaaaa agacggatac cgccaagagt    1500
gtttatgacg ctgcgaccaa aaaactgacg caggcgcaaa ataaattgca atcgctggac    1560
ccggctgacc ccggctatgc acaagctgaa gccgcggtag aacaggccgg aaaagaagcg    1620
acagaggcga aagaggcctt agataaggcc acggatgcga cggttaaagc aggcacagac    1680
gccaaagcga aagccgagaa agcggataac attctgacca aattccaggg aacggctaat    1740
gccgcctctc agaatcaggt ttcccagggt gagcaggata tctgtcaaa tgtcgcccgc     1800
ctcactatgc tcatggccat gtttattgag attgtgggca aaaatacgga agaaagcctg    1860
caaaacgatc ttgcgctttt caacgccttg caggaagggc gtcaggcgga gatggaaaag   1920
aaatcggctg aattccagga agagacgcgc aaagccgagg aaacgaaccg cattatggga   1980
tgtatcggga aagtcctcgg cgcgctgcta accattgtca gcgttgtggc cgctgttttt    2040
accggtgggg cgagtctggc gctggctgcg gtgggacttg cggtaatggt ggccgatgaa    2100
attgtgaagg cggcgacggg agtgtcgttt attcagcagg cgctaaaccc gattatggag   2160
catgtgctga agccgttaat ggagctgatt ggcaaggcga ttaccaaagc gctggaagga   2220
ttaggcgtcg ataagaaaac ggcagagatg ccggcagca ttgttggtgc gattgtcgcc    2280
gctattgcca tggtggcggt cattgtggtg gtcgcagttg tcgggaaagg cgcggcggcg   2340
aaactgggta acgcgctgag caaaatgatg ggcgaaacga ttaagaagtt ggtgcctaac    2400
gtgctgaaac agttggcgca aaacggcagc aaactcttta cccagggat gcaacgtatt    2460
actagcggtc tgggtaatgt gggtagcaag atgggcctgc aaacgaatgc cttaagtaaa   2520
gagctggtag gtaataccct aaataaagtg gcgttgggca tggaagtcac gaataccgca   2580
gcccagtcag ccggtggtgt tgccgagggc gtatttatta aaaatgccag cgaggcgctt    2640
gctgatttta tgctcgcccg ttttgccatg gatcagattc agcagtggct taaacaatcc    2700
gtagaaatat ttggtgaaaa ccagaaggta acggcggaac tgcaaaaagc catgtcttct   2760
gcggtacagc aaaatgcgga tgcttcgcgt tttattctgc gccagagtcg cgcataa      2817
```

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13
<211> LENGTH: 2877
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | | | | | |
|---|---|---|---|---|---|
| atgggcagca | gccatcatca | tcatcatcac | agcagcggcc | tggtgccgcg | cggcagccat | 60 |
| atgcttaata | ttcaaaatta | ttccgcttct | cctcatccgg | ggatcgttgc | cgaacggccg | 120 |
| cagactccct | cggcgagcga | gcacgtcgag | actgccgtgg | taccgtctac | cacagaacat | 180 |
| cgcggtacag | atatcatttc | attatcgcag | gcggctacta | aaatccacca | ggcacagcag | 240 |
| acgctgcagt | caacgccacc | gatctctgaa | gagaataatg | acgagcgcac | gctggcgcgc | 300 |
| cagcagttga | ccagcagcct | gaatgcgctg | gcgaagtccg | gcgtgtcatt | atccgcagaa | 360 |
| caaaatgaga | acctgcggag | cgcgtttttct | gcgccgacgt | cggccttatt | tagcgcttcg | 420 |
| cctatggcgc | agccgagaac | aaccatttct | gatgctgaga | tttgggatat | ggtttcccaa | 480 |
| aatatatcgg | cgataggtga | cagctatctg | ggcgtttatg | aaaacgttgt | cgcagtctat | 540 |
| accgattttt | atcaggcctt | cagtgatatt | ctttccaaaa | tgggaggctg | gttattacca | 600 |
| ggtaaggacg | gtaataccgt | taagctagat | gttacctcac | tcaaaaatga | tttaaacagt | 660 |
| ttagtcaata | aatataatca | aataaacagt | aataccgttt | tatttccagc | gcagtcaggc | 720 |
| agcggcgtta | agtagccac | tgaagcgaa | gcgagacagt | ggctcagtga | attgaattta | 780 |
| ccgaatagct | gcctgaaatc | ttatggatcc | ggttatgtcg | tcaccgttga | tctgacgcca | 840 |
| ttacaaaaaa | tggttcagga | tattgatggt | ttaggcgcgc | cgggaaaaga | ctcaaaactc | 900 |
| gaaatggata | acgccaaata | tcaagcctgg | cagtcgggtt | taaagcgca | ggaagaaaat | 960 |
| atgaaaacca | cattacagac | gctgacgcaa | aaatatagca | atgccaattc | attgtacgac | 1020 |
| aacctggtaa | aagtgctgag | cagtacgata | agtagcagcc | tggaaaccgc | caaaagcttc | 1080 |
| ctgcaaggag | tcgacatggt | aaatgacgca | agtagcatta | gccgtagcgg | atatacccaa | 1140 |
| aatccgcgcc | tcgctgaggc | ggcttttgaa | ggcgttcgta | agaacacgga | cttttttaaaa | 1200 |
| gcggcggata | agcttttaa | agatgtggtg | gcaacgaaag | cgggcgaccct | taaagccgga | 1260 |
| acaaagtccg | gcgagagcgc | tattaatacg | gtgggtctaa | agccgcctac | ggacgccgcc | 1320 |
| cgggaaaaac | tctccagcga | agggcaattg | acattactgc | ttggcaagtt | aatgaccta | 1380 |
| ctgggcgatg | tttcgctgtc | tcaactggag | tctcgtctgg | cggtatggca | ggcgatgatt | 1440 |
| gagtcacaaa | aagagatggg | gattcaggta | tcgaaagaat | tccagacggc | tctgggagag | 1500 |
| gctcaggagg | cgacggatct | ctatgaagcc | agtatcaaaa | agacggatac | cgccaagagt | 1560 |
| gtttatgacg | ctgcgaccaa | aaaactgacg | caggcgcaaa | ataaattgca | atcgctggac | 1620 |
| ccggctgacc | ccggctatgc | acaagctgaa | gccgcggtag | aacaggccgg | aaaagaagcg | 1680 |
| acagaggcga | agaggccctt | agataaggcc | acggatgcga | cggttaaagc | aggcacagac | 1740 |
| gccaaagcga | agccgagaa | agcggataac | attctgacca | aattccaggg | aacggctaat | 1800 |

-continued

```
gccgcctctc agaatcaggt ttcccagggt gagcaggata atctgtcaaa tgtcgcccgc    1860
ctcactatgc tcatggccat gtttattgag attgtgggca aaaatacgga agaaagcctg    1920
caaaacgatc ttgcgctttt caacgccttg caggaagggc gtcaggcgga tggaaaag      1980 aaatcggctg aattccagga agagacgcgc aaagccgagg aaacgaaccg cattatggga    2040
tgtatcggga aagtcctcgg cgcgctgcta accattgtca gcgttgtggc cgctgttttt    2100
accggtgggg cgagtctggc gctggctgcg gtgggacttg cggtaatggt ggccgatgaa    2160
attgtgaagg cggcgacggg agtgtcgttt attcagcagg cgctaaaccc gattatggag    2220
catgtgctga agccgttaat ggagctgatt ggcaaggcga ttaccaaagc gctggaagga    2280
ttaggcgtcg ataagaaaac ggcagagatg gccggcagca ttgttggtgc gattgtcgcc    2340
gctattgcca tggtggcggt cattgtggtg gtcgcagttg tcgggaaagg cgcggcggcg    2400
aaactgggta acgcgctgag caaaatgatg ggcgaaacga ttaagaagtt ggtgcctaac    2460
gtgctgaaac agttggcgca aaacggcagc aaactcttta cccagggat gcaacgtatt     2520 actagcggtc tgggtaatgt gggtagcaag atgggcctgc aaacgaatgc cttaagtaaa    2580
gagctggtag gtaataccct aaataaagtg gcgttgggca tggaagtcac gaataccgca    2640
gcccagtcag ccggtggtgt tgccgaggc gtatttatta aaaatgccag cgaggcgctt      2700
gctgatttta tgctcgcccg ttttgccatg gatcagattc agcagtggct taaacaatcc    2760
gtagaaatat ttggtgaaaa ccagaaggta acggcggaac tgcaaaaagc catgtcttct    2820
gcggtacagc aaaatgcgga tgcttcgcgt tttattctgc gccagagtcg cgcataa        2877
```

<210> SEQ ID NO 14
<211> LENGTH: 958
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Gly Ser Ser His His His His His His Ser Ser Gly Leu Val Pro
1               5                   10                  15

Arg Gly Ser His Met Leu Asn Ile Gln Asn Tyr Ser Ala Ser Pro His
            20                  25                  30

Pro Gly Ile Val Ala Glu Arg Pro Gln Thr Pro Ser Ala Ser Glu His
        35                  40                  45

Val Glu Thr Ala Val Val Pro Ser Thr Thr Glu His Arg Gly Thr Asp
    50                  55                  60

Ile Ile Ser Leu Ser Gln Ala Ala Thr Lys Ile His Gln Ala Gln Gln
65                  70                  75                  80

Thr Leu Gln Ser Thr Pro Pro Ile Ser Glu Glu Asn Asn Asp Glu Arg
                85                  90                  95

Thr Leu Ala Arg Gln Gln Leu Thr Ser Ser Leu Asn Ala Leu Ala Lys
            100                 105                 110

Ser Gly Val Ser Leu Ser Ala Glu Gln Asn Glu Asn Leu Arg Ser Ala
        115                 120                 125

Phe Ser Ala Pro Thr Ser Ala Leu Phe Ser Ala Ser Pro Met Ala Gln
    130                 135                 140

Pro Arg Thr Thr Ile Ser Asp Ala Glu Ile Trp Asp Met Val Ser Gln
145                 150                 155                 160

Asn Ile Ser Ala Ile Gly Asp Ser Tyr Leu Gly Val Tyr Glu Asn Val
                165                 170                 175
```

```
Val Ala Val Tyr Thr Asp Phe Tyr Gln Ala Phe Ser Asp Ile Leu Ser
            180                 185                 190

Lys Met Gly Gly Trp Leu Leu Pro Gly Lys Asp Gly Asn Thr Val Lys
        195                 200                 205

Leu Asp Val Thr Ser Leu Lys Asn Asp Leu Asn Ser Leu Val Asn Lys
210                 215                 220

Tyr Asn Gln Ile Asn Ser Asn Thr Val Leu Phe Pro Ala Gln Ser Gly
225                 230                 235                 240

Ser Gly Val Lys Val Ala Thr Glu Ala Glu Ala Arg Gln Trp Leu Ser
                245                 250                 255

Glu Leu Asn Leu Pro Asn Ser Cys Leu Lys Ser Tyr Gly Ser Gly Tyr
            260                 265                 270

Val Val Thr Val Asp Leu Thr Pro Leu Gln Lys Met Val Gln Asp Ile
            275                 280                 285

Asp Gly Leu Gly Ala Pro Gly Lys Asp Ser Lys Leu Glu Met Asp Asn
    290                 295                 300

Ala Lys Tyr Gln Ala Trp Gln Ser Gly Phe Lys Ala Gln Glu Glu Asn
305                 310                 315                 320

Met Lys Thr Thr Leu Gln Thr Leu Thr Gln Lys Tyr Ser Asn Ala Asn
                325                 330                 335

Ser Leu Tyr Asp Asn Leu Val Lys Val Leu Ser Ser Thr Ile Ser Ser
            340                 345                 350

Ser Leu Glu Thr Ala Lys Ser Phe Leu Gln Gly Val Asp Met Val Asn
        355                 360                 365

Asp Ala Ser Ser Ile Ser Arg Ser Gly Tyr Thr Gln Asn Pro Arg Leu
    370                 375                 380

Ala Glu Ala Ala Phe Glu Gly Val Arg Lys Asn Thr Asp Phe Leu Lys
385                 390                 395                 400

Ala Ala Asp Lys Ala Phe Lys Asp Val Val Ala Thr Lys Ala Gly Asp
                405                 410                 415

Leu Lys Ala Gly Thr Lys Ser Gly Glu Ser Ala Ile Asn Thr Val Gly
            420                 425                 430

Leu Lys Pro Pro Thr Asp Ala Ala Arg Glu Lys Leu Ser Ser Glu Gly
        435                 440                 445

Gln Leu Thr Leu Leu Leu Gly Lys Leu Met Thr Leu Leu Gly Asp Val
    450                 455                 460

Ser Leu Ser Gln Leu Glu Ser Arg Leu Ala Val Trp Gln Ala Met Ile
465                 470                 475                 480

Glu Ser Gln Lys Glu Met Gly Ile Gln Val Ser Lys Glu Phe Gln Thr
                485                 490                 495

Ala Leu Gly Glu Ala Gln Glu Ala Thr Asp Leu Tyr Glu Ala Ser Ile
            500                 505                 510

Lys Lys Thr Asp Thr Ala Lys Ser Val Tyr Asp Ala Ala Thr Lys Lys
        515                 520                 525

Leu Thr Gln Ala Gln Asn Lys Leu Gln Ser Leu Asp Pro Ala Asp Pro
    530                 535                 540

Gly Tyr Ala Gln Ala Glu Ala Val Glu Gln Ala Gly Lys Glu Ala
545                 550                 555                 560

Thr Glu Ala Lys Glu Ala Leu Asp Lys Ala Thr Asp Ala Thr Val Lys
                565                 570                 575

Ala Gly Thr Asp Ala Lys Ala Lys Ala Glu Lys Ala Asp Asn Ile Leu
            580                 585                 590
```

-continued

Thr Lys Phe Gln Gly Thr Ala Asn Ala Ala Ser Gln Asn Gln Val Ser
            595                 600                 605

Gln Gly Glu Gln Asp Asn Leu Ser Asn Val Ala Arg Leu Thr Met Leu
    610                 615                 620

Met Ala Met Phe Ile Glu Ile Val Gly Lys Asn Thr Glu Glu Ser Leu
625                 630                 635                 640

Gln Asn Asp Leu Ala Leu Phe Asn Ala Leu Gln Glu Gly Arg Gln Ala
                645                 650                 655

Glu Met Glu Lys Lys Ser Ala Glu Phe Gln Glu Thr Arg Lys Ala
            660                 665                 670

Glu Glu Thr Asn Arg Ile Met Gly Cys Ile Gly Lys Val Leu Gly Ala
    675                 680                 685

Leu Leu Thr Ile Val Ser Val Ala Ala Val Phe Thr Gly Gly Ala
690                 695                 700

Ser Leu Ala Leu Ala Ala Val Gly Leu Ala Val Met Val Ala Asp Glu
705                 710                 715                 720

Ile Val Lys Ala Ala Thr Gly Val Ser Phe Ile Gln Gln Ala Leu Asn
                725                 730                 735

Pro Ile Met Glu His Val Leu Lys Pro Leu Met Glu Leu Ile Gly Lys
            740                 745                 750

Ala Ile Thr Lys Ala Leu Glu Gly Leu Gly Val Asp Lys Lys Thr Ala
    755                 760                 765

Glu Met Ala Gly Ser Ile Val Gly Ala Ile Val Ala Ala Ile Ala Met
770                 775                 780

Val Ala Val Ile Val Val Val Ala Val Val Gly Lys Gly Ala Ala Ala
785                 790                 795                 800

Lys Leu Gly Asn Ala Leu Ser Lys Met Met Gly Glu Thr Ile Lys Lys
                805                 810                 815

Leu Val Pro Asn Val Leu Lys Gln Leu Ala Gln Asn Gly Ser Lys Leu
            820                 825                 830

Phe Thr Gln Gly Met Gln Arg Ile Thr Ser Gly Leu Gly Asn Val Gly
    835                 840                 845

Ser Lys Met Gly Leu Gln Thr Asn Ala Leu Ser Lys Glu Leu Val Gly
850                 855                 860

Asn Thr Leu Asn Lys Val Ala Leu Gly Met Glu Val Thr Asn Thr Ala
865                 870                 875                 880

Ala Gln Ser Ala Gly Gly Val Ala Glu Gly Val Phe Ile Lys Asn Ala
                885                 890                 895

Ser Glu Ala Leu Ala Asp Phe Met Leu Ala Arg Phe Ala Met Asp Gln
            900                 905                 910

Ile Gln Gln Trp Leu Lys Gln Ser Val Glu Ile Phe Gly Glu Asn
    915                 920                 925

Lys Val Thr Ala Glu Leu Gln Lys Ala Met Ser Ser Ala Val Gln Gln
930                 935                 940

Asn Ala Asp Ala Ser Arg Phe Ile Leu Arg Gln Ser Arg Ala
945                 950                 955

<210> SEQ ID NO 15
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atgggcagca gccatcatca tcatcatcac agcagcggcc tggtgccgcg cggcagccat     60
atgtcttcag gaaacatctt atggggaagt caaaccccta ttgtgtttaa aaatagcttc    120
ggcgtcagca acgctgatac cgggagccag gatgacttat cccagcaaaa tccgtttgcc    180
gaagggtatg gtgttttgct tattctcctt atggttattc aggctatcgc aaataataaa    240
tttattgaag tccagaagaa cgctgaacgt gccagaaata cccaggaaaa gtcaaatgag    300
atggatgagg tgattgctaa agcagccaaa ggggatgcta aaccaaaga ggaggtgcct     360
gaggatgtaa ttaaatacat gcgtgataat ggtattctca tcgatggtat gaccattgat    420
gattatatgg ctaaatatgg cgatcatggg aagctggata aggtggcct acaggcgatc     480
aaagcggctt tggataatga cgccaaccgg aataccgatc ttatgagtca ggggcagata    540
acaattcaaa aatgtctca ggagcttaac gctgtcctta cccaactgac agggcttatc     600
agtaagtggg gggaaatttc cagtatgata gcgcagaaaa cgtactcacc gcggatgaat    660
cgaattcaca gtaatagcga cagcgccgca ggagtaaccg ccttaacaca tcatcactta    720
agcaatgtca gttgcgtttc ctcgggttcg ctgggaaagc gccagcatcg tgtgaattct    780
acttttggcg atggcaacgc cgcgtgtctg ctatccggga aaattagtct tcaggaggca    840
agcaatgcgt gaagcaact gcttgatgcc gtacccggaa atcataagcg tccatcattg     900
cctgactttt tgcagaccaa tcccgcggtt ttatcaatga tgatgacgtc attaatactc    960
aacgtctttg gtaataacgc tcaatcgtta tgccaacagc ttgagcgggc aactgaggtg   1020
caaaatgcat tacgtaataa gcaggtaaag gagtatcagg agcagatcca gaaagcgata   1080
gagcaggagg ataaagcgcg taaagcgggt attttttggcg ctattttga ctggattacc   1140
ggcatatttg aaaccgtgat tggcgcctta aaagttgtgg aaggttttct gtccggaaat   1200
cccgcagaaa tggctagcgg cgtagcttat atggccgcag gttgtgcagg aatggttaaa   1260
gccggagccg aaacggcaat gatgtgcggt gctgaccacg atacctgtca ggcaattatt   1320
gacgtgacaa gtaagattca atttggttgt gaagccgtcg cgctggcact ggatgttttc   1380
cagattggcc gtgctttat ggcgacgaga ggtttatctg gcgcagctgc aaaagtgctt    1440
gactccggtt ttggcgagga agtggttgag cgtatggtag gtgcagggga agcagaaata   1500
gaggagttgg ctgaaaagtt tggcgaagaa gtgagcgaaa gttttttccaa acaatttgag   1560
ccgcttgaac gtgaaatggc tatggcgaat gagatggcag aggaggctgc gagtttttct   1620
cgtaacgtag aaaataatat gacgcgaagc gcgggaaaaa gctttacgaa agaggggggtg   1680
aaagccatgg caaaagaagc ggcaaaagaa gccctggaaa atgtgtgcca agaaggtgga    1740
aagttcctgt taaaaaaatt ccgtaataaa gttctcttca atatgttcaa aaaaatcctg   1800
tatgccttac tgagggattg ttcatttaaa ggcttacagg ctatcagatg tgcaaccgag   1860
ggcgccagtc agatgaatac tggcatggtt aacacagaaa aagcgaagat cgaaaagaaa   1920
atagagcaat taataactca gcaacggttt ctggatttca taatgcaaca aacagaaaac   1980
cagaaaaaga tagaacaaaa acgcttagag gagctttata aggggagcgg tgccgcgctt   2040
agagatgtat tagataccat tgatcactat agtagcgttc aggcgagaat agctggctat   2100
cgcgcttaa                                                          2109
```

<210> SEQ ID NO 16
<211> LENGTH: 702
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 16

Met Gly Ser Ser His His His His His His Ser Ser Gly Leu Val Pro
1               5                   10                  15

Arg Gly Ser His Met Ser Gly Asn Ile Leu Trp Gly Ser Gln Asn
            20                  25                  30

Pro Ile Val Phe Lys Asn Ser Phe Gly Val Ser Asn Ala Asp Thr Gly
                35                  40                  45

Ser Gln Asp Asp Leu Ser Gln Gln Asn Pro Phe Ala Glu Gly Tyr Gly
    50                  55                  60

Val Leu Leu Ile Leu Leu Met Val Ile Gln Ala Ile Ala Asn Asn Lys
65                  70                  75                  80

Phe Ile Glu Val Gln Lys Asn Ala Glu Arg Ala Arg Asn Thr Gln Glu
                85                  90                  95

Lys Ser Asn Glu Met Asp Glu Val Ile Ala Lys Ala Ala Lys Gly Asp
            100                 105                 110

Ala Lys Thr Lys Glu Glu Val Pro Glu Asp Val Ile Lys Tyr Met Arg
        115                 120                 125

Asp Asn Gly Ile Leu Ile Asp Gly Met Thr Ile Asp Asp Tyr Met Ala
130                 135                 140

Lys Tyr Gly Asp His Gly Lys Leu Asp Lys Gly Gly Leu Gln Ala Ile
145                 150                 155                 160

Lys Ala Ala Leu Asp Asn Asp Ala Asn Arg Asn Thr Asp Leu Met Ser
                165                 170                 175

Gln Gly Gln Ile Thr Ile Gln Lys Met Ser Gln Glu Leu Asn Ala Val
            180                 185                 190

Leu Thr Gln Leu Thr Gly Leu Ile Ser Lys Trp Gly Glu Ile Ser Ser
        195                 200                 205

Met Ile Ala Gln Lys Thr Tyr Ser Pro Arg Met Asn Arg Ile His Ser
210                 215                 220

Asn Ser Asp Ser Ala Ala Gly Val Thr Ala Leu Thr His His His Leu
225                 230                 235                 240

Ser Asn Val Ser Cys Val Ser Ser Gly Ser Leu Gly Lys Arg Gln His
                245                 250                 255

Arg Val Asn Ser Thr Phe Gly Asp Gly Asn Ala Ala Cys Leu Leu Ser
            260                 265                 270

Gly Lys Ile Ser Leu Gln Glu Ala Ser Asn Ala Leu Lys Gln Leu Leu
        275                 280                 285

Asp Ala Val Pro Gly Asn His Lys Arg Pro Ser Leu Pro Asp Phe Leu
290                 295                 300

Gln Thr Asn Pro Ala Val Leu Ser Met Met Met Thr Ser Leu Ile Leu
305                 310                 315                 320

Asn Val Phe Gly Asn Asn Ala Gln Ser Leu Cys Gln Gln Leu Glu Arg
                325                 330                 335

Ala Thr Glu Val Gln Asn Ala Leu Arg Asn Lys Gln Val Lys Glu Tyr
            340                 345                 350

Gln Glu Gln Ile Gln Lys Ala Ile Glu Gln Glu Asp Lys Ala Arg Lys
        355                 360                 365

Ala Gly Ile Phe Gly Ala Ile Phe Asp Trp Ile Thr Gly Ile Phe Glu
370                 375                 380

-continued

Thr Val Ile Gly Ala Leu Lys Val Val Glu Gly Phe Leu Ser Gly Asn
385                 390                 395                 400

Pro Ala Glu Met Ala Ser Gly Val Ala Tyr Met Ala Ala Gly Cys Ala
            405                 410                 415

Gly Met Val Lys Ala Gly Ala Glu Thr Ala Met Met Cys Gly Ala Asp
            420                 425                 430

His Asp Thr Cys Gln Ala Ile Ile Asp Val Thr Ser Lys Ile Gln Phe
            435                 440                 445

Gly Cys Glu Ala Val Ala Leu Ala Leu Asp Val Phe Gln Ile Gly Arg
450                 455                 460

Ala Phe Met Ala Thr Arg Gly Leu Ser Gly Ala Ala Lys Val Leu
465                 470                 475                 480

Asp Ser Gly Phe Gly Glu Val Val Glu Arg Met Val Gly Ala Gly
                485                 490                 495

Glu Ala Glu Ile Glu Glu Leu Ala Glu Lys Phe Gly Glu Glu Val Ser
                500                 505                 510

Glu Ser Phe Ser Lys Gln Phe Glu Pro Leu Glu Arg Glu Met Ala Met
    515                 520                 525

Ala Asn Glu Met Ala Glu Glu Ala Glu Phe Ser Arg Asn Val Glu
530                 535                 540

Asn Asn Met Thr Arg Ser Ala Gly Lys Ser Phe Thr Lys Glu Gly Val
545                 550                 555                 560

Lys Ala Met Ala Lys Glu Ala Lys Glu Ala Leu Glu Lys Cys Val
                565                 570                 575

Gln Glu Gly Gly Lys Phe Leu Leu Lys Lys Phe Arg Asn Lys Val Leu
                580                 585                 590

Phe Asn Met Phe Lys Lys Ile Leu Tyr Ala Leu Leu Arg Asp Cys Ser
    595                 600                 605

Phe Lys Gly Leu Gln Ala Ile Arg Cys Ala Thr Glu Gly Ala Ser Gln
    610                 615                 620

Met Asn Thr Gly Met Val Asn Thr Glu Lys Ala Lys Ile Glu Lys Lys
625                 630                 635                 640

Ile Glu Gln Leu Ile Thr Gln Arg Phe Leu Asp Phe Ile Met Gln
                645                 650                 655

Gln Thr Glu Asn Gln Lys Lys Ile Glu Gln Lys Arg Leu Glu Glu Leu
                660                 665                 670

Tyr Lys Gly Ser Gly Ala Ala Leu Arg Asp Val Leu Asp Thr Ile Asp
    675                 680                 685

His Tyr Ser Ser Val Gln Ala Arg Ile Ala Gly Tyr Arg Ala
    690                 695                 700

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 1455
<212> TYPE: DNA
<213> ORGANISM: Salmonella typhimurium

<400> SEQUENCE: 23

```
atgaatcgaa ttcacagtaa tagcgacagc gccgcaggag taaccgcctt aacacatcat    60
cacttaagca atgtcagttg cgtttcctcg ggttcgctgg gaaagcgcca gcatcgtgtg   120
aattctactt ttggcgatgg caacgccgcg tgtctgctat ccgggaaaat tagtcttcag   180
gaggcaagca atgcgttgaa gcaactgctt gatgccgtac ccggaaatca taagcgtcca   240
tcattgcctg actttttgca gaccaatccc gcggttttat caatgatgat gacgtcatta   300
atactcaacg tctttggtaa taacgctcaa tcgttatgcc aacagcttga gcgggcaact   360
gaggtgcaaa atgcattacg taataagcag gtaaaggagt atcaggagca gatccagaaa   420
gcgatagagc aggaggataa agcgcgtaaa gcgggtattt ttggcgctat ttttgactgg   480
attaccggca tatttgaaac cgtgattggc gccttaaaag ttgtggaagg ttttctgtcc   540
ggaaatcccg cagaaatggc tagcggcgta gcttatatgg ccgcaggttg tgcaggaatg   600
gttaaagccg gagccgaaac ggcaatgatg tgcggtgctg accacgatac ctgtcaggca   660
attattgacg tgacaagtaa gattcaattt ggttgtgaag ccgtcgcgct ggcactggat   720
gttttccaga ttggccgtgc ttttatggcg acgagaggtt tatctggcgc agctgcaaaa   780
gtgcttgact ccggttttgg cgaggaagtg gttgagcgta tggtaggtgc agggaagca   840 gaaatagagg agttggctga aaagtttggc gaagaagtga gcgaaagttt tccaaacaa   900 tttgagccgc ttgaacgtga atggctatg gcgaatgaga tggcagagga ggctgccgag   960
ttttctcgta acgtagaaaa taatatgacg cgaagcgcgg gaaaagctt tacgaaagag  1020 ggggtgaaag ccatggcaaa agaagcggca aagaagccc tggaaaaatg tgtgcaagaa  1080
ggtggaaagt tcctgttaaa aaaattccgt aataaagttc tcttcaatat gttcaaaaaa  1140
atcctgtatg ccttactgag ggattgttca tttaaaggct acaggctat cagatgtgca  1200 accgagggcg ccagtcagat gaatactggc atggttaaca cagaaaaagc gaagatcgaa  1260
```

```
aagaaaatag agcaattaat aactcagcaa cggtttctgg atttcataat gcaacaaaca    1320
gaaaaccaga aaaagataga acaaaaacgc ttagaggagc tttataaggg gagcggtgcc    1380
gcgcttagag atgtattaga taccattgat cactatagta gcgttcaggc gagaatagct    1440
ggctatcgcg cttaa                                                    1455
```

<210> SEQ ID NO 24
<211> LENGTH: 484
<212> TYPE: PRT
<213> ORGANISM: Salmonella typhimurium

<400> SEQUENCE: 24

```
Met Asn Arg Ile His Ser Asn Ser Asp Ser Ala Ala Gly Val Thr Ala
1               5                   10                  15

Leu Thr His His His Leu Ser Asn Val Ser Cys Val Ser Ser Gly Ser
            20                  25                  30

Leu Gly Lys Arg Gln His Arg Val Asn Ser Thr Phe Gly Asp Gly Asn
        35                  40                  45

Ala Ala Cys Leu Leu Ser Gly Lys Ile Ser Leu Gln Glu Ala Ser Asn
    50                  55                  60

Ala Leu Lys Gln Leu Leu Asp Ala Val Pro Gly Asn His Lys Arg Pro
65                  70                  75                  80

Ser Leu Pro Asp Phe Leu Gln Thr Asn Pro Ala Val Leu Ser Met Met
                85                  90                  95

Met Thr Ser Leu Ile Leu Asn Val Phe Gly Asn Asn Ala Gln Ser Leu
            100                 105                 110

Cys Gln Gln Leu Glu Arg Ala Thr Glu Val Gln Asn Ala Leu Arg Asn
        115                 120                 125

Lys Gln Val Lys Glu Tyr Gln Glu Gln Ile Gln Lys Ala Ile Glu Gln
    130                 135                 140

Glu Asp Lys Ala Arg Lys Ala Gly Ile Phe Gly Ala Ile Phe Asp Trp
145                 150                 155                 160

Ile Thr Gly Ile Phe Glu Thr Val Ile Gly Ala Leu Lys Val Val Glu
                165                 170                 175

Gly Phe Leu Ser Gly Asn Pro Ala Glu Met Ala Ser Gly Val Ala Tyr
            180                 185                 190

Met Ala Ala Gly Cys Ala Gly Met Val Lys Ala Gly Ala Glu Thr Ala
        195                 200                 205

Met Met Cys Gly Ala Asp His Asp Thr Cys Gln Ala Ile Ile Asp Val
    210                 215                 220

Thr Ser Lys Ile Gln Phe Gly Cys Glu Ala Val Ala Leu Ala Leu Asp
225                 230                 235                 240

Val Phe Gln Ile Gly Arg Ala Phe Met Ala Thr Arg Gly Leu Ser Gly
                245                 250                 255

Ala Ala Ala Lys Val Leu Asp Ser Gly Phe Gly Glu Glu Val Val Glu
            260                 265                 270

Arg Met Val Gly Ala Gly Glu Ala Glu Ile Glu Glu Leu Ala Glu Lys
        275                 280                 285

Phe Gly Glu Glu Val Ser Glu Ser Phe Ser Lys Gln Phe Glu Pro Leu
    290                 295                 300

Glu Arg Glu Met Ala Met Ala Asn Glu Met Ala Glu Ala Ala Glu
305                 310                 315                 320

Phe Ser Arg Asn Val Glu Asn Asn Met Thr Arg Ser Ala Gly Lys Ser
                325                 330                 335
```

```
Phe Thr Lys Glu Gly Val Lys Ala Met Ala Lys Glu Ala Ala Lys Glu
                340                 345                 350

Ala Leu Glu Lys Cys Val Gln Glu Gly Gly Lys Phe Leu Leu Lys Lys
            355                 360                 365

Phe Arg Asn Lys Val Leu Phe Asn Met Phe Lys Lys Ile Leu Tyr Ala
        370                 375                 380

Leu Leu Arg Asp Cys Ser Phe Lys Gly Leu Gln Ala Ile Arg Cys Ala
385                 390                 395                 400

Thr Glu Gly Ala Ser Gln Met Asn Thr Gly Met Val Asn Thr Glu Lys
                405                 410                 415

Ala Lys Ile Glu Lys Lys Ile Glu Gln Leu Ile Thr Gln Arg Phe
            420                 425                 430

Leu Asp Phe Ile Met Gln Gln Thr Glu Asn Gln Lys Lys Ile Glu Gln
            435                 440                 445

Lys Arg Leu Glu Glu Leu Tyr Lys Gly Ser Gly Ala Ala Leu Arg Asp
        450                 455                 460

Val Leu Asp Thr Ile Asp His Tyr Ser Ser Val Gln Ala Arg Ile Ala
465                 470                 475                 480

Gly Tyr Arg Ala

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Tyr Gly Gly Arg Gly Asp Thr Pro
1               5
```

USE OF THE SALMONELLA SPP TYPE III SECRETION PROTEINS AS A PROTECTIVE VACCINATION

CROSS REFERENCE TO RELATED APPLICATIONS

In accordance with 37 C.F.R. § 1.76, a claim of priority is included in an Application Data Sheet filed concurrently herewith. The present application is a continuation of U.S. patent application Ser. No. 15/950,735, filed Apr. 11, 2018, which is a continuation in part application of U.S. patent application Ser. No. 15/013,454, filed Feb. 2, 2016, now U.S. Pat. No. 9,950,053, issued Apr. 24, 2018, which is a continuation in part application of U.S. patent application Ser. No. 14/437,535 filed Apr. 22, 2015, now abandoned, which is a 35 U.S.C. § 371 U.S. National stage application of PCT/US2013/66105 filed Oct. 22, 2013 which claims priority to U.S. Provisional application No. 61/716,911 filed Oct. 22, 2012, the complete disclosures of which are herein incorporated by reference.

FIELD OF THE INVENTION

The invention generally relates to protecting against *Salmonella*-type pathogens and, more particularly, to compositions and methods for immunizing against infection by typhoidal and non-typhoidal *Salmonella* serovars.

BACKGROUND

*Salmonella* is a genus of over 2000 serovars and includes organisms that cause a wide range of human and animal diseases. For example, *Salmonella enterica* serovars Typhi and Paratyphi A and B cause enteric ("typhoid") fever. *Salmonella enterica* serovars Typhimurium and Enteritidis are known as the non-typhoidal *Salmonella* (NTS) and cause salmonellosis—a gastroenteritis which is usually a self-limiting illness in healthy individuals.

As is the case with many gram-negative pathogens, *Salmonella* spp. use type III secretion systems (T3SSs) as virulence factors to deliver proteins into host cells and to subsequently cause/induce infection. The T3SS is a molecular "syringe and needle" apparatus, also known as a "type III secretion apparatus" (T3SA) which promotes uptake of the bacterium by the host cell, and then adaptation of the intracellular environment of the host cell to allow a productive infection. Salmonella has two functionally distinct T3SS's which are encoded by *Salmonella* "pathogenicity islands" 1 and 2 (SPI-1 and -2). The SPI-1 T3SS is central to the ability of *Salmonella* to invade nonphagocytic cells via the injection, from the bacteria and into the cell by way of the T3SA conduit, effector proteins which trigger extensive actin rearrangements on the surface of host cells. While this allows ingress of the pathogen into the host cell, a second T3SS island, SPI-2, is essential for bacterial replication/proliferation inside host cells. Upon intracellular activation of SPI-2, the bacteria proliferate within membrane-bound vacuoles of phagocytic eukaryotic cells (*Salmonella*-containing vacuoles, SCVs), with macrophages being the main cell type supporting bacterial growth in vivo. Bacterial effector proteins are translocated across the vacuolar membrane via the SPI-2 T3SS apparatus and into the host endomembrane system and cytoplasm, causing systemic disease.

The *Salmonella* NTS serotypes are a primary cause of foodborne illnesses worldwide. In the U.S. NTS are a leading cause of hospitalization and death due to foodborne illnesses, with *Salmonella enterica* serovar Typhimurium being the most frequent cause. 95% of the total cases of NTS are caused by contaminated food. Unfortunately, absolute protection from infection by enhanced agricultural surveillance is not feasible. Vaccines against these pathogens could provide a major weapon in controlling this disease. However, although some progress has been made in recent years, vaccines against *Salmonella* spp. have not proven to be broadly protective, and almost all are entirely directed only to the typhoid causing serovars. A *Salmonella* serotype-independent subunit vaccine that could target both typhoid and NTS serovars would be of tremendous public health value.

SUMMARY

Proteins associated with the tip of the T3SA in both SPI-1 and SPI-2 are extracellular, and thus are excellent candidates for the development of broadly protective serotype-independent subunit vaccines against *Salmonella*. Herein, the successful use of extracellular SPI-1 and SPI-2 proteins to immunize mammals against the effects of *Salmonella* infection is shown. Accordingly, compositions (e.g. immunogenic compositions) comprising one or more of the SPI-1 and SPI-2 proteins, or immunogenic fragments thereof, are provided, as are methods of using the compositions to elicit an immune response in and/or to vaccinate a mammal. Advantageously, in some aspects the methods and compositions provide broad serovar-independent protection against infection by both typhoid and NTS *Salmonella* serovars.

In one aspect, the invention provides methods of eliciting an immune response against at least one *Salmonella* serovar in a subject in need thereof. The methods comprise the steps of administering to the subject a composition comprising i) at least one *Salmonella* pathogenicity island 1 (SPI-1) and/or *Salmonella* pathogenicity island 2 (SPI-2) extracellular protein; and ii) a physiologically acceptable carrier; wherein said composition is administered in an amount so as to elicit an immune response to the at least one *Salmonella* serovar in said subject. In some aspects, the composition further comprises an adjuvant. In other aspects, the composition comprises an extracellular protein selected from the group consisting of: SipD, SipB, SseB and SseC. For example, the composition may comprise SipD and SipB; and the composition may further comprise SseB. In some aspects, the *Salmonella* serovar is *Salmonella enterica* serovar. In further aspects, the at least one *Salmonella enterica* serovar may be: typhoid serovar Typhi, typhoid serovar Paratyphi A, typhoid serovar Paratyphi B, non-typhoidal serovar Typhimurium and non-typhoidal serovar Enteritidis. In additional aspects, the subject is selected from a human and an agricultural animal, with exemplary agricultural animals including cattle, poultry, swine, horses, sheep and goats.

In other aspects, the invention provides immunogenic compositions comprising i) at least one *Salmonella* pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB.

In other aspects of the invention, what is provided are methods of treating or preventing *Salmonella* infection by one or both of a typhoid *Salmonella* serovar and a non-typhoid *Salmonella* serovar in a subject in need thereof. The methods comprise administering to the subject an amount of a composition comprising i) at least one *Salmonella* pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amounts that are administered are sufficient to treat or prevent said *Salmonella* infection in said subject.

In yet other aspects, the invention provides methods of lessening the severity of symptoms of *Salmonella* infection in a subject in need thereof, comprising administering to the subject an amount of a composition comprising i) at least one *Salmonella* pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amounts that are administered are sufficient to lessen the severity of said symptoms in said subject.

In additional aspects, the invention provides methods of decreasing fecal shedding of *Salmonella* from a subject who is or is likely to be infected with *Salmonella*, comprising administering to the subject an amount of a composition comprising i) at least one Salmonella pathogenicity island 1 (SPI-1) and/or *Salmonella* pathogenicity island 2 (SPI-2) extracellular protein; and ii) a physiologically acceptable carrier. In some aspects, the immunogenic composition further comprises an adjuvant. In further aspects, the at least one SPI-1 and/or SPI-2 extracellular protein is SipD, SipB, SseB or SseC. In some aspects, the at least one SPI-1 and/or SPI-2 extracellular proteins in the immunogenic compositions include SipD and SipB. In other aspects, the immunogenic compositions further comprise SseB. The amount that is administered is sufficient to lessen the severity of said symptoms in said subject.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

BRIEF DESCRIPTION OF THE DRAWINGS

Other objects and advantages of the invention will become apparent upon reading the following detailed description and upon reference to the drawings in which:

FIGS. 5A and B: number of SipB specific ASCs in spleens of immunized mice at days 42 and 56, respectively; FIGS. 5C and 5D: number of SipD specific ASCs at days 42 and 56, respectively; FIGS. 5E and 5F: number of SseB specific ASCs at days 42 and 56, respectively.

FIG. 6A: SipB specific IgG; FIG. 6B: SipD specific IgG; FIG. 6C: SseB specific IgG.

FIGS. 10A and 10B. Antibody titers of calves immunized as described in Example 3, on day 56 post-immunization. FIG. 10A: serum IgG; FIG. 10B: saliva IgA.

FIGS. 11A and 11B. Bacterial shedding in response to challenge with *S. enterica* Newport (FIG. 11A) or *S. enterica* Typhimurium (FIG. 11B) in calves on day 56 post-immunization.

FIGS. 12A-12F. Sequences of proteins of interest and nucleic acid sequence encoding them. FIG. 12A: amino acid sequence of SipB (SEQ ID NO: 1); FIG. 12B: nucleic acid sequence encoding SipB (SEQ ID NO: 2); FIG. 12C: amino acid sequence of SipD (SEQ ID NO: 3); FIG. 12D: nucleic acid sequence encoding SipD (SEQ ID NO: 4); FIG. 12E: amino acid sequence of SseB (SEQ ID NO: 5); FIG. 12F: nucleic acid sequence encoding SseB (SEQ ID NO: 6).

FIGS. 13A and 13B. FIG. 13A: Amino acid; and FIG. 13B: encoding nucleic acid sequences of SipD-SipB chimera (SEQ ID NOS: 7 and 8, respectively).

DETAILED DESCRIPTION

Figure 1:
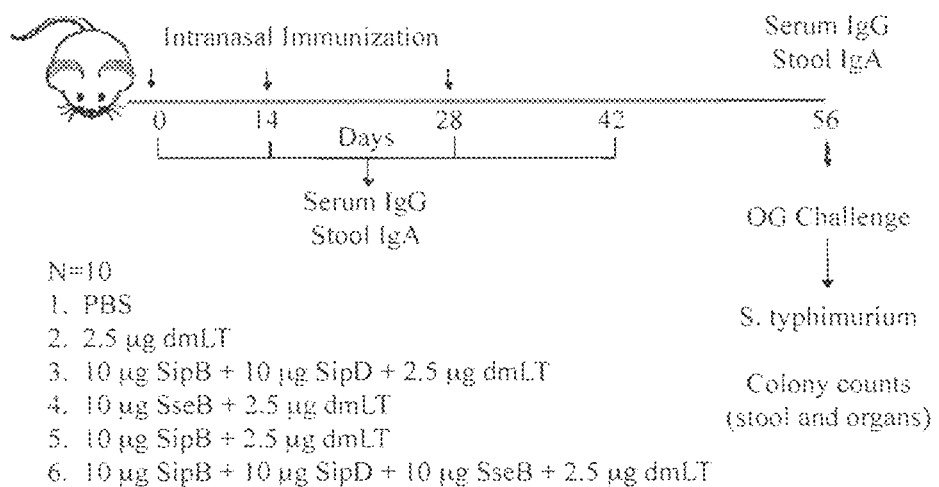
FIG. 1. Schematic illustration of the mouse testing protocol for Example 1.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Thus, for example, reference to a "serovar" includes reference to one or more of such serovars, unless otherwise specified. The use of plural terms is also not intended to be limiting, unless otherwise specified. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed. The recitation of numerical ranges by endpoints includes all numbers within that range (e.g., 1 to 5 includes 1, 1.5, 2, 2.75, 3, 3.80, 4, and 5).

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this specification, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range also is intended to include subranges such as 26 to 100, 27 to 100, etc., 25 to 99, 25 to 98, etc., as well as any other possible combination of lower and upper values within the stated range, e.g., 33-47, 60-97, 41-45, 28-96, etc. Note that integer range values have been used in this paragraph for purposes of illustration only and decimal ranges (e.g., 46.7-91.3) should also be understood to be intended as a possibility unless specifically excluded.

As used herein, a "chimeric" molecule is one which comprises one or more unrelated types of components, moieties or two or more chemically distinct regions which can be conjugated to each other, fused, linked, transcribed, translated, attached via a linker, chemically synthesized, expressed from a nucleic acid sequence, etc. For example, a fusion gene, a peptide and a nucleic acid sequence, a peptide and a detectable label, two or more peptide sequences, two or more nucleic acid sequences (e.g. from different regions of a genome, nucleic acid sequences not found contiguous in nature, fusion genes) and the like. As used herein, a "fusion gene" is a gene created by removing the stop protein from the sequence of a gene and attaching the DNA sequence of a second gene to the first. By fusing one nucleotide sequence to another, the host cell will express the sequences together, as a single fused protein. Fusion genes may contain two or more fused genes. Accordingly, "fusion protein" as used herein is a protein produced by expression of a fusion gene or two or more proteins fused or connected by any method. The term encompasses peptides, mutants, derivatives and any variants.

As used herein, the terms "conjugated," "linked," "attached," "fused" and "tethered," when used with respect to two or more moieties, means that the moieties or domains are physically associated or connected with one another, either directly or via one or more additional moieties that serve as a linking agent, to form a structure that is sufficiently stable so that the moieties remain physically associated under the conditions in which the structure is used, e.g., physiological conditions. The linkage can be based on genetic fusion according to the methods known in the art and described herein or can be performed by, e.g., chemical cross-linking. The additional domain present in the construct may be linked by a flexible linker, such as a polypeptide linker to one of the binding site domains; the polypeptide linker can comprise plural, hydrophilic or peptide-bonded amino acids of a length sufficient to span the distance between the C-terminal end of one of the domains and the N-terminal end of the other of the domains when the polypeptide assumes a conformation suitable for binding when disposed in aqueous solution. The term "connected" will be used for the sake of brevity and is meant to include all possible methods of physically associating each domain of the chimeric molecule to each other.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized ("derivatives"), such as by glycosylation, acetylation, phosphorylation, and the like.

As used herein, "variants" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The terms "nucleic acid sequence", "polynucleotide," and "gene" are used interchangeably throughout the specification and includes linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. The nucleic acid sequences may be composed of different regions. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in a nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

The term "*Salmonella*" is meant to include all Salmonella species and subspecies, including both typhoidal and non-typhoidal species, and all *S. enterica* subspecies.

The terms "*Salmonella* pathogenicity island 1 (SPI-1)" and "*Salmonella* pathogenicity island 2 (SPI-2)" is meant to include all of the genes encoded by SPI-1 and SPI-2 respectively. Reference to each of the molecules embodied herein, is meant to include, without limitation, nucleic acids, polynucleotides, oligonucleotides, peptides, polypeptides, proteins, homologous and/or orthologous molecules, mutants, variants, alleles, different species, and active fragments thereof. Accordingly, the terms "SPI-1", "SPI-2", "SipD", "SipB", "SicA", "SseB", "SseC", "SscA" etc., includes, for each of these molecules: nucleic acids, polynucleotides, oligonucleotides, peptides, polypeptides, proteins, homologous and/or orthologous molecules, mutants, variants, alleles, different species, and active fragments thereof.

"Vaccine" as used herein is a preparation that stimulates an immune response that produces immunity against particular antigens, e.g. *Salmonella* serotypes or serovars. Vaccines may be used to prevent infection, to create resistance to an infection or to ameliorate the effects of infection. Vaccines may contain, but are not limited to, live, attenuated infectious material such as viruses or bacteria, and dead or inactivated organisms or purified products derived therefrom. A vaccine can be administered by injection, orally or by inhalation. Injection may be, but are not limited to, subcutaneous (sc), intramuscular (im), intraperitoneal (ip), intradermal (id) or intravenous (iv).

As used herein, the terms "elicit an immune response", "induces or enhances an immune response", or "stimulates an immune response" are used interchangeably herein, and refer to a statistically measurable induction or increase in an immune response over a control sample to which the peptide, polypeptide or protein has not been administered.

Preferably the induction or enhancement of the immune response results in a prophylactic or therapeutic response in a subject. The subject mounts one or both of an innate and/or an adaptive immune reaction against antigenic determinants of the proteins or antigenic portions thereof that are administered. In particular, the adaptive immune reaction entails production of e.g. B and T cell lymphocytes and antibodies specific for binding and forming complexes with the antigenic determinants. In some embodiments, the proteins and/or antigenic fragments thereof elicit a protective immune response in the subject, i.e. administration of one or more of the proteins and/or antigenic portions thereof results in an immune response that is protective against later challenge by the disease causing organism itself, either preventing infection altogether, or lessening the impact of infection by decreasing disease symptoms that would otherwise occur, had the subject not been vaccinated as described herein. The compositions embodied herein, induce immune responses to all *Salmonella* serovars and include typhoidal and non-typhoidal serovars as well as Salmonella subspecies.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

The term "immunoregulatory" is meant a vaccine, composition or substance that is immunogenic (i.e. stimulates or increases an immune response) or immunosuppressive (i.e. reduces or suppresses an immune response).

"Immunogen" or "antigen" as used herein is a substance that is foreign to the body that stimulates an immune response, such as the production of antibodies when introduced into the body. Immunogens or antigens are also capable of reacting with the products of an immune response. Immunogens or antigens may include, but are not limited to proteins or polypeptides, enzymes, toxins, bacteria, viruses, foreign tissues, foreign blood cells, and the cells of transplanted organs. Correspondingly, "immunogenicity" is the ability of an immunogen or antigen to stimulate an immune response. In the context of this invention, an "antigen" or "antigenic" composition or "immunogen" include without limitation any SPI-1 and/or SPI-2 molecules comprising proteins, polypeptides, peptides, polynucleotides, oligonucleotides, fragments, derivatives or variants thereof. Accordingly, an antigen includes the chimeric molecules comprising SipD, SipB, SseB or SseC proteins, polypeptides, peptides, polynucleotides, oligonucleotides, fragments, derivatives or variants thereof, as embodied herein.

"Cells of the immune system" or "immune cells", is meant to include any cells of the immune system that may be assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response selective for the antigen. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"Immune related molecules" refers to any molecule identified in any immune cell, whether in a resting ("non-stimulated") or activated state, and includes any receptor, ligand, cell surface molecules, nucleic acid molecules, polypeptides, variants and fragments thereof.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

A "secondary immune response" or "adaptive immune response" may be active or passive, and may be humoral (antibody based) or cellular that is established during the life of an animal, is specific for an inducing antigen, and is marked by an enhanced immune response on repeated encounters with said antigen. A key feature of the T lymphocytes of the adaptive immune system is their ability to detect minute concentrations of pathogen-derived peptides presented by MHC molecules on the cell surface.

"Antibody" or "immunoglobulin," as used herein is a protein produced by the immune system that helps destroy disease-causing organisms. Antibodies are made and secreted by B lymphocytes in response to stimulation by antigens, which may include vaccines. Antibodies are generally specific, binding only to the specific antigen that stimulated its production. A given antigen can have many epitopes, each one reacting with the immune system to create antibodies specific for each of the epitopes. Antibodies can be effective defenders against both bacteria and viruses, in addition to toxins. Antibodies can be polyclonal or monoclonal.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to an animal, such as a mammalian subject to be treated, with human patients being preferred, or a companion or domesticated or food-or feed-producing or livestock or game or racing or sport animal, for instance, a cow, a horse, a dog, a cat, a goat, a sheep or a pig, or fowl such as chickens, duck, turkey or any other organism which can benefit from the treatments embodied herein. In some cases, the methods of the invention find use in experimental animals, in veterinary application, and in the development of animal models for disease, including but not limited to, rodents including mice, rats, and hamsters; and primates.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As defined herein, an "effective" amount of a compound or agent (i.e., an effective dosage) means an amount sufficient to produce a (e.g., clinically) desirable result. Accordingly, an "efficacious" vaccine comprises a therapeutically effective amount of a given antigen.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

General Techniques

For further elaboration of general techniques useful in the practice of this invention, the practitioner can refer to standard textbooks and reviews in cell biology, microbiology, bacteriology, molecular biology, tissue culture, and physiology.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Some reagents, cloning vectors, and kits for genetic manipulation referred to in this disclosure are available from commercial vendors. For example, such as BioRad, Stratagene, Invitrogen, Sigma-Aldrich, and ClonTech.

Compositions

A vaccine that prevents colonization of Salmonella in deeper tissues (i.e. lymph nodes) reduces the risk of introducing this broad host-range pathogen from contaminating food products going into the market. The result is a safe source of protein that is important for consumer nutrition. Animal protein is an important component of a balanced diet for children in the United States. Children tend to be some of the hardest hit when *Salmonella* outbreaks occur. Their immune system is still developing and they have not been exposed to the variety of immunogens that boost that system. Foods in the meat category, such as, hamburgers, chicken and deli meats are the foods most likely to be contaminated with *Salmonella*. *Salmonella* has also been associated with dairy, plants, fruits and vegetables, such as, spinach, lettuce, tomatoes, cantaloupe and the like; and, processed foods such as peanut butter, ice cream, and the like.

The surface-exposed proteins at the tip of the two type III secretion (TTS) apparatus needles of *Salmonella* (both SPI-1 and SPI-2), as described herein for the development of vaccines, are protective against all *S. enterica* subspecies, as disclosed in detail in the examples section which follows. These include, but are not limited to: the initial tip protein SipD and the first 'translocator' protein SipB from *Salmonella* pathogenicity island-1 (SPI-1). Without being bound by theory, it is believed that disruption of the function of SPI-1 (e.g. by antibody binding to one or more of these proteins) prevents *Salmonella* protein delivery to host cells and thus blocks bacterial effects on the host cell. In addition, after entry into the cell, the proteins from SPI-2 are expressed and are surface exposed, and these proteins, which include but are not limited to: SseB and SseC, also provide vaccine targets. Without being bound by theory, it is believed that disruption of the SPI-2 apparatus (e.g. by antibody binding to one or more of these proteins) prevents successful replication of the bacteria within the host, and also blocks spread of the bacteria within the host, preventing systemic infection.

The present invention provides compositions for use in eliciting an immune response and/or vaccinating an individual against *Salmonella* infection, and/or against disease symptoms caused by *Salmonella* infection. The compositions include one or more substantially purified proteins, polypeptides or antigenic regions thereof as described herein, or substantially purified nucleic acid sequences (e.g. DNA cDNA, RNA, etc.) encoding such proteins, polypeptides or antigenic regions thereof, and a pharmacologically suitable/compatible carrier. By "substantially purified" it is meant that the molecule is largely free of other organic molecules, cellular debris, solvents, etc. when tested using standard techniques known to those of skill in the art (e.g. gel electrophoresis, column chromatography, sequencing, mass spectroscopy, etc.). For example, the molecule is generally at least about 50, 55, 60, 65, 70, or 75% pure by wt/%, and preferably is at least about 80, 85, 90, 95% or more pure (e.g. 96, 97, 98, 99 or even 100% pure). The preparation of proteins, polypeptides, and peptides as described herein is well-known to those in the art, and includes, for example, recombinant preparation; isolation from a natural source; chemical synthesis; etc. The purification of proteinaceous materials is also known. However, specific exemplary methods for preparing the vaccinating agents utilized in the practice of the invention are described in detail in the Examples section below.

Accordingly, proteins which make up SPI-1 and/or the SPI-2 of *Salmonella*, or antigenic portions thereof, are used to elicit an immune response in subjects to whom they are administered.

Exemplary proteins which may be used in the practice of the invention include but are not limited to: SipD, SipB, SseB and SseC, which may be administered alone or in various forms and combinations as described herein. Exemplary full length sequences of SipD, SipB, and SseB and nucleic acids that encode them are provided in FIGS. 12A-12F (SEQ ID NOS: 1-6). The phrase(s) "SipD, SipB, SseB and SseC protein(s)" as used herein refer to both the full length proteins as depicted in the figures, to antigenic regions (portions, fragments, etc.), derivatives, or variants thereof.

The proteins, polypeptides/peptides, polynucleotides, oligonucleotides, derivatives or variants thereof, which may be used in the practice of the invention include sequences which have at least about 50, 55, 60, 65, 70, 75, 80, 85, or 90% identity to the sequences comprising SEQ ID NOS: 1-8, 13-16, or 23-24, or to sections of those sequences which correspond to antigenic regions. Typically, the level of identity is at least about 92, 93, 94, 95, 96, 97, 98 or 99%. Those of skill in the art are familiar with methods and software programs for sequence comparison to determine identity.

The proteins, polypeptides/peptides, polynucleotides, oligonucleotides, derivatives or variants thereof, which may be used in the practice of the invention, include SipD, SipB, SseB and SseC, which have at least about 50, 55, 60, 65, 70, 75, 80, 85, or 90% identity to the sequences presented herein, or to sections of those sequences which correspond to antigenic regions. Typically, the level of identity is at least about 92, 93, 94, 95, 96, 97, 98 or 99%. Those of skill in the art are familiar with methods and software programs for sequence comparison to determine identity.

The invention also encompasses the use of nucleic acids encoding the proteins/polypeptides/peptides, chimeric molecules described herein, i.e. nucleic acid vaccines are also contemplated, as are vectors for producing the proteins. Exemplary nucleic acid sequences encoding e.g. SipD, SipB, and SseB are presented in FIGS. 12B, 12D and 12F (SEQ ID NOS: 2, 4 and 6, respectively). An exemplary nucleic acid sequence encoding e.g. SipD-SipB and SseB-SseC chimeric molecules comprise SEQ ID NOS: 13 and 15 respectively, However, those of skill in the art will appreciate that the genetic code is redundant and that many sequences may encode a given amino acid sequence. All nucleic acid sequences (e.g. DNA, RNA, cDNA, DNA/RNA hybrids, etc.) which successfully encode and express the proteins/polypeptides/peptides described herein may be used in the practice of the invention, so long as administration results in elicitation of an immune response (e.g. a protective immune response) as described herein.

In some embodiments of the invention, the proteins, polypeptides or peptides that are used in the vaccine are chimeric or fusion proteins. The chimeric protein is translated from a single, contiguous nucleic acid molecule, and which comprises sequences from at least two different proteins or antigenic regions thereof. For example, a chimera of the invention may include two or more of SipD, SipB, SseB and SseC, or antigenic regions of two or more of these. Typically, the individual sequences are joined via a linker or spacer sequence of e.g. from about 2 to about 20 amino acids, usually from about 2 to about 10 amino acids. The amino acids in linking sequences are typically uncharged and the linker sequence usually does not exhibit secondary or tertiary structure, but does allow the fused protein/peptide segments to adopt functional secondary, tertiary, etc. conformations. One such exemplary chimera includes SipB and SipD. The amino acid sequence of this chimera is shown in FIG. 13A (SEQ ID NO: 7). The chimera may be encoded by any suitable nucleic acid sequence, e.g. the exemplary nucleic acid sequence depicted in FIG. 13B (SEQ ID NO: 8). In one embodiment the chimeric peptide is SEQ ID NOS: 14 or 16.

In some embodiments, the compositions of the invention comprise one or more molecules having at least about 60% sequence identity to SEQ ID NOS: 1-8, 13-16, or 23-24. In some embodiments, the compositions of the invention comprise one or more molecules of SEQ ID NOS: 1-8, 13-16, or 23-24. In some embodiments, the compositions of the invention comprise one or more molecules of SEQ ID NOS: 1-8, 13-16, or 23-24 proteins, polypeptides, peptides, polynucleotides, oligonucleotides, fragments, derivatives or variants thereof.

In an embodiment, a vaccine comprises a therapeutically effective amount of a chimeric molecule, the chimeric molecule comprising at least one *Salmonella* pathogenicity island 1 (SPI-1) and/or *Salmonella* pathogenicity island 2 (SPI-2) molecule or variants thereof. In embodiments, the SPI-1 and/or SPI-2 molecules comprise proteins, polypeptides, peptides, polynucleotides, oligonucleotides, fragments, derivatives or variants thereof. In other embodiments, the chimeric molecule comprises SipD, SipB, SseB or SseC proteins, polypeptides, peptides, polynucleotides, oligonucleotides, fragments, derivatives or variants thereof. In one embodiment, the chimeric molecule comprises a SipD protein, peptide, derivative or variants thereof connected to a SipB protein, peptide, derivative or variants thereof. In another embodiment, the chimeric molecule comprises an SseB protein, peptide, derivative or variants thereof, connected to an SseC protein, peptide or variants thereof. The vaccine can be formulated in a pharmaceutically acceptable carrier and/or an adjuvant. Alternatively, the adjuvant may be administered separately.

In another embodiment, the vaccine comprises a therapeutically effective amount of a chimeric molecule comprising a SipD protein, peptide, derivative or variants thereof connected to a SipB protein, peptide, derivative or variants thereof; and, a therapeutically effective amount of a chimeric molecule comprising an SseB protein, peptide or variants thereof, connected to an SseC protein, peptide, derivative or variants thereof. In another embodiment, the vaccine comprises a therapeutically effective amount of a chimeric molecule comprising a SipD protein, peptide, derivative or variants thereof connected to at least one of: a SipB, and/or an SseB, and/or an SseC, protein, peptide, derivative or variants thereof.

In another embodiment, the vaccine comprises a therapeutically effective amount of a chimeric molecule comprising a SipB protein, peptide, derivative or variants thereof connected to at least one of: a SipD, and/or an SseB, and/or an SseC, protein, peptide, derivative or variants thereof.

In another embodiment, the vaccine comprises a therapeutically effective amount of a chimeric molecule comprising an SseB protein, peptide, derivative or variants thereof connected to at least one of: a SipB, and/or SipD, and/or an SseC, protein, peptide, derivative or variants thereof.

In another embodiment, the vaccine comprises a therapeutically effective amount of a chimeric molecule comprising an SseC protein, peptide, derivative or variants thereof connected to at least one of: a SipB, and/or a SipD, and/or an SseB, protein, peptide, derivative or variants thereof.

In yet another embodiment, the vaccine comprises a therapeutically effective amount of one or more of: a SipB, a SipD, an SseB, an SseC, proteins, peptides, derivatives or variants thereof. The different molecules can be combined in doses over a period of time, administered separately or in any combination as determined by a health professional based on the severity of disease, age, sex or health of the subject.

In yet another embodiment, the vaccine comprises a therapeutically effective amount of SipB proteins, peptides, derivatives or variants thereof.

In yet another embodiment, the vaccine comprises a therapeutically effective amount of SipD proteins, peptides, derivatives or variants thereof.

In yet another embodiment, the vaccine comprises a therapeutically effective amount of SseB proteins, peptides, derivatives or variants thereof.

In yet another embodiment, the vaccine comprises a therapeutically effective amount of SseC proteins, peptides, derivatives or variants thereof.

In another embodiment, the vaccine comprises an expression vector encoding one or more molecules comprising at least one *Salmonella* pathogenicity island 1 (SPI-1) and/or *Salmonella* pathogenicity island 2 (SPI-2) molecules, derivatives or variants thereof. In embodiments, the expression vector encodes for at least one of SipD, SipB, SseB or SseC proteins, fragments, derivatives, variants or any combinations thereof. In one embodiment, the expression vector encodes for a SipD protein, peptide, derivative or variants thereof connected to a SipB protein, peptide, derivative or variants thereof. In another embodiment, the expression vector encodes for an SseB protein, peptide, derivative or variants thereof, connected to an SseC protein, peptide or variants thereof.

In another embodiment, the vaccine comprises an expression vector encoding a chimeric molecule comprising a SipB protein, peptide, derivative or variants thereof connected to at least one of: a SipD, and/or an SseB, and/or an SseC protein, peptide, derivative or variants thereof.

In another embodiment, the vaccine comprises an expression vector encoding a chimeric molecule comprising an SseB protein, peptide, derivative or variants thereof connected to at least one of: a SipB, and/or SipD, and/or an SseC protein, peptide, derivative or variants thereof.

In another embodiment, the vaccine comprises an expression vector encoding a chimeric molecule comprising an SseC protein, peptide, derivative or variants thereof connected to at least one of: a SipB, and/or a SipD, and/or an SseB protein, peptide, derivative or variants thereof.

In yet another embodiment, the vaccine comprises an expression vector encoding one or more of: a SipB, a SipD, an SseB, an SseC protein, peptide, derivative or variants thereof.

In yet another embodiment, the vaccine comprises an expression vector encoding SipB proteins, peptides, derivatives or variants thereof.

In yet another embodiment, the vaccine comprises an expression vector encoding SipD proteins, peptides, derivatives or variants thereof.

In yet another embodiment, the vaccine comprises an expression vector encoding SseB proteins, peptides, derivatives or variants thereof.

In yet another embodiment, the vaccine comprises an expression vector encoding SseC proteins, peptides, derivatives or variants thereof.

In yet another embodiment, the vaccine comprises an expression vector comprising at least one of SEQ ID NOS: 1-8, 13-16, or 23-24.

In another embodiment, a chimeric molecule comprises at least one Salmonella pathogenicity island 1 (SPI-1) and/or Salmonella pathogenicity island 2 (SPI-2) protein, peptides, variants, derivatives or combinations thereof. In some embodiments, the SPI-1 proteins, peptides, derivatives or variants thereof, are SipD and SipB. In other embodiments, the SPI-2 protein, peptides, derivatives or variants thereof are SseB and SseC. In an embodiment, a chimeric molecule comprises a SipD protein, peptide, derivatives or variants thereof, connected to a SipB protein, peptide or variants thereof. In another embodiment, the chimeric molecule comprises an SseB protein, peptide, derivatives or variants thereof, connected to an SseC protein, peptide, derivatives or variants thereof.

In one embodiment, the chimeric molecule comprises a molecule having at about 50% sequence identity to SEQ ID NOS: 1-8, 13-16, or 23-24. In other embodiments the chimeric molecule comprises any one of SEQ ID NOS: 1-8, 13-16, or 23-24.

In yet another embodiment, a chimeric molecule comprises a nucleic acid sequence encoding at least one Salmonella pathogenicity island 1 (SPI-1) and/or Salmonella pathogenicity island 2 (SPI-2) protein, peptides, variants, derivatives or combinations thereof. In an embodiment, the SPI-1 nucleic acid sequence encodes for SipD and/or SipB proteins, peptides, derivatives or variants thereof. In another embodiment, the SPI-2 nucleic acid sequence encodes for SseB and/or SseC protein, peptides, derivatives or variants thereof.

In another embodiment, a chimeric molecule comprises a nucleic acid sequence encoding at least one Salmonella pathogenicity island 1 (SPI-1) and at least one Salmonella pathogenicity island 2 (SPI-2) protein, peptides, derivatives, variants or combinations thereof. Preferably, the SPI-1 and SPI-2 protein, peptides, derivatives or variants comprise SipD, SipB, SseB, or SseC.

In another embodiment, a vaccine formulation comprises a therapeutically effective amount of a first chimeric molecule and a second chimeric molecule in a pharmaceutically acceptable carrier, the first chimeric molecule comprising at least one Salmonella pathogenicity island 1 (SPI-1) molecule linked or connected to at least one SPI-1 molecule; the second chimeric molecule comprising at least one Salmonella pathogenicity island 2 (SPI-2) linked or connected to at least one SPI-2 molecule. In one embodiment, the at least one SPI-1 molecule is connected to an SPI-2 molecule.

In certain embodiments, the SPI-1 and/or SPI-2 molecules of the invention can be administered to cells as a single protein containing SipD, SipB, SseB, or SseC (or active domains thereof), separated by a cleavable linker. Examples of cleavable linkers are known in the art (see, e.g., U.S. Pat. Nos. 5,258,498 and 6,083,486.)

Modified polypeptides: The invention is not limited to wild type SPI-1 and SPI-2 molecules but includes without limitation, allelic variants, species variants, splicing variants, mutants, fragments, and the like.

In an embodiment, SPI-1 and SPI-2 includes the peptide itself, chemical equivalents thereto, isomers thereof (e.g., isomers, stereoisomers, retro isomers, retro-inverso isomers, all-[D] isomers, all-[L] isomers, or mixed [L] and [D] isomers thereof), conservative substitutions therein, precursor forms thereof, endoproteolytically-processed forms thereof, such as cleavage of single amino acids from N or C terminals or immunologically active metabolites of the peptides of the invention, pharmaceutically-acceptable salts and esters thereof, and other forms resulting from post-translational modification. Also included is any parent sequence, up to and including 10, 9, 8, 7, 6, 5 and 4 amino acids in length (cyclized, or linear, or branched from the core parent sequence), for which the specified sequence is a subsequence. A person skilled in the art would appreciate that where the peptide can be a monomer, dimer, a trimer, etc. The uses of the peptides of the present invention include use of peptides wherein the active fragment or fragments are complexed to one or more binding partners. Modified peptides which retain the activity of the peptides of the invention are encompassed within the scope of the present invention.

In another embodiment, SPI-1 and SPI-2 peptides, or antigenic domains thereof, comprise at least one non-native amino acid residue or a non-amino acid molecule. A "non-native" amino acid residue comprises any change to an amino acid which is encoded by the SPI-1 and SPI-2 nucleic acid sequences. Thus, a non-native amino acid residue or non-amino acid molecule comprises, without limitation: a chemical equivalent, analog, synthetic molecule, derivative, variant, substitution, peptide nucleic acid, a linker molecule, inorganic molecule etc.

The mutations can be introduced at the nucleic acid level or at the amino acid level. With respect to particular nucleic acid sequences, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. If mutations at the nucleic acid level are introduced to encode a particular amino acid, then one or more nucleic acids are altered. For example proline is encoded by CCC, CCA, CCG, CCU; thus, one base change, e.g. CCC (proline) to GCC gives rise to alanine. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule or a different molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence, the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated, without user manipulation, into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

In some cases, the non-natural amino acid substitution(s) or incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, binding partner conformation modulators, dimer or multimer formation, no change to activity or property compared to the native molecule, or manipulating any physical or chemical property of the polypeptide such as solubility, aggregation, or stability. For example, locations in the polypeptide required for antigenicity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, www.rcsb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained. Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three dimensional crystal structure of a polypeptide with its associated ligand, receptor and/or binding proteins e.g. immunoglobulins, a preference for conservative substitutions As further used herein, a "chemical equivalent" of a peptide of the invention is a molecule which possesses the same desired activity, e.g. immunological activity, as peptides described herein, and exhibits a trivial chemical different, or a molecule which is converted, under mild conditions, into a peptide of the invention (e.g., esters, ethers, reduction products, and complexes of the peptides of the invention).

The term "analogue", as used herein, includes any peptide having an amino acid sequence substantially identical to a sequence described herein, in which at least one residue has been conservatively substituted with a functionally-similar residue. An "analogue" includes functional variants and obvious chemical equivalents of an amino acid sequence of SPI-1 and SPI-2 peptides, or functional domains thereof. As further used herein, the term "functional variant" refers to the activity of a peptide that demonstrates an ability to signal; interacting with one or more molecules; activating a transcription pathway, etc. An "analogue" further includes any pharmaceutically-acceptable salt of an analogue as described herein.

A "derivative", as used herein, refers to a peptide of the invention having one or more amino acids chemically derivatized by reaction of a functional side group. Exemplary derivatized molecules include, without limitation, peptide molecules in which free amino groups have been derivatized to form salts or amides, by adding acetyl groups, amine hydrochlorides, carbobenzoxy groups, chloroacetyl groups, formyl groups, p-toluene sulfonyl groups, or t-butyloxycarbonyl groups. Free hydroxyl groups may be derivatized to form O-acyl or O-alkyl derivatives. Furthermore, free carboxyl groups may be derivatized to form salts, esters (e.g., methyl and ethyl esters), or hydrazides. Thus, a "derivative" further includes any pharmaceutically-acceptable salt of a derivative as described herein.

The peptides embodied herein, can a modified C-terminus and/or a modified N-terminus. For example, an amidated C-terminus, the amino terminus can be acetylated (Ac) or the carboxy terminus can be amidated ($NH_2$). However, the peptides of the invention are preferably not acetylated if such a modification would result in loss of desired immunological activity. Amino terminus modifications include methylating (i.e., —$NHCH_3$ or —$NH(CH_3)_2$, acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

In one embodiment backbone substitutions can be made, such as NH to $NCH_3$. The SPI-1 and SPI-2 peptides may also be a modification (e.g., a point mutation, such as an insertion or a deletion, or a truncation). By way of example, the peptide may comprise an amino acid sequence comprising a modified residue by at least one point insertion of a D amino acid as long as desired immunogenicity is retained. In particular, proline analogs in which the ring size of the proline residue is changed from 5 members to 4, 6, or 7 members can be employed. Cyclic groups can be saturated or unsaturated, and if unsaturated, can be aromatic or non-aromatic.

In another embodiment, the naturally occurring side chains of the 20 genetically encoded amino acids (or D amino acids) are replaced with other side chains with similar properties, for instance with groups such as alkyl, lower alkyl, cyclic 4-, 5-, 6-, to 7-membered alkyl amide, amide lower alkyl amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine, Nlys; N-(4-aminobutyl)-glycine which has the lysine side chain attached to the "N-terminus" and compounds with aminopropyl or aminoethyl groups attached to the amino group of glycine. (2), Non-naturally occurring amino acids with no net charge and side-chains similar to arginine, such as, Cit; citrulline and Hci; citrulline with one more methylene group; (3) non-standard non-naturally occurring amino acids with OH (e.g., like serine), such as, hSer; homoserine (one more methylen group, Hyp; hydroxyproline, Val(βOH); hydroxyvaline, Pen; penicillamin, (Val(βSH); (4) proline derivatives, such as, D-Pro, such as, 3,4-dehydroproline, Pyr; pyroglutamine (proline with C=O in ring), Proline with fluorine substitutions on the ring, 1,3-thiazolidine-+carboxylic acid (proline with S in ring); (5) Histidine derivative, such as, Thi; beta-(2-thienyl)-alanine; or (6) alkyl derivatives, such as, Abu; 2-aminobutyric acid (ethyl group on Cα), Nva; norvaline (propyl group on Cα), Nle; norleucine (butyl group on Cα), Hol; homoleucine (propyl group on Cα), Aib, alpha-aminoisobutyric acid (valine without methylene group). A person skilled in the art would appreciate that those substitutions that retain the activity of the parent peptide/sequence.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

The peptides of the invention can be cyclized, or a desamino or descarboxy residue at the termini of the peptide can be incorporated, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

The peptides of the invention can be cyclized by adding an N and/or C terminal cysteine and cyclizing the peptide through disulfide linkages or other side chain interactions.

A desamino or descarboxy residue at the termini of the peptide can be incorporated, so that there is no terminal amino or carboxyl group, to decrease susceptibility to proteases or to restrict the conformation of the peptide.

Mutant polypeptides, e.g. SPI-1 and SPI-2, molecules comprising SipD, SipB, SseB or SseC or antigenic domains thereof, can be assessed in one or more of the assays described herein. The polypeptides can include amino acid residues (naturally occurring, synthetic, analogs, derivatives, or modified (e.g., glycosylated or phosphorylated residues) that are linked by a peptide bond.

In addition to containing one or more mutations, a polypeptide of the invention can be substantially pure (i.e., separated from one or more of the components that naturally accompany the polypeptide). Typically, a polypeptide is substantially pure when it is at least 60%, by weight, free from naturally occurring organic molecules. Alternatively, the preparation can be at least 75%, at least 90%, or at least 99%, by weight, of mutant polypeptide. A substantially pure mutant polypeptide can be obtained, for example, by expression of a recombinant nucleic acid encoding a mutant polypeptide, e.g. SipB, SipD, SseB or SseC, or by chemically synthesizing the polypeptide. Purity can be measured by any appropriate method, including column chromatography, polyacrylamide gel electrophoresis, or HPLC analysis. Polypeptides that are derived from eukaryotic organisms but synthesized in *E. coli*, or other prokaryotes, and polypeptides that are chemically synthesized will be substantially free from their naturally associated components.

A wild type SipD, SipB, SseB or SseC can be a polypeptide that is identical to the naturally-occurring SipD, SipB, SseB or SseC polypeptide. A mutant polypeptide can be a polypeptide or portion thereof having at least one mutation relative to the wild-type molecule.

Mutations in polypeptides can be effected in many following ways, for example: deletion of one or more of the amino acids, addition of one or more amino acids, or substitution of one or more of the amino acids. In the event the mutation is a substitution, the substitution can be a conservative or non-conservative substitution. Non-conservative substitutions occur when one amino acid residue in a polypeptide sequence is replaced by another amino acid that has a different physical property (e.g., a different size, charge, or polarity) as the amino acid being replaced. For example, substitution of a non-aromatic amino acid in the place of an aromatic amino acid (e.g., substitution of an alanine in the place of tryptophan) is an example of a non-conservative substitution. Alternately, the substitution can be a conservative amino acid substitution. A conservative substitution can be the replacement of one amino acid in a polypeptide sequence by another amino acid, wherein the replacement amino acid has similar physical properties (e.g., size, charge, and polarity) as the amino acid being replaced. For example, replacing one aromatic amino acid with another aromatic amino acid can be a conservative substitution. Some typical examples of conservative amino acid substitutions include substitutions with the following groups: glycine and alanine; valine, isoleucine, and leucine; aspartic acid and glutamic acid; asparagine and glutamine; serine and threonine; lysine and arginine; and phenylalanine and tyrosine. The substitution can be, for example, a non-aromatic amino acid substitution. The substitution can also be at the corresponding position of a polypeptide from another species (for example, a domesticated animal such as a cow, pig, sheep, rabbit, goat, dog or cat). The term "conservative substitutions", as defined herein, includes substitutions having an inconsequential effect on the ability of the peptide of the invention to enhance innate immunity.

The polypeptides described herein can include a heterologous (i.e., non-SipD, -SipB, -SseB or -SseC) sequence.

Polynucleotides: A mutant polypeptide, whether alone or as a part of a chimeric polypeptide, can be encoded by a nucleic acid molecule, and substantially pure nucleic acid molecules that encode the mutant polypeptides described herein are within the scope of the invention. The nucleic acid can be a molecule of genomic DNA, cDNA, synthetic DNA, or RNA. The nucleic acid molecule encoding, for example, a SipD, SipB, SseB or SseC polypeptide will be at least 65%, at least 75%, at least 85%, or at least 95% (e.g., 99%) identical to the nucleic acid encoding wild-type molecules. For nucleic acids, the length of comparison sequences will generally be at least 50 nucleotides, preferably at least 60 nucleotides, more preferably at least 75 nucleotides, and most preferably 10 nucleotides.

The polynucleotides e.g. SPI-1 and SPI-2 molecules comprising SipD, SipB, SseB or SseC can also comprise modifications. Examples of some modified polynucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified SPI-1 and SPI-2 polynucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N ($CH_3$)—$CH_2$, $CH_2$—N($CH_3$)—N($CH_3$)—$CH_2$ and O—N ($CH_3$)—$CH_2$—$CH_2$ backbones, wherein the native phosphodiester backbone is represented as O—P—O—CH). The amide backbones disclosed by De Mesmaeker et al. *Acc. Chem. Res.* 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Oligonucleotides may also have sugar mimetics such as cyclobutyls in place of the pentofuranosyl group.

Polynucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the polynucleotides of the invention involves chemically linking to the polynucleotide, one or more moieties or conjugates which enhance the activity or cellular uptake of the polynucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Polynucleotides comprising lipophilic moieties and methods for preparing such polynucleotides are known in the art, for example, U.S. Pat. Nos. 5,138,045, 5,218,105 and 5,459,255.

It is not necessary for all positions in a given polynucleotide to be uniformly modified, and in fact more than one of the aforementioned modifications may be incorporated in a single polynucleotide or even at within a single nucleoside within a polynucleotide. The present invention also includes polynucleotides which are chimeric polynucleotides as hereinbefore defined.

Vectors Expressing SPI-1 and/or SPI-2 Molecules

Also encompassed are vectors which contain such nucleic acid sequences (e.g. plasmids, cosmids, various expression vectors, etc.), and host cells such as bacteria, insect cells, etc., which comprise the nucleic acid sequences and/or the vectors. Such vectors typically include one or more expressible gene sequences encoding one or more or the proteins/polypeptides/peptides of interest, operably linked to at least one transcription element (e.g. a promoter) that drives expression of the gene. The vectors may be used for production of the proteins/fragments thereof, or may be used as a vaccinating agent, i.e. the invention also encompasses nucleic acid vaccines. Those of skill in the art are aware of the many protocols for preparing and administering nucleic acid vaccines, such as those described in issued U.S. Pat. Nos. 7,927,870 and 7,094,410, the complete contents of which are hereby incorporated by referenced in entirety. Sequence identity may be determined in various ways that are within the skill in the art, e.g., using publicly available computer software such as BLAST, BLAST-2, ALIGN or Megalign (DNASTAR) software, which are used to perform sequence alignments and then calculate sequence identity. Exemplary software programs available from the National Center for Biotechnology Information (NCBI) on the website ncbi.nlm.nih.gov include blastp, blastn, blastx, tblastn and tblastx. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are used at the default settings. The default scoring matrix used by blastp, blastx, tblastn, and tblastx is the BLOSUM62 matrix (Henikoff et al, (1992) *Proc. Natl. Acad. Sci.* USA 89: 10915-10919). In one approach, the percent identity can be determined using the default parameters of blastp, version 2.2.26 available from the NCBI.

In a preferred embodiment, an expression vector comprises a nucleic acid molecule with a sequence encoding polypeptides described herein. The vector can be capable of directing expression of a SipD, SipB, SseB or SseC polypeptide in, for example, a cell that has been transduced with the vector. These vectors can be viral vectors, such as retroviral, adenoviral, or adenoviral-associated vectors, as well as plasmids or cosmids. Prokaryotic or eukaryotic cells that contain and express DNA encoding any of the molecules comprising SipD, SipB, SseB or SseC; mutant SipD, SipB, SseB or SseC; SipD, SipB, SseB or SseC antigenic epitopes, fusion peptides (e.g. SEQ ID NOS: 14 and 16) etc, are also features of the invention. The method of transduction, the choice of expression vector, and the host cell may vary. The precise components of the expression system are not critical. It matters only that the components are compatible with one another, a determination that is well within the abilities of skilled artisans. Furthermore, for guidance in selecting an expression system, skilled artisans may consult Ausubel et al., Current Protocols in Molecular Biology (1993, John Wiley and Sons, New York, N.Y.) and Pouwels et al., Cloning Vectors: A Laboratory Manual (1987). The vector can also have a sequence that encodes a detectable marker, such as β-galactosidase, α-glucuronidase (GUS), luciferase, horseradish peroxidase (HRP), alkaline phosphatase, acetylcholinesterase, or chloramphenicol acetyl transferase. Fluorescent reporter genes include, but are not limited to, green fluorescent protein (GFP), red fluorescent protein (RFP), cyan fluorescent protein (CFP), and blue fluorescent protein (BFP). The detectable marker can also be an epitope tag, such as a myc, FLAG, or HA tag.

In an embodiment, a vector comprises one or more polynucleotides comprising SEQ ID NOS: 1-8, 13-16, or 23-24, variants, mutants, derivatives or fragments thereof. The vector can be administered to a patient wherein expression of SEQ ID NOS: 1-8, 13-16, or 23-24, variants, mutants, derivatives or fragments thereof, induce response. A number of vectors are known to be capable of mediating transfer of gene products to mammalian cells, as is known in the art and described herein. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al; *BioTechniques*, 34: 167-171 (2003). Large varieties of such vectors are known in the art and are generally available.

A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, et al. *PNAS* 88: 8850-8854, 1991).

Suitable nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem*, 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci* USA: 87:1149 (1990)], Adenovirus Vectors [LeGal LaSalle et al., *Science*, 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Feigner and Holm, Bethesda Res. Lab. Focus, 11(2):21 (1989) and Maurer, R. A., Bethesda Res. Lab. Focus, 11(2):25 (1989).

Replication-defective recombinant adenoviral vectors, can be produced in accordance with known techniques. See, Quantin, et al., *Proc. Natl. Acad. Sci.* USA, 89:2581-2584 (1992); Stratford-Perricadet, et al., *J. Clin. Invest.*, 90:626-630 (1992); and Rosenfeld, et al., Cell, 68:143-155 (1992).

Another delivery method is to use single stranded DNA producing vectors which can produce the SPI-1 and/or SPI-2 molecules intracellularly. See for example, Chen et al, *BioTechniques*, 34: 167-171 (2003), which is incorporated herein, by reference, in its entirety.

Expression of SPI-1 and/or SPI-2 molecules may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, 1981, *Nature* 290:304-310), the promoter contained in the 3' long terminal repeat of Rous sarcoma virus (Yamamoto, et al., *Cell* 22:787-797, 1980), the herpes thymidine kinase promoter (Wagner et al., *Proc. Natl. Acad. Sci. U.S.A.* 78:1441-1445, 1981), the regulatory sequences of the metallothionein gene (Brinster et al., *Nature* 296:39-42, 1982); prokaryotic expression vectors such as the β-lactamase promoter (Villa-Kamaroff, et al., *Proc. Natl. Acad. Sci. U.S.A.* 75:3727-3731, 1978), or the tac promoter (DeBoer, et al., *Proc. Natl. Acad. Sci. U.S.A.* 80:21-25, 1983); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., *Cell* 38:639-646, 1984; Ornitz et al., Cold Spring Harbor Symp. Quant. Biol. 50:399-409, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., *Cell* 38:647-658, 1984; Adames et al., *Nature* 318:533-538, 1985; Alexander et al., *Mol. Cell. Biol.* 7:1436-1444, 1987), mouse mammary tumor virus control region which is active in testicular, breast, lymphoid and mast cells (Leder et al., *Cell* 45:485-495, 1986), albumin gene control region which is active in liver (Pinkert et al., *Genes and Devel.* 1:268-276, 1987), alpha-fetoprotein gene control region which is active in liver (Krumlauf et al., *Mol. Cell. Biol.* 5:1639-1648, 1985; Hammer et al., *Science* 235:53-58, 1987), alpha 1-antitrypsin gene control region which is active in the liver (Kelsey et al., *Genes and Devel.* 1: 161-171, 1987), beta-globin gene control region which is active in myeloid cells (Mogram et al., *Nature* 315:338-340, 1985; Kollias et al., *Cell* 46:89-94, 1986), myelin basic protein gene control region which is active in oligodendrocyte cells in the brain (Readhead et al., *Cell* 48:703-712, 1987), myosin light chain-2 gene control region which is active in skeletal muscle (Sani, *Nature* 314:283-286, 1985), and gonadotropic releasing hormone gene control region which is active in the hypothalamus (Mason et al., *Science* 234:1372-1378, 1986).

A wide variety of host/expression vector combinations may be employed in expressing the nucleic acid sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2μ plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Yeast expression systems can also be used according to the invention to express SPI-1 and/or SPI-2 molecules. For example, the non-fusion pYES2 vector (XbaI, SphI, ShoI, NotI, GstXI, EcoRI, BstXI, BamH1, SacI, Kpn1, and HindIII cloning sites; Invitrogen) or the fusion pYESHisA, B, C (XbaI, SphI, ShoI, NotI, BstXI, EcoRI, BamH1, SacI, KpnI, and HindIII cloning sites, N-terminal peptide purified with ProBond resin and cleaved with enterokinase; Invitrogen), to mention just two, can be employed according to the invention. A yeast two-hybrid expression system can be prepared in accordance with the invention.

In certain embodiments, a single DNA construct expressing SPI-1 and/or SPI-2 molecules as two separate genes can be introduced into a cell or subject. In certain embodiments, a single DNA construct expressing SipD, SipB, SseB, or SseC as four separate genes can be introduced into a cell or subject. Exemplary expression constructs can be formulated as a pharmaceutical composition, e.g., for administration to a subject. DNA constructs and the therapeutic use of such constructs are well known to those of skill in the art (see, e.g. Chiarella et al. (2008) Recent Patents Anti-Infect. Drug Disc. 3: 93-101; Gray et al. (2008) *Expert Opin. Biol. Ther.* 8:911-922; Melman et al. (2008) *Hum. Gene Ther.* 17: 1165-1176). Naked DNA constructs typically include one or more therapeutic nucleic acids and a promoter sequence. A naked DNA construct can be a DNA vector, commonly referred to as pDNA. Naked DNA typically does not integrate into chromosomal DNA. Generally, naked DNA constructs do not require, or are not used in conjunction with, the presence of lipids, polymers, or viral proteins. Such constructs may also include one or more of the non-therapeutic components.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration.

In various embodiments, one or more viral vectors that expresses the SPI-1 and/or SPI-2 molecules encoding a polypeptide or polypeptides of the invention is administered by direct injection to a cell, tissue (e.g. i.m.), or organ of a subject, in vivo.

In some embodiments of the invention, it may be desirable to use a cell, cell type, cell lineage or tissue specific expression control sequence to achieve cell type specific, lineage specific, or tissue specific expression of the SPI-1 and/or SPI-2 polynucleotide sequences, for example SEQ ID NOS: 14, 16, to express a particular nucleic acid encoding a polypeptide in only a subset of cell types, cell lineages, or tissues, or during specific stages of development.

Certain embodiments of the invention provide conditional expression of the SPI-1 and/or SPI-2 polynucleotides of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the “GeneSwitch” mifepristone-regulatable system (Sirin et al, 2003, *Gene,* 323:67), the cumate inducible gene switch (WO 2002/088346), tetracycline-dependent regulatory systems, etc.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al, (1977) *Cell,* 11:223-232) and adenine phosphoribosyltransferase (Lowy et al, (1990) *Cell,* 22:817-823) genes which can be employed in tk- or aprt-cells, respectively.

The vector may comprise any regulatory sequence allowing proper expression of the coding nucleic acid in a selected host cell, e.g., a promoter, terminator, polyA, origin of replication, integration region (e.g., homologous region), intron, UTR sequences, marker gene, etc.

In another preferred embodiment, an expression vector comprising a nucleic acid molecule as defined above is provided, including a signal peptide, operably linked to regulatory elements allowing expression of said nucleic acid in a mammalian host or host cell. Preferred regulatory elements include a promoter, which may be selected, without limitation, from viral, cellular and synthetic promoters, including constitutive, tissue-specific or regulated promoters, in particular from the group consisting of the CMV promoter, E1Fa promoter and metallothionein promoter. Further regulatory elements that may be contained within the vectors of this invention include, without limitation, a Bcl-2 gene, UTR sequences and MAR sequences.

The above nucleic acids and vectors may be used for instance to produce recombinant SipD, SipB, SseB or SseC polypeptides in various competent host or host cells, as well as for gene therapy purposes.

The vector may be a plasmid, virus, phage, cosmid, episome, etc. Preferred vectors are viral vectors (e.g., recombinant adenoviruses) and plasmids, which can be produced based on commercially available backbones, such as pBR, pcDNA, pUC, pET, pVITRO, etc. The vector typically comprises regulatory elements or sequences to control or mediate expression of a polypeptide. The regulatory sequences may be chosen from promoters, enhancers, silencers, tissue-specific signals, peptide signals, introns, terminators, polyA sequences, GC regions, etc., or a combination thereof. Such regulatory elements or sequences may be derived from mammalian, fungal, plant, bacterial, yeast, bacteriophage or viral genes, or from artificial sources. Useful promoters for prokaryote expression (such as *E. coli*) include T7 RNA polymerase promoter (pT7), TAC promoter (pTAC), Trp promoter, Lac promoter, Tre promoter, PhoA promoter for example. Suitable promoters for expression in mammalian cells include viral promoters (e.g., CMV, LTR, RSV, SV40, TK, pCAG, etc.), domestic gene promoters (e.g., E1fα, chicken Pactine, Ubiquitine, INSM1, etc.), hybrid promoters (e.g., actine/globin, etc.), etc. A vector may comprise more than one promoter. The promoters may be inducible or regulated. For instance, the use of inducible or regulated promoters allows a better control of production by dissociating the culture from production phases. Inducible or regulated promoters may be found in the literature, such as the Tetracycline system, the Geneswitch system, the Ecdysone system, the Oestradiol system, the RU486 system, the Cumate system, the metallothionein promoter etc. Other systems are based on electric currents or microwaves, such as focalized ultrasound system, AIR induced expression system and the like. These systems can be used to control expression of a polypeptide according to the invention.

The polypeptides may be co-expressed with other factors. The cDNAs coding for each may be both placed downstream of the same promoter, but separated by an IRES sequence, or each of them downstream of its own promoter.

The vector may further comprise an origin of replication and/or a marker gene, which may be selected from conventional sequences. An amplification selection marker such as the DHFR gene can be inserted in the backbone of the vector. The vector may further comprise various combinations of these different elements which may be organized in different ways.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out Cells: The present invention also provides for cells comprising a nucleic acid or a vector as described above.

In a preferred embodiment, a cell comprises any of the polypeptides described herein, any of the nucleic acid molecules described herein, or any of the expression vectors described herein (for example, a stem cell, cell-line, an APC, a T cell or a B cell, in culture or in vivo).

In another embodiment, a cell expressing a chimeric molecule wherein the chimeric molecule comprises at least one Salmonella pathogenicity island 1 (SPI-1) and at least one Salmonella pathogenicity island 2 (SPI-2) protein, peptides, derivatives, variants or combinations thereof. In embodiments, the cell comprises: an animal cell, a mammalian cell, a bacterial cell, a yeast cell, a tumor cell, a transformed cell, a cell-line or any combinations thereof. The cells expressing the SPI-1 and SPI-2 molecules can be transfected or transformed and administered to the subject. The cells can secrete the encoded SPI-1 and SPI-2 molecules into blood and lymphatic system. Alternatively, the cells can express the SPI-1 and/or SPI-2 molecules on the cell surface such that they are presented to immune cell to stimulate an immune response. Accordingly, the cells encoding for: SPI-1, SPI-2, SPI-1 chimeric molecules, SPI-2 chimeric molecules, or any peptides thereof, can be presented to the immune system for priming the immune system to eliciting an antigen specific response against any *Salmonella* serovars. The administration of the cells can be accompanied with an adjuvant.

The host cell may be selected from any eukaryotic and prokaryotic cells, typically from a mammalian cell (in particular a human, rodent, canine cell), a bacterial cell (in particular *E. coli, Bacillus brevis, Bacillus subtilis*), a yeast cell, a plant cell and an insect cell. These host cells may be adapted to serum-free media. Production may also be accomplished in a transgenic animal or plant.

In some embodiments, recombinant host cells are selected from mammalian cells, in particular human cells as well as derivatives or mutants thereof, including bone marrow cells, stem cells, cells of the immune system and the like. Other examples of suitable host cells include Chinese Hamster Ovary (CHO) cells, Baby Hamster Kidney (BHK) cells, Human Embryonic Kidney (HEK-293) cells, human epidermal keratinocytes (HEK), human stromal or epithelial cells, PERC6, etc. In such mammalian cells, polypeptides may be produced as a secreted protein using functional signal peptide sequences.

Vaccination and Immunogenicity

Immune systems are classified into two general systems, the "innate" or "primary" immune system and the "acquired/adaptive" or "secondary" immune system. It is thought that the innate immune system initially keeps the infection under control, allowing time for the adaptive immune system to develop an appropriate response. The various components of the innate immune system trigger and augment the components of the adaptive immune system, including antigen-specific B and T lymphocytes (Kos, *Immunol. Res.* 1998, 17:303; Romagnani, *Immunol. Today.* 1992, 13: 379; Banchereau and Steinman, *Nature.* 1988, 392:245). A "primary immune response" refers to an innate immune response that is not affected by prior contact with the antigen. The main protective mechanisms of primary immunity are the skin (protects against attachment of potential environmental invaders), mucous (traps bacteria and other foreign material), gastric acid (destroys swallowed invaders), antimicrobial substances such as interferon (IFN) (inhibits viral replication) and complement proteins (promotes bacterial destruction), fever (intensifies action of interferons, inhibits microbial growth, and enhances tissue repair), natural killer (NK) cells (destroy microbes and certain tumor cells, and attack certain virus infected cells), and the inflammatory response (mobilizes leukocytes such as macrophages and dendritic cells to phagocytose invaders).

Some cells of the innate immune system, including macrophages and dendritic cells (DC), function as part of the adaptive immune system as well by taking up foreign antigens through pattern recognition receptors, combining peptide fragments of these antigens with major histocompatibility complex (MHC) class I and class II molecules, and stimulating naive $CD8^+$ and $CD4^+$ T cells respectively (Banchereau and Steinman, supra; Holmskov et al., *Immunol. Today.* 1994, 15:67; Ulevitch and Tobias *Annu. Rev. Immunol.* 1995, 13:437). Professional antigen-presenting cells (APCs) communicate with these T cells, leading to the differentiation of naive $CD4^+$ T cells into T-helper 1 (Th1) or T-helper 2 (Th2) lymphocytes that mediate cellular and humoral immunity, respectively (Trinchieri *Annu. Rev. Immunol.* 1995, 13:251; Howard and O'Garra, *Immunol. Today.* 1992, 13:198; Abbas et al., *Nature.* 1996, 383:787; Okamura et al., *Adv. Immunol.* 1998, 70:281; Mosmann and Sad, *Immunol. Today.* 1996, 17:138; O'Garra *Immunity.* 1998, 8:275).

In adaptive immunity, adaptive T and B cell immune responses work together with innate immune responses. The basis of the adaptive immune response is that of clonal recognition and response. An antigen selects the clones of cell which recognize it, and the first element of a specific immune response must be rapid proliferation of the specific lymphocytes. This is followed by further differentiation of the responding cells as the effector phase of the immune response develops. These effector T lymphocytes, in the context of the embodiments, are the tumor specific T lymphocytes.

Delivery of an immunogen to appropriate cells can be effected ex vivo, in situ, or in vivo by use of any suitable approach known in the art. For example, for in vivo therapy, a nucleic acid encoding the SPI-1 and/or SPI-2 chimeric molecules, either alone or in conjunction with a vector, liposome, or precipitate may be injected directly into the subject, and in some embodiments, may be injected at the site where the expression of the molecules is desired. In other embodiments, cells comprising the nucleic acids encoding the SPI-1 and/or SPI-2 chimeric molecules are administered to a subject in need thereof, wherein the cells producing the immunogenic SPI-1 and/or SPI-2 peptides elicit an immune response to the immunogens. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxy-propyl)trimethylammonium bromide, commercialized as LIPOFECTIN by GIBCO-BRL)) (Feigner et al, (1987) Proc. Natl. Acad. Sci. USA 84, 7413-7417; Malone et al. (1989) Proc. Natl. Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) Biochim. Inter. 22, 235-241); 3β[N—(N',N'-dimethylaminoethane)-carbamoyl]cholesterol (DC-Chol), dioleoylphosphatidyl ethanolamine (DOPE)/3β[N—(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechniques 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 23 5(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP (SEQ ID NO: 25), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

Embodiments of the invention include methods of inducing an immune response in a subject comprising delivering an antigen to a subject in need thereof. In certain embodiments, the method comprises providing an antigen presenting cell (APC) and contacting (stimulating) them in vitro, ex vivo or in vivo with an SPI-1 and/or SPI-2 antigen either by incubation with the SPI-1 and/or SPI-2 peptides or with the cells expressing or secreting the SPI-1 and/or SPI-2 antigens. In certain embodiments, the antigen is delivered to the APC in the body of the subject. In certain embodiments, administration of a cell expressing one or more SPI-1 and/or SPI-2 molecules to the subject results in delivery of the antigen into an APC and T cell activation in the subject.

In another embodiment, an APC of the subject is isolated from the subject, the antigen is delivered to the APC outside of the body of the subject, and the APC comprising the delivered antigen is later administered to the subject.

In an embodiment, a method of enhancing the immune response in a mammal comprises the steps of contacting one or more lymphocytes with the antigenic compositions, wherein the antigen is presented by an immune cell, such as an APC. The enhanced immune response may be an active or a passive immune response. The response may be part of an adoptive immunotherapy approach in which APCs, such as dendritic cells, B cells or monocytes/macrophages, are obtained from a subject (e.g., a patient), then pulsed with a composition comprising the antigenic composition, and then administering the APC to a subject in need thereof. In certain embodiments, the method of the invention comprises ex vivo immunization and/or in vivo therapy in a subject. In one embodiment, the subject is a mammal. Preferably, the mammal is a human. Ex vivo procedures are well known in the art. Briefly, cells are isolated from a subject (preferably a human) and contacted with the antigenic compositions to produce an antigen-loaded APC. The antigen-loaded APC can be administered to a recipient to provide a therapeutic benefit. The recipient may be a human and the antigen-loaded APC can be autologous with respect to the recipient. Alternatively, the APC can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The preparation of compositions for use as vaccines is known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared (e.g. lyophilized, freeze-dried forms, etc.). The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of protein, polypeptide or peptide (or encoding nucleic acids) in the formulations may vary. However, in general, the amount of vaccinating/immunizing agent in the formulations will be from about 1 to about 99%.

In some embodiments, the immunogenic compositions embodied herein are administered with an immune modulating effector molecules or adjuvants. In one embodiment, an immune modulating effector molecule is administered in conjunction with or at alternative times the antigenic compositions or cells comprising the antigenic compositions. An immune-modulating effector molecule positively and/or negatively influences the humoral and/or cellular immune system, particularly its cellular and/or non-cellular components, its functions, and/or its interactions with other physiological systems. The immune-modulating effector molecule comprises cytokines, chemokines, macrophage migration inhibitory factor (MIF; as described, inter alia, in Bernhagen (1998), *Mol Med* 76(3-4); 151-61 or Metz (1997), *Adv Immunol* 66, 197-223), T-cell receptors and soluble MHC molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

In addition, the composition may contain adjuvants, many of which are known in the art. For example, adjuvants suitable for use in the invention include but are not limited to: bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A. Other non-toxic LPS derivatives include monophosphoryl lipid A mimics, such as aminoalkyl glucosaminide phosphate derivatives e.g. RC-529. Lipid A derivatives include derivatives of lipid A from Escherichia coli such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory. The CpG's can include nucleotide modifications/analogs such as phosphorothioate modifications and can be double-stranded or single-stranded. e.g. replacement of guanosine with 2'-deoxy-7-deazaguanosine. The CpG sequence may include, for example, the motif GTCGTT or TTCGTT. The CpG sequence may be specific for inducing a Th1 immune response, such as a CpG-A ODN, or it may be more specific for inducing a B cell response, such a CpG-B ODN. CpG-A and CpG-B ODNs. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers".

Bacterial ADP-ribosylating toxins and detoxified derivatives thereof may be used as adjuvants in the invention. Preferably, the protein is derived from *E. coli* (e.g. *E. coli* heat labile enterotoxin "LT"), cholera ("CT"), or pertussis ("PT"). The use of detoxified ADP-ribosylating toxins as mucosal adjuvants and as parenteral adjuvants is known. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, is known. Such adjuvants are described, for example, in issued U.S. Pat. No. 8,039,007 (the complete contents of which is hereby incorporated by reference in entirety). Various interleukins may also be used as adjuvants to increase the immune response in a subject. In preferred embodiments, the adjuvant is a mucosal adjuvant such as, for example, the double mutant heat-labile toxin (dmLT) from enterotoxigenic *E. coli*.

Administration and Formulations

The vaccine compositions (preparations) and immunogenic compositions (e.g. peptides, polypeptides, oligonucleotides, polynucleotides, etc.) of the present invention may be administered by any of the many suitable means which are well known to those of skill in the art, including but not limited to by injection, inhalation, orally, intranasally, topically, inclusion in a food product, etc. In some embodiments, the mode of administration is intradermal or intramuscular. In addition, the compositions may be administered in conjunction with or in a composition which contains other antigens of interest. In other words, they may be administered as a component of a multivalent vaccine which also contains antigens against other related or non-related infectious diseases, e.g. childhood diseases, such as polio, whooping cough, tetanus, diphtheria, etc.

Recipients of the vaccine of the invention are generally mammals, frequently humans, but this is not always the case. While in some aspects, the vaccine is used to prevent illness in humans, in other aspects, the vaccine is used to prevent illness and/or to block the carrier states in agriculturally important animals, i.e. veterinary applications are also contemplated. Animals which could benefit from receiving the vaccine/immune eliciting compositions of the invention include but are not limited to: cattle, poultry, swine, horses, sheep and goats. The vaccine is generally delivered intranasally or subcutaneously or intramuscularly, and may be delivered in combination with other agents such as other vaccinogens.

For humans, the vaccines may be administered alone or together with so-called "child hood" vaccines. Thus, the recipients are preferably human children who may be infants (e.g. up to about 1 hear of age), toddlers (e.g. up to about 2 years of age), or older, and administration may be carried out as a series of initial inoculations followed by booster doses at suitable intervals, e.g. monthly, or every 6-months, or yearly, etc. as necessary to provide protection. Thereafter, or in the case of adults who have not previously been vaccinated, the vaccines may be administered as necessary to result in a protective immune response, and subjects may be re-boosted e.g. about every 10 years throughout adult life. Of special interest is vaccination of individuals with compromised immune systems, e.g. the elderly, those receiving cancer or other immune weakening therapy, those afflicted with HIV, etc.

Vaccine recipients may have never been exposed to *Salmonella*, or may have been exposed or suspected of having been exposed but be asymptomatic, or may have actual symptoms of disease, and still benefit from administration of the vaccine. Vaccine administration may prevent disease symptoms entirely, or may lessen or decrease disease symptoms, the latter outcome being less than ideal but still better than experiencing full-blown disease symptoms.

In a preferred embodiment, the amount of protein that is administered per dose of vaccine is in the range of from about 0.0001 to about 1000 µg/kg. In one embodiment, the amount is in the range of from about 0.001 to about 1000 µg/kg of body weight of the recipient. In one embodiment, the amount is in the range of from about 0.01 to about 1000 µg/kg of body weight of the recipient. In one embodiment, the amount is in the range of from about 0.01 to about 100 µg/kg of body weight of the recipient. Those of skill in the art will recognize that the precise dosage may vary from situation to situation and from patient to patient, depending on e.g. age, gender, overall health, various genetic factors, and other variables known to those of skill in the art. Dosages are typically determined e.g. in the course of animal and/or human clinical trials as conducted by skilled medical personnel, e.g. physicians.

The vaccines and immunogenic compositions of the invention are broad-based vaccines and may be used to provide immune protection against a variety of *Salmonella* species, including both typhoidal and non-typhoidal species, and all *S. enterica* subspecies. Examples of these two categories of *Salmonella* include but are not limited to: for typhoidal *Salmonella*: Paratyphi A&B; and for non-typhoidal *Salmonella*: Typhimurium, Enteriditis, Newport, Dublin. Administration of the compositions of the invention results in the production of an immune response, which may be a protective immune response, in subjects who receive the compositions, e.g. by elicitation of antibody production against the administered antigens. Such antibodies are also encompassed by the invention, for example, those generated using laboratory techniques in experimental animals, or using cell culture, or by chemical syntheses, etc. Such antibodies may be polyclonal or monoclonal, and may be specific for the antigens (reacting with no other antigens) or selective for the antigens (reacting more strongly or preferably with the antigens, compared to other antigens). The antibodies may be multivalent. The antibodies may be used for research and/or diagnostic purposes, or alternatively, for treatment, especially of individuals who are infected with *Salmonella*.

The invention provides methods of vaccinating, or, alternatively, of eliciting an immune response, in a subject in need thereof. The method generally involves identifying a suitable subject, and administering the composition as described herein. The method may also encompass follow-up of administration, e.g. by assessing the production of protective antibodies by the subject, or the presence (or lack thereof) of disease symptoms, etc. The immune response that is elicited may be of any type, i.e. any type of antibody may be produced in response to administration, and cell-mediated immunity may also be elicited.

In addition, the invention provides methods of treating or preventing *Salmonella* infection by one or both of a typhoid *Salmonella* serovar and a non-typhoid *Salmonella* serovar in a subject, methods of lessening the severity of symptoms of *Salmonella* infection in a subject, and methods of decreasing fecal shedding of *Salmonella* from a subject who is or is likely to be infected with *Salmonella*. Each of these methods involves administering to the subject an amount of a composition comprising at least one *Salmonella* pathogenicity island 1 (SPI-1) and/or *Salmonella* pathogenicity island 2 (SPI-2) extracellular protein; and a physiologically acceptable carrier. The amount of the composition is administered is sufficient to elicit an immune response to the at least one *Salmonella* serovar in said subject, thereby of treating or preventing *Salmonella* infection, lessening the severity of symptoms of *Salmonella* infection, and/or decreasing fecal shedding of *Salmonella*.

In some embodiments, the compositions embodied herein, may be administered as a regimen in conjunction with other therapeutics, such, antibiotics, anti-inflammatory agents, The invention has been described in detail with reference to preferred embodiments thereof. However, it will be appreciated that those skilled in the art, upon consideration of this disclosure, may make modifications and improvements within the spirit and scope of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

In the case of *Salmonella*, an effective vaccine could be used to prevent illness in humans and to block the carrier activity in agriculturally important animals. Although some progress has been made in recent years, available vaccines against *Salmonella* spp. are not broadly protective and are almost entirely directed at the typhoid causing serovars, even though the non-typhoid serovars are a major public health problem.

Because the SPI-1 and SPI-2 proteins are surface localized prior to the invasion of host cells, they serve as prime targets for subunit vaccines. These four tip proteins are the initial tip protein SipD and the first 'translocator' protein SipB from SPI-1, and SseB and SseC from SPI-2, which are expressed and are surface exposed after entry of the bacterium into the cell. We previously demonstrated that the SipD and SipB homologs in *Shigella*, IpaD and IpaB, respectively, are protective antigens against challenge with serotypically distinct *S. flexneri* and *S. sonnei* strains using the mouse pulmonary model (see US patent application 20130149329, the complete contents of which is hereby incorporated by reference in entirety). A similar *Salmonella* serotype-independent subunit vaccine would be of tremendous public health value. Thus, we have determined the protective efficacy of SipD, SipB and SseB administered with adjuvants against challenge by *Salmonella* spp.

For Examples 1-3 below, recombinant SipD and SseB were prepared by expression in *E. coli* using His-tag technology and pET vectors (commercially available from Novagen), and purification was carried out via column chromatography. Within the cytoplasm of Salmonella, SipB forms a complex with its cognant chaperone SicA, and recombinant SipB was prepared with its chaperone by co-expression of His-tagged recombinants in *E. coli* and co-purification via column chromatography in a method similar to that of Birket et al. (Biochemistry [2007] 46:8128-8137). SipB was also produced alone by inducing its release from the chaperone using different detergents.

SipB, SipD, and SseB were then examined as protective antigens by immunizing mice (Examples 1 and 2) and calves (Example 3) intranasally or subcutaneous, followed by challenge, as described below. The results showed that SseB, SipB and SipD are effective in reducing the severity and length of disease caused by *Salmonella*. These findings impart a significant advancement over the live-attenuated and lipopolysaccharide-based vaccines that are currently being tested, because they provide serotype-independent protection and they can be given to children.

Example 1

Figure 2:
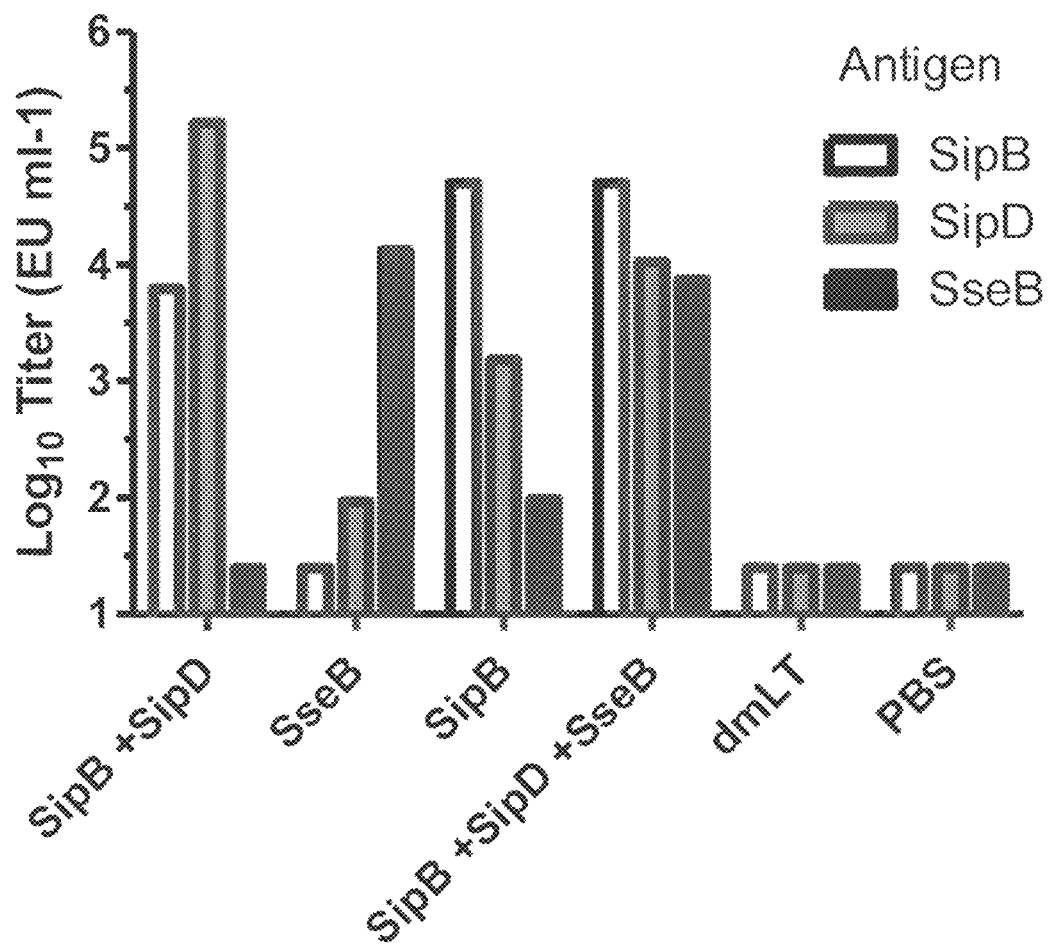
FIG. 2. IgG antibody titers from mice immunized with T3SS proteins at day 28. Each bar represents data from pooled samples (N=10).
Figure 3:
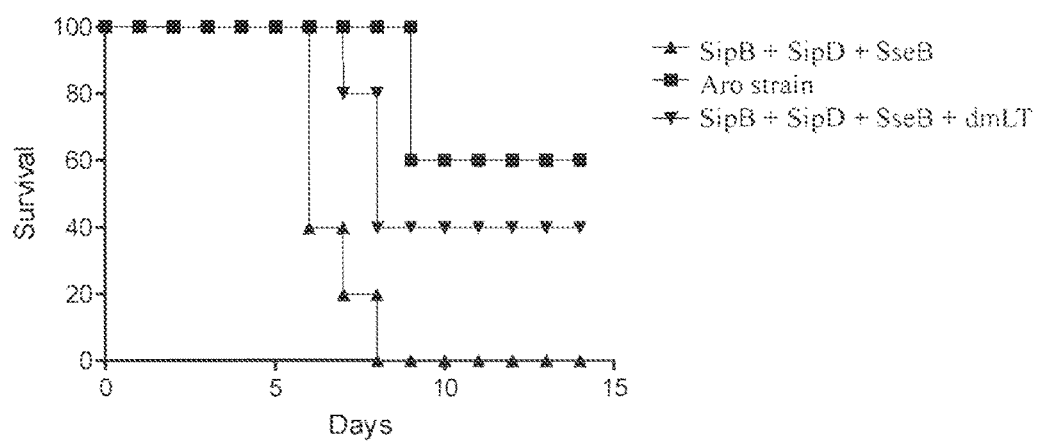
FIG. 3. Survival after challenge. Balb-c mice (N=5 per group) were vaccinated twice with attenuated *Salmonella* vaccine strain Aro, or 3 times with of a composition comprising SipB, SipD and SseB protein (10 μg of each) with or without adjuvant dmLT. Mice were challenged vias orogastric challenge with $1\times10^6$ CFU of Salmonella strain SL1344. Survival was monitored for 14 days after challenge.

FIG. 1 provides a Schematic illustration of a first mouse testing protocol for Example 1. Briefly, Balb-c mice (N=5 per group) were immunized intranasally 2 times with Aro strain or 3 times (days 0, 14 and 28) with 10 μg each of SipB/SipD/SseB protein with or without dmLT. Serum IgG and stool IgA were monitored throughout. Serum IgG antibody titers at day 28 are shown in FIG. 2. Mice were orogastrically challenged with $10^8$ colony forming units (CFUs) of *Salmonella enterica* serovar Typhimurium SL1344 after streptomycin treatment on day 56 and survival after challenge was monitored for 14 days after challenge. The results are shown in FIG. 3.

As can be seen, the proteins provide protection against a *S. typhimurium* challenge at a level approaching the live attenuated vaccine (Aro strain).

Example 2

Figure 4:
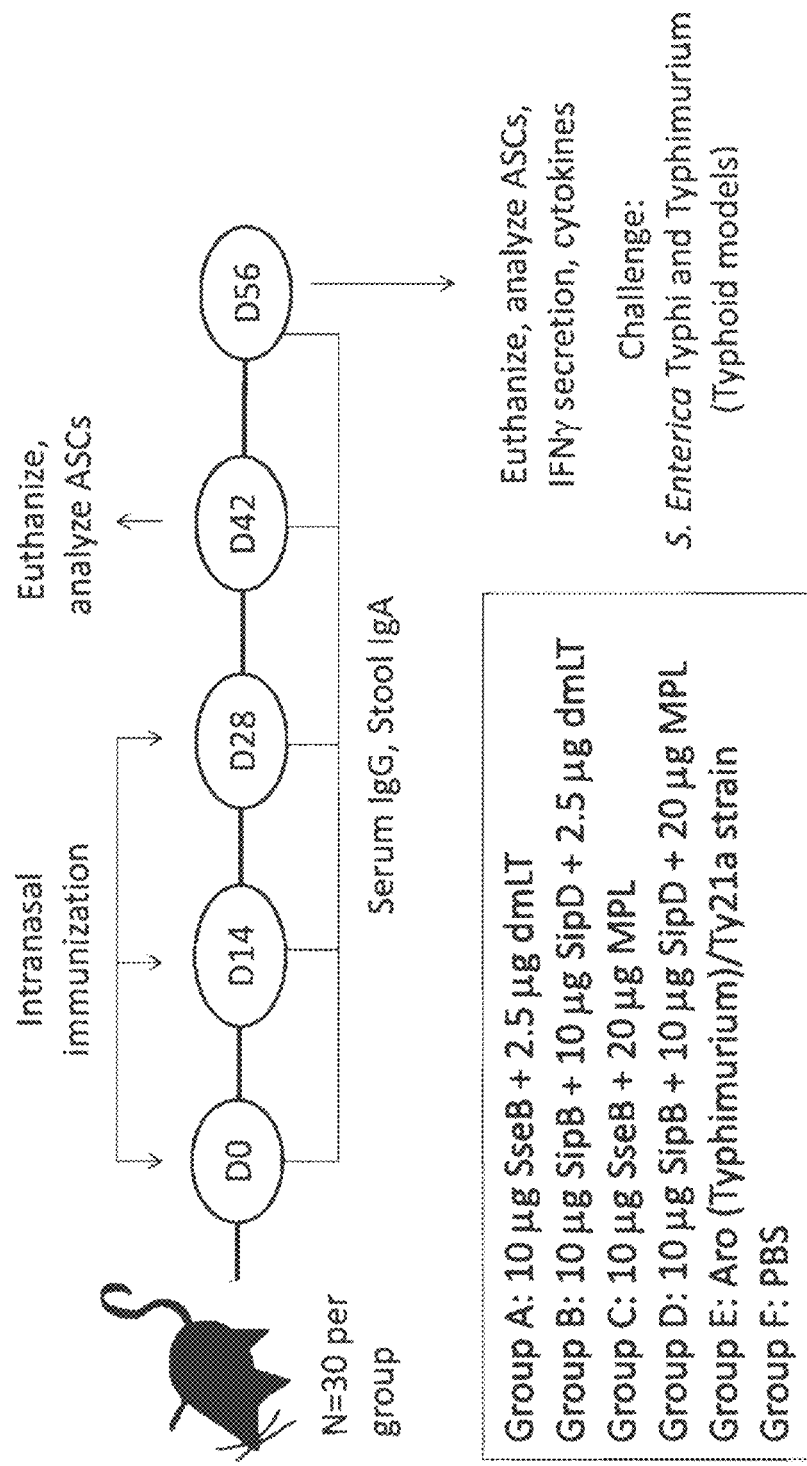
FIG. 4 contains a schematic illustration of the mouse testing protocol for Example 2.
Figure 5:
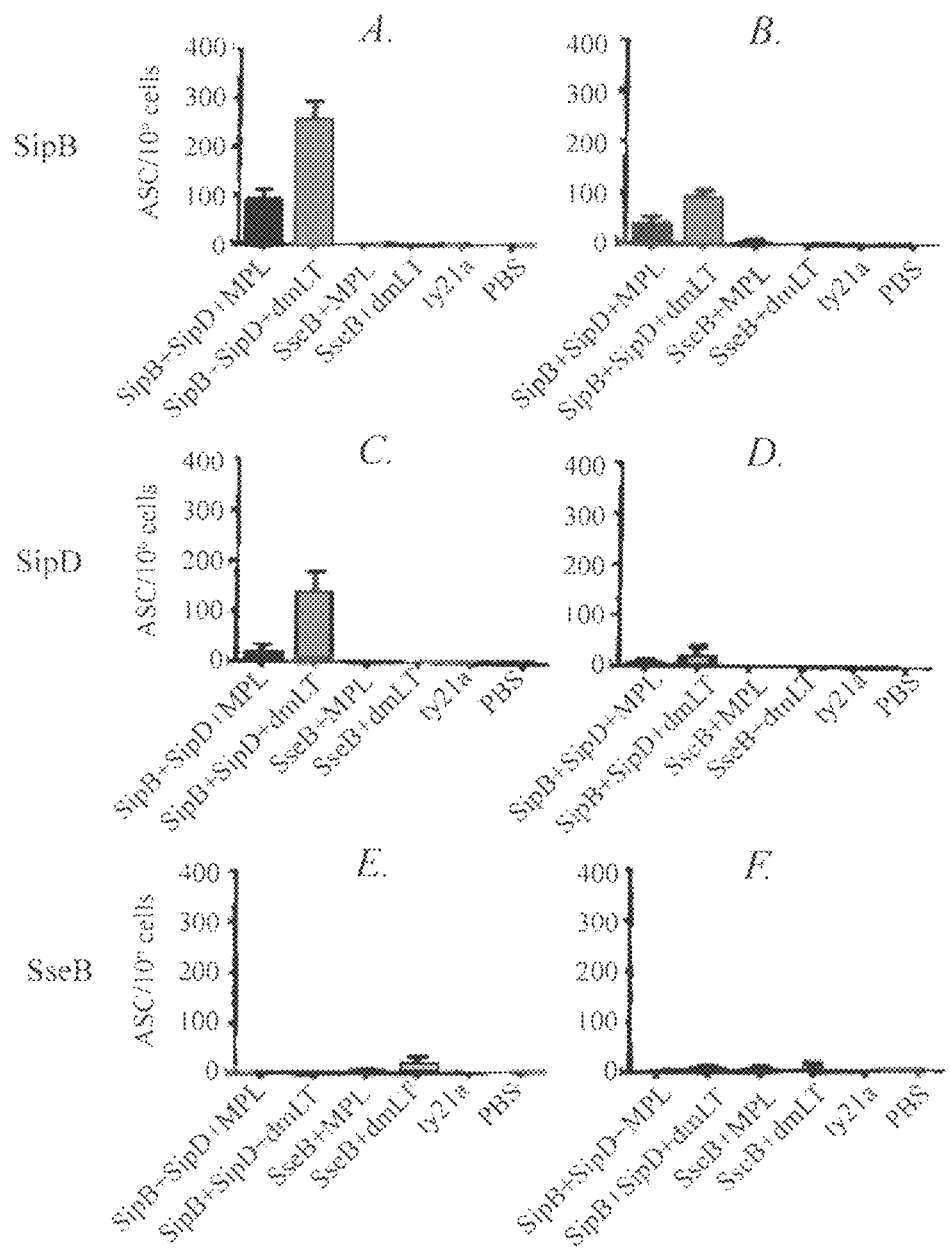
FIGS. 5A-5F.

FIG. 4 provides a Schematic illustration of a mouse testing protocol for Example 2. Briefly, Balb-c mice, n=30) were immunized on Days 0, 14 and 28 as follows: Group A: 10 μg SseB+2.5 μg of dmLT (double mutant *E. coli* heat labile toxin) as adjuvant; Group B: 10 μg SipB+10 μg SipD+2.5 μg dmLT; Group C: 10 μg SseB+20 μg MPL (monophooryl Lipid A); Group D: 10 μg SipB+10 μg SipD+20 μg MPL; Group E: Aro (Aro attenuated *S. enterica* var. Typhimurium vaccine strain, "Typhimurium/Ty21 a strain"); Group F: phosphate buffered saline (PBS, i.e. vehicle). At day 42 post immunization, some mice were euthanized and their spleens were analyzed for antibody secreting cells (ASCs). On day 56, additional mice were euthanized and analyzed for ASCs, IFNγ secretion, and cytokine production and the remaining mice were challenged with *S. enterica* typhi or typhimurium (typhoid models).

Figure 6:
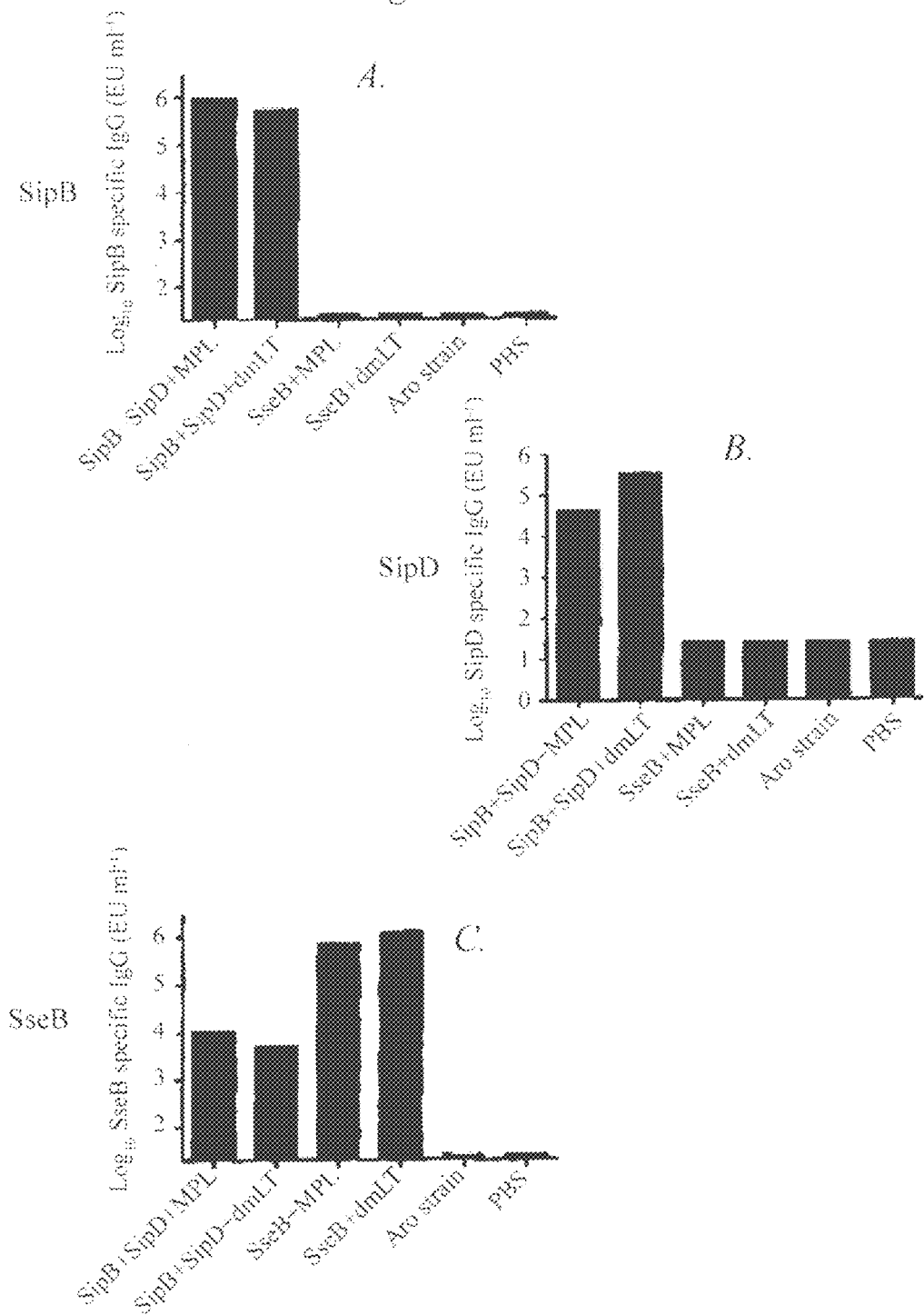
FIGS. 6A-6C. IgG titers in immunized mice at day 56.
Figure 7:
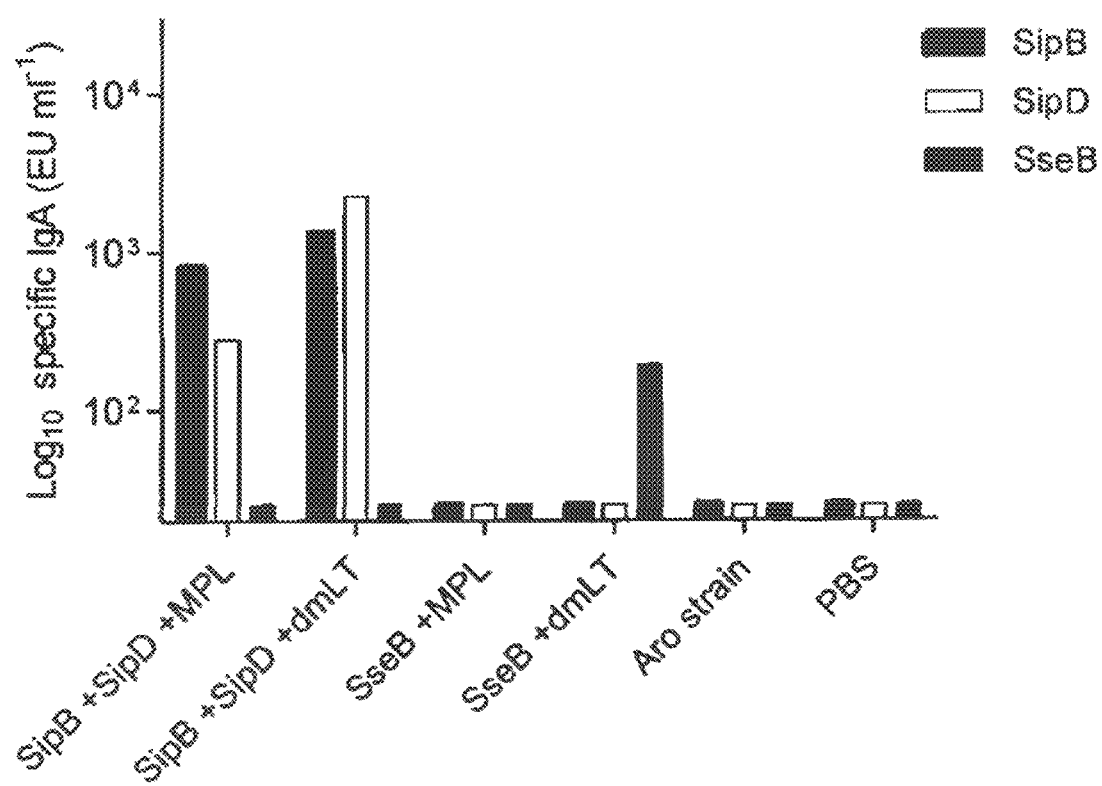
FIG. 7. Stool IgA titers in immunized mice at day 56.
Figure 8:
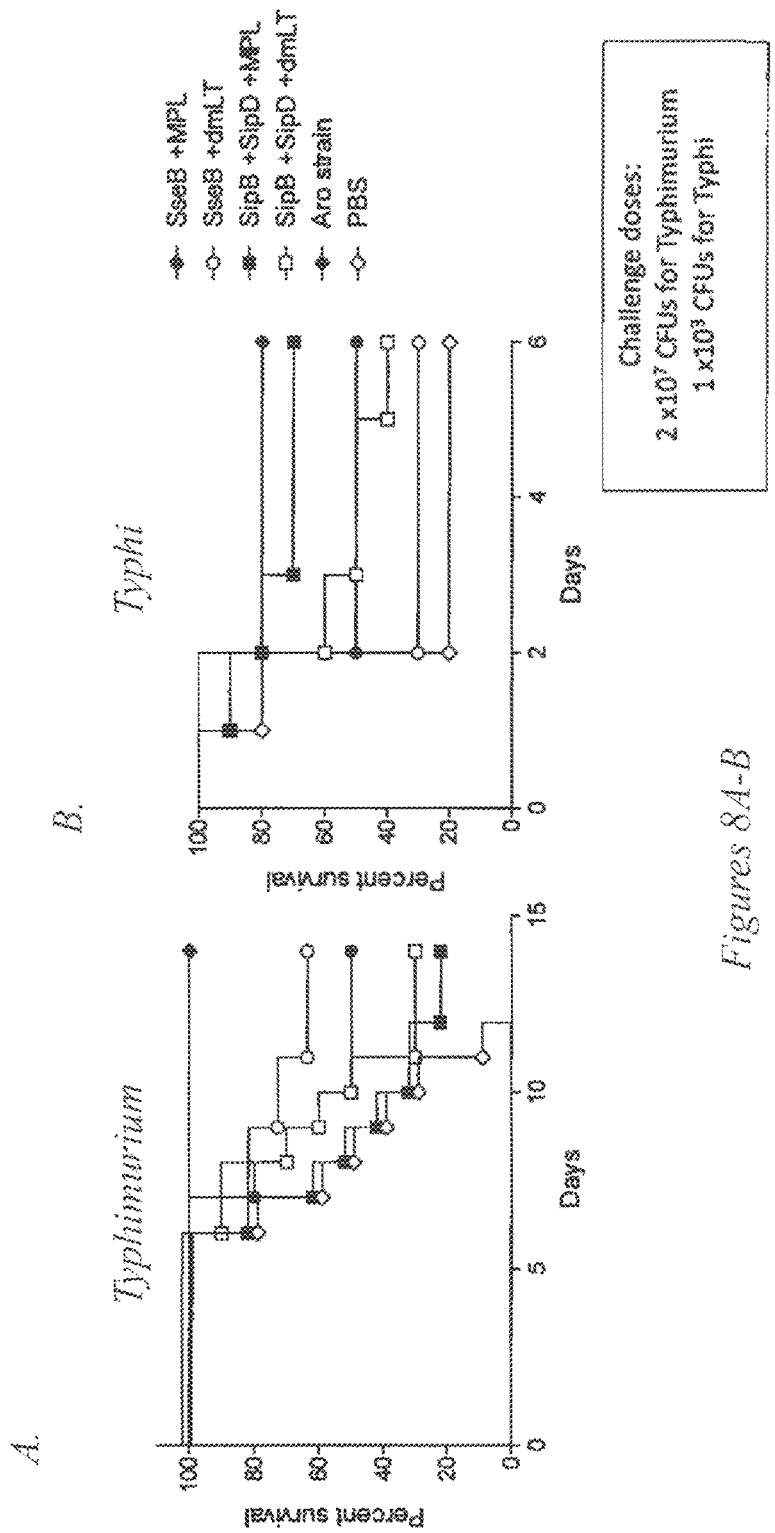
FIGS. 8A and 8B. Protection efficacy in immunized mice after challenge (at day 56) with (FIG. 8A) *S. enterica* Typhi or (FIG. 8B) *S. enterica* Typhimurium.

Immunogenicity as shown by spleen ASC results is shown in FIG. 5A-F. FIG. 6A-C shows IgG titers in immunized mice at day 56, FIG. 7 shows stool IgA titers in immunized mice at day 56, and FIG. 8A and FIG. 8B show protection efficacy in immunized mice after challenge (at day 56) with *S. enterica* typhi (FIG. 8A) or *S. enterica* typhimurium (FIG. 8B).

As can be seen, the results indicated that SipB, SipD and SseB are immunogenic in mice in that both serum and stool antibodies were detected after immunization, as were spleen ASCs specific for SipB and SipD. Interestingly, the challenge experiments showed different outcomes, with the combination of SipB/SipD being protective in Typhi intraperitoneal (IP) mucin challenge model and SseB being protective in the Typhimurium orogastric (OG) challenge model.

Example 3

First Calf Testing

Figure 9:
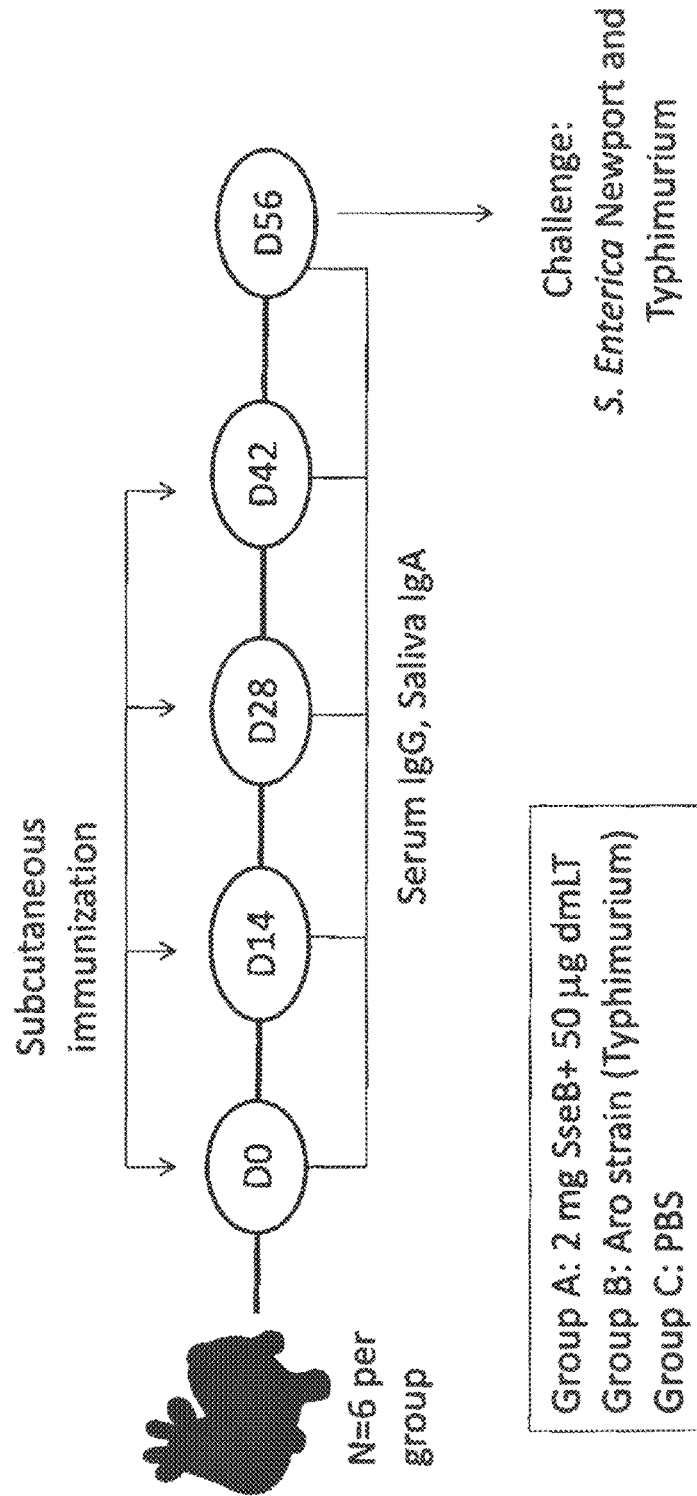
FIG. 9. Schematic illustration of the calf testing protocol for Example 3.

A schematic representation of the experimental protocol is provided in FIG. 9. Calves (21 day old male Holstein or Holstein-Jersey) were immunized subcutaneously at days 0, 14. 28 and 42 as follows: Group A, 2 mg SseB+50 μg of dmLT; Group B, Aro strain (Typhimurium); and Group C, PBS (control). Serum IgG (FIG. 10A) and saliva IgA (FIG. 10B) was measured. Calves were challenged with *S. enterica* Newport ($9 \times 10^5$ CFUs) or Typhimurium ($1.1 \times 10^8$ CFUs) on day 56. The amount of bacterial shedding in the two groups of challenged animals is shown in FIGS. 11A and B. As can be seen, the total bacterial shedding over the course of ten days for the group vaccinated with SseB+dmLT was not only lower, but the variation over the course of ten days was less than one log unit which is consistent with no effective increase in shedding over time. This is in contrast to the group vaccinated with PBS which had a higher average shedding and an average over the course of the study that spanned over 2.5 log units. Thus, the SseB+dmLT vaccine reduced disease severity relative to the control group and reduces shedding from the initial time point.

Example 4

Preparation of a Chimeric (Fusion) Protein

A SipD-SipB chimeric protein has been developed that allows the protective potential of SipD and SipB to be encompassed in single recombinant protein. This reduces the vaccine composition components to two proteins, the chimeric SipD-SipB and the SipA protein.

The sipD and sipB genes have been genetically fused in a single plasmid and co-transformed into *E. coli* TUNER (DE3) cells with a plasmid encoding sicA, using the following protocol: combine 1 μg of each plasmid with 30 μl chemically competent cells, heat shock, add one ml LB media, incubate at 37° C. for 1 hr and then plated on LB agar containing 100 μg/ml ampicillin and 30 μg Chloramphenicol. sipD was copied by PCR using primers with NdeI at 5' end and SalI at 3' end. sipB was copied by PCR using primers with SalI at 5' end and XhoI at 3' end. The PCR fragments were digested with the restriction enzymes and ligated together and then into NdeI/XhoI digested pET15b from Novagen. The ligation product was used to transform NovaBlue *E. coli*. Transformants were screened for the proper insert and subjected to double stranded sequencing. The gene encoding SicA was copied by PCR from *S.* Typhimurium SL1344 (accession number J04117). The PCR fragment was digested with the restriction enzymes NdeI and XhoI and ligated into NdeI/XhoI digested pACYC-Duet-1 from Novagen. The ligation product was used to transform NovaBlue *E. coli*. Transformants were screened for the proper insert and subjected to double stranded sequencing. A plasmid containing the correct sequence for the fusion and a plasmid containing the correct sequence for SicA were transformed into TUNER (DE3) *E. coli* (Novagen). This strain was used to inoculate LB media containing ampicillin and chloramphenicol. The bacteria were grown to an absorbance at 600 of about 0.6 at which time they were induced to over express IpaB/IpgC with Isopropyl-β-D-thiogalactoside (IPTG). The bacteria were grown an additional three hours to allow protein expression to occur. Alternatively, a starter culture of 100 ml was used to inoculate a 5- or 10-liter fermentor vessel containing TB media. After growing overnight (16 hours), the bacteria were induced and allowed to express protein for three hours. The bacteria were collected by centrifugation, resuspended in binding buffer (see below for recipe), and lysed by microfluidization. This suspension was clarified by centrifugation and was loaded onto a nickel charged immobilized metal affinity column (IMAC). The column (5 ml) was washed with 10 bed volumes each of binding and wash buffers and then subjected to a gradient of 0% to 40% elution buffer. Peak fractions were collected, the buffer exchanged into 1M ammonium sulfate in 50 mM sodium phosphate pH 7.0 and loaded onto a Butyl Sepharose High Performance column (5 ml) with a linear gradient from 1M ammonium sulfate in 50 mM sodium phosphate pH 7.0 to 50 mM sodium phosphate. For preparation of His-tag fusion, the IMAC-bound protein complex was incubated overnight in the presence of 1% OPOE. The chaperone was removed in the flow through and subsequent wash steps. His-tag fusion was eluted in the presence of OPOE to maintain the protein in a soluble form. All proteins were concentrated by ultrafiltration and dialyzed into PBS pH 7.2. Protein concentrations were determined via absorbance at 280 nm using extinction coefficients based on the amino acid composition of each protein.

Buffers that were utilized are listed below:

TABLE 1

| 4× Charge Buffer (500 ml) | | |
|---|---|---|
| 200 mM NiSO$_4$ | 52.56 g | 1× = 50 mM |

TABLE 2

| 8× Binding Buffer (1 Liter) | | |
|---|---|---|
| 40 mM Imidazole | 2.72 g | 1× = 5 mM |
| 4M NaCl | 237 g | 500 mM |
| 160 mM Tris | 19.36 | 20 mM |

Mix together and pH to 7.9 with HCl.

TABLE 3

| 8× Wash Buffer (500 mL) | | |
|---|---|---|
| 480 mM Imidazole | 16.3 g | 1× = 60 mM |
| 4M NaCl | 117 g | 500 mM |
| 160 mM Tris | 19.68 | 20 mM |

Mix together and pH to 7.9 with HCl. If using urea drop the imidazole to 20 mM. 8X=160.

TABLE 4

| 4× Elution Buffer (500 mL) | | |
|---|---|---|
| 4M Imidazole | 136 g | 1× = 1M |
| 2M NaCl | 58.44 | 0.5M |
| 80 mM Tris | 4.84 | 20 mM |

Mix together and pH to 7.9 with HCl.

TABLE 5

| 4× Strip Buffer (500 mL) | | |
|---|---|---|
| 0.4M EDTA | 74.4 g | 1× = 100 mM |
| 2M NaCl | 58.44 | 500 mM |
| 80 mM Tris | 4.84 | 20 mM |

Mix together. Add NaOH pellets to get pH to 8.0 so that EDTA will dissolve. Then adjust pH to 7.9.

A chimeric protein containing both SipD and SipB proteins was produced (FIG. 13; SEQ ID NO: 7), together with SipA protein. This method allows a cGMP facility to produce these proteins with one fermentor run, significantly reducing the protein purification costs.

The chimeric protein is administered to a subject as described herein and, as a result, a protective immune response is elicited in the subject.

Example 5

In Vivo Vaccine Evaluation

Food safety is a health issue that affects not only the United States, but the rest of the world. Today, the globalization of the food chain means tainted beef in the United States could cause illness or death halfway across the globe. In fact, *Salmonella* tainted beef may be the most significant challenge facing ranchers and the beef industry today. From the dinner plate to the pet food bowl, *Salmonella* contamination is a top story demanding solutions. A broad and wide immunization policy with an effective vaccine that works regardless of serovar across multiple species would allow the elimination of *Salmonella* as an endemic disease on farms across the States.

The currently available *Salmonella* vaccines protect against a limited number of serovars and thus lack the impact and economic strength to change farm behavior, so subclinical infections continue to have a negative effect on both producer and consumer. By having a single vaccine that is cross-protective against virtually all *Salmonella*, would eliminate disease, morbidity and mortality for both animals and people.

The specific objective was to demonstrate homologous protection of the vaccine against *S. enterica* serovar Typhimurium in a calf model. The proof of concept experiments were conducted in mice and the data with one component of the vaccine demonstrated that this vaccine can reduce bacterial shedding of a heterologous serotype, *S.* Newport, to the serotype from which the subunit vaccine was derived.

Materials and Methods

Protein Purification. The recombinant proteins, S1F and S2F, were constructed as per the standard protocol (Chen, X., et al. *Infect Immun*. 2015; 83(1):292-299; Choudhari, S. P., et al. *Protein Sci*. 2013; 22(5):666-670; Choudhari, S. P., et al. *J Pharm Sci*. 2014. doi: 10.1002/jps.24047). Briefly, for S1F, the sipD-sipB gene fusion was cloned into pET9d which is kanamycin resistant and the gene for the cognate SipB chaperone SicA, was cloned into pACYC which is chloramphenicol resistant. The plasmids were co-transformed into *E. coli* Tuner (DE3) for expression. The bacteria are grown at 37° C. to an A$_{600}$ of 0.8 at which point IPTG was added to induce protein expression. After three hours, the bacteria were collected by centrifugation, lysed, and the inclusion bodies collected again in the pellet. The pellet was resuspended in IMAC binding buffer containing 6M urea. The solution was clarified by centrifugation and loaded onto a nickel charged IMAC column. The column was washed and the protein eluted. The eluted protein was passed over a Q column with the eluted protein slowly refolded by step dialysis into IMAC binding buffer with 0.05% (v/v) N, N-dimethyldodecylamine N-oxide (LDAO). The solution was passed again over an IMAC column to remove the chaperone which was released from the complex by the detergent. Fractions were collected and the final dialysis step exchanges the proteins into phosphate buffered saline (PBS) containing LDAO which is required to maintain solubility of the proteins and has a GRAS (Generally Regarded As Safe) Profile. Furthermore, this detergent confers a significant degree of thermal stability to this class of proteins as well (Chen, X. et al., 2015). The proteins were concentrated to 5 mg/ml and stored at −80° C. For S2F, the sseB-sseC gene fusion has been cloned into pET9d which is kanamycin resistant and the gene for the cognate SseC chaperone SscA, was cloned into pACYC which is chloramphenicol resistant. The plasmids were co-transformed into *E. coli* Tuner (DE3) for expression. The remainder of the purification is the same as S1F.

Vaccine Preparation. The adjuvant for preparing purified subunit vaccine is monophosphoryl lipid A (MPL; Sigma Chemical Co.) combined with dipalmitoylphosphatidyl choline (DPPC) in a 4:1 molar ratio. Two milligrams of each protein were combined with ~2 mg of Alhydrogel (AH) and allowed to bind for one hour with gentle shaking at room temperature. Currently, binding isotherms are being performed to determine the actual optimal Alhydrogel ratio per unit protein. MPL (100 µg) was added to the formulation with a final vaccine formulation containing 1 ml. A live attenuated ΔSPI-1/2 *S.* Typhimurium strain was used for the positive control and grown overnight at 37° C. with shaking, collected by centrifugation, washed and finally resuspended in PBS at $1 \times 10^7$ cfu/ml. The negative control was PBS only.

Large Animal Efficacy Study. The calf experiments are performed at the Veterinary and Biomedical Research Center (VBRC), Manhattan, Kans. by Kelly Lechtenberg, DVM, PhD. All animals used are approved by the VBRC Institutional Animal Care and Use Committee. Holstein steers, 200 pounds, are obtained from one of the commercial Holstein calf vendors that can assure study candidates are *Salmonella*-free and have not been given any commercial vaccine against *Salmonella* by pre-screening fecal samples and by control of vaccination and management protocols. Fecal samples are obtained prior to the experiment to ensure no *Salmonella* is detectable. Calves are housed individually in indoor pens. Calves are initially fed twice daily (bottle or pail) with a commercial milk replacer appropriate for the age of the calves. As calves start to consume non-medicated dry feed, milk feeding is reduced to once daily to enhance dry feed consumption. Calves will have access to fresh water ad libitum.

Vaccination. Two groups (n=10/group) of calves are vaccinated subcutaneously three times on days 0, 14, and 28, with either PBS or the S1F+S2F (2 mg each) adsorbed to AH then admixed with 100 µg MPL (see above vaccine formulation). The ΔSPI-1/2 strain (2 ml) is fed to another group of 10 calves on days 0 and 28 by mixing with milk. Groups of ten were chosen as this is the minimum number that is required to obtain significant results in both the challenge experiment and the immunology determinations. In addition, performance of a power analysis evidences that a number of 10 animals per group are enough to discern a difference of ~20% in protective capacity.

Sample collection. Blood is drawn at 0, 14, 28, and 42 to obtain serum (from clotted blood) and peripheral blood mononuclear cells (PBMCs, from Heparinized blood) via standard procedures. Fecal samples and saliva are collected at these times as well. One mg of fecal contents is suspended in 1 ml of PBS containing sodium azide and the suspension shaken vigorously by vortexer for 15 min. The suspension is clarified and the supernatant is frozen at −80° C. until analyzed by ELISA. Although total IgA can be detected, it is possible that rectal secretions need to be obtained to detect antigen-specific IgA in fecal samples. As an alternative, six cotton-tipped applicators are used to collect saliva from under the tongue and around the cheek. The saliva is transferred via centrifugation into a 50 ml conical tube from the applicators that are in a 15 ml conical tube with a hole in the bottom. Kinetics of serum IgG and fecal IgA titers are determined. The Immunological Core of the KVI performs the ELISAs to determine the antigen-specific IgG and IgA levels. (Martinez-Becerra, F. J. et al. *Infect Immun.* 2013a; 81(12)4470-4477; Martinez-Becerra, F. J., et al. *Vaccine.* 2013b; 31(24):2667-2672). The preliminary data provided for the protective efficacy of SseB in calves included determination of the kinetics of serum IgG and fecal IgA production by the calves. Peripheral blood mononuclear cells (PBMCs) separated from blood samples are incubated in plates with SipD, SipB, SseB, and SseC to assess the frequency of antibody secreting cells. Similarly, after stimulation with the antigens, the cells and supernatant are assessed for IFN-γ and IL-17 levels via flow cytometry and ELISA respectively. Statistical analysis is performed using Graphpad prism and FlowJo software. Differences among treatments are analyzed using ANOVAs and t-tests. A P value<0.05 is considered significant for all analysis.

Go/No Go to Challenge. Based on previous immunological results, the titers for the anti-SipD, SipB, SseB, SseC-specific IgG were at least $10^3$-$10^4$ ELISA units/ml with IgA units being $10^3$ ELISA units/ml. Background was less than 25 EU/ml. Similarly, there should be 100 IgG and 50 IgA antibody secreting cells (ASC) specifically directed against each antigen per $10^6$ peripheral blood mononuclear cells (PBMCs). In a previous calf experiment (see challenge results below), an increase in IFNγ and IL-17 levels were observed. If these conditions are not met, another vaccination is performed. Three vaccinations stimulate a complete immune response since maximal IgG and IgA titers were detected at the sampling associated with day 48 vaccination.

*S.* Typhimurium Challenge. Calves are challenged orally with $1.2 \times 10^7$ *S. typhimurium* SL1344 (Sm$^r$) which is the inoculum required to result in *Salmonella*-positive peripheral lymph nodes (Brown, T. R., et al. *Journal of Food Protection.* 2015; 78(3):573-578). The bacteria are grown at VBRC at 37° C. overnight with shaking, collected by centrifugation, washed and finally resuspended in PBS at $1.2 \times 10^7$ cfu/ml. A sample of the final inoculum is subjected to dilution plating to determine the actual final inoculum (prior to challenge, growth, manipulation and dilution is performed until the dilution plating is within 1% error on 3 consecutive trials). Upon challenge, weight loss is monitored over a seven day period (Day 0 and Day 7). Temperature is monitored in the morning (daily). Health scores are determined (Snider, T. A., et al. *Vet Microbiol.* 2014; 170 (1-2):65-72) in the morning (daily). Fecal shedding is monitored over a seven day period by resuspending 1 mg of fecal matter in 10 ml of PBS by vortexing, and serial dilutions plated onto TSB+streptomycin (50 µg/ml). At the end of the study, the calves are euthanized, necropsies performed, and the *Salmonella* burden assessed in the matter of the gastrointestinal tract (rumen, cecum, colon, and rectum) and in the major lymph nodes (mesenteric, subiliac, popliteal, and superficial cervical) as per standard published methods (Brown, T. R. et al. 2015).

Go/No Go to heterologous challenge and Phase II. The *Salmonella* carriage in the lymph nodes of the vaccinated calves should be reduced by 90-100% from unvaccinated animals. The shedding should be eliminated in the vaccinated calves earlier relative to the unvaccinated as well as the level of shedding should be reduced at least four logs.

Results

Figure 14:
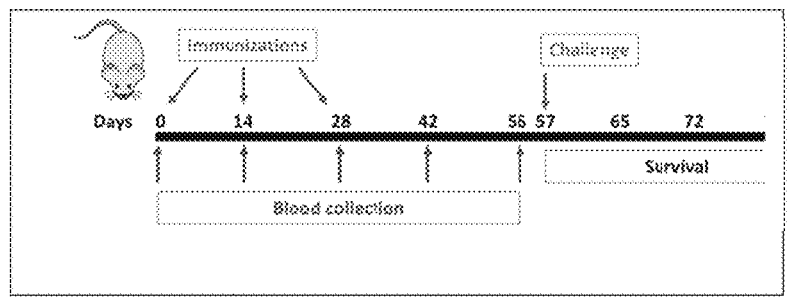
FIG. 14 is a schematic representation of an experimental plan for mouse experiments.
Figures 15A, 15B, 15C, 15D:
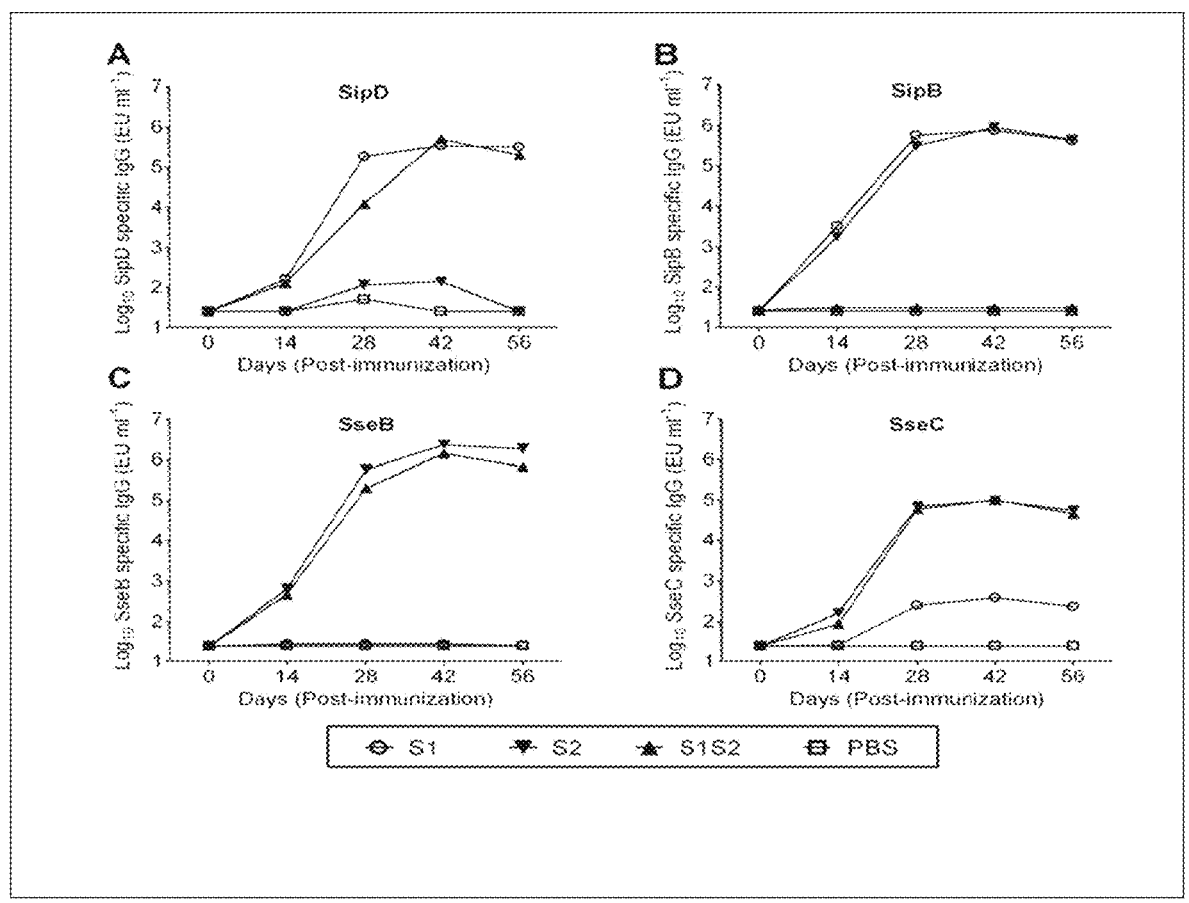
FIGS. 15A-15D are graphs showing the kinetics of serum IgG response against SipD, SipB, SseB, and SseC. Serum samples from blood collected at days 0, 14, 28, 42, and 56 were analyzed for their titers against the four proteins that are part of the S1F (SipD and B) and S2F (SseB and C). All the titers are from pooled serum from the group of mice tested (N=10).

SipD and SipB alone or together did not provide complete protective efficacy. SseB, in contrast, does provide some protection (see calf data, FIG. 17). *Salmonella* fusion proteins S1F and S2F were made recombinantly in *E. coli*. Five total groups (n=15) of female BALB/c mice were used with the experimental plan depicted in FIG. 14. Four groups were vaccinated intramuscularly three times with 100 µl of vaccine formulation containing the following: 1) 20 µg S1F+50 µg monophosphoryl lipid A (MPL)+50 µg Alhydrogel (AH); 2) 20 µg S2F+50 µg MPL+50 µg AH; 3) 20 µg S1F+20 µg S2F+50 µg MPL+50 µg AH; 4) buffer only (phosphate-buffered saline; PBS). Finally, one group was vaccinated on day 28 with a live-attenuated strain of either *S. Typhimurium* or *S. Enteritidis*. Blood samples (processed to obtain serum) from all the mice were collected at day 0, 14, 18, 42 and 56 during the course of vaccination. Anti-SipB, -SipD, -SseB, and -SseC IgG serum titers were determined along with the IgA titers from fecal samples. No IgA response against any of the antigens was detected in fecal samples. This result was observed with parenteral immunization using the *Shigella* IpaD-IpaB Fusion. Mice that were vaccinated with S1F elicited a robust anti-SipB and -SipD IgG response (FIGS. 15A-15D). Interestingly, a modest amount of cross-reactivity was detected with the S2F group. Likewise, mice vaccinated with S2F elicited a robust anti-SseB and -SseC IgG responses. Samples from mice vaccinated with live-attenuated strain were not tested since, in the past, this strain has elicited a response to LPS and not to these antigens.

Figures 16A, 16B:
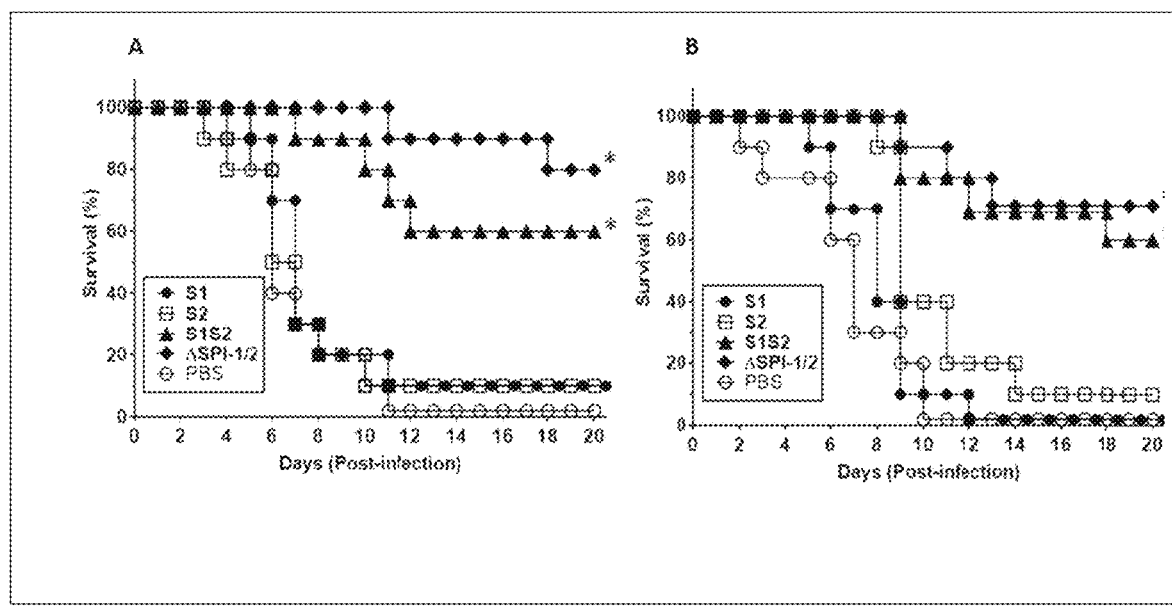
FIGS. 16A and 16B are graphs showing the results from an orogastric/systemic challenge with *S.* Typhimurium SL1344 and *S.* Enteritidis P125109. Immunized mice (n=10) were challenged with (FIG. 16A) $2\times10^8$ cfu *S.* Typhimurium SL1344 and (FIG. 16B) $8\times10^7$ cfu *S.* Enteritidis orogastrically. Survival was monitored for 21 days. $p<0.05$ for ΔSPI-1/2 and S1F+S2F compared to PBS group.

At day 56 post-immunization, five mice from each immunized group were euthanized to collect spleen and bone marrow. Single cell suspensions obtained from spleens and bone marrows were stimulated with the four antigens and the frequency of IgG antigen-secreting cells (ASC) in the spleen and bone marrow was determined by ELISpot assay (FIGS. 16A, 16B). Mice groups immunized with S1F demonstrated high frequencies of anti-SipB IgG ASC, but more modest frequencies of anti-SipD IgG ASC in bone marrow. The groups immunized with S2F had high frequencies of anti-SseB IgG ASC and moderate frequencies of anti-SseC IgG ASC in bone marrow. No profound IgG ASC against the four antigens was detected in the spleens from mice vaccinated with the live-attenuated strain or PBS.

On day 56, the remaining mice were challenged with $2\times10^8$ cfu ($10LD_{50}$) of *S. Typhimurium* SL1344 (wild-type) or $8\times10^7$ cfu ($10LD_{50}$) of *S. Enteritidis* (wild-type). In this model, mice do not exhibit symptoms of gastroenteritis but they do develop a systemic typhoid-like illness with death as the endpoint. Mice that were immunized with the live-attenuated strain showed 80% and 70% survival in case of *S. Typhimurium* and *S. Enteritidis* challenges, respectively (FIGS. 16A, 16B). This was an expected observation since the protection afforded to the mice by this strain is serotype specific. Although the S1F and S2F vaccine formulations conferred no protection, the combination of S1F+S2F showed an encouraging survival pattern with 60% protection against lethal challenges regardless of serovar used for challenge. The fact that the current vaccine formulation confers significant protection before even optimizing the vaccine formulation is promising.

Figure 17:
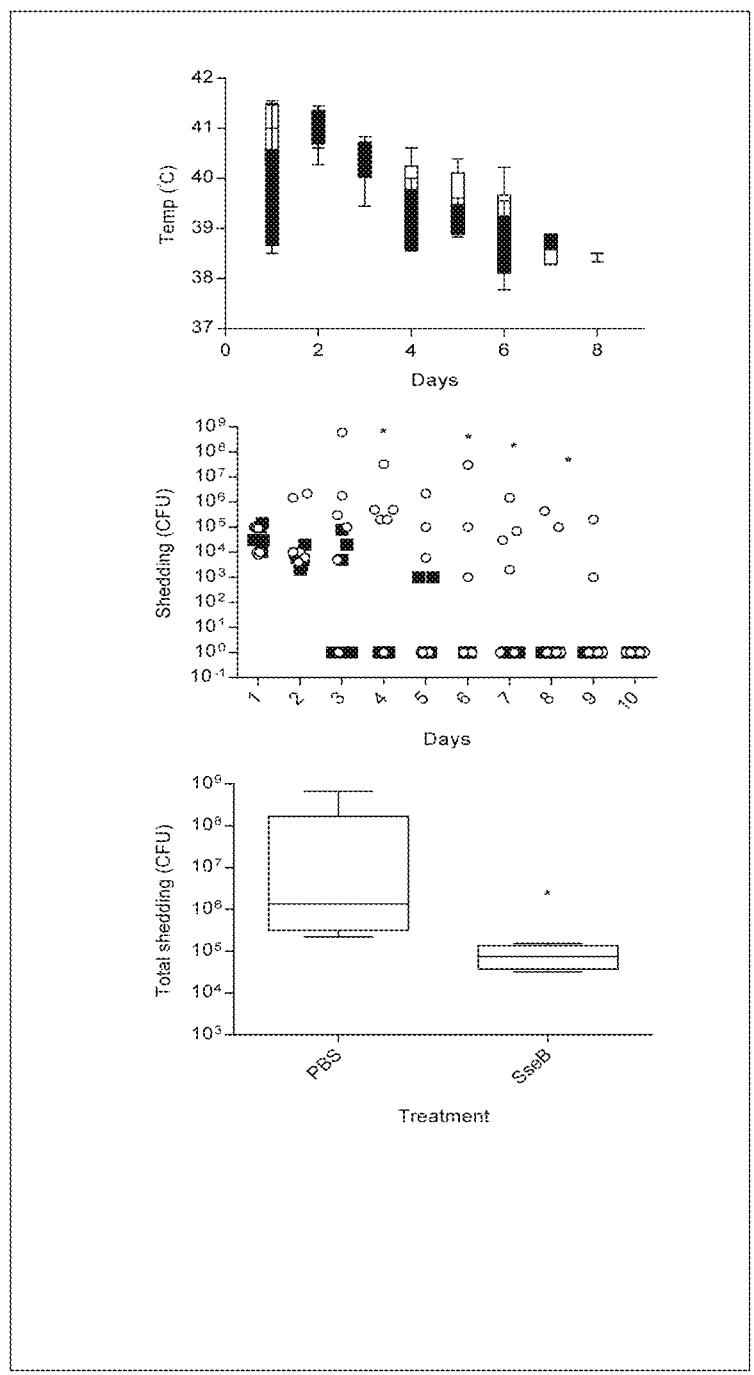
FIG. 17 is a series of graphs showing rRectal temperatures and shedding of *S.* Newport following bacterial challenge of calves. Top: Temperatures of the calves over the course of eight days after challenge. Black boxes indicate temperature from calves vaccinated with SseB+dmLT and white boxes are sham-vaccinated calves. Middle: fecal shedding (CFUs/gram of feces) for individual calves over the ten day study. Black boxes indicate shedding from each calf vaccinated with SseB+dmLT and white circles are sham-vaccinated calves. Bottom: Total shedding of bacteria (CFUs) over the entire ten day period. *$P<0.05$ comparing groups that received SseB+dmLT and PBS using T test.
Figure 18:
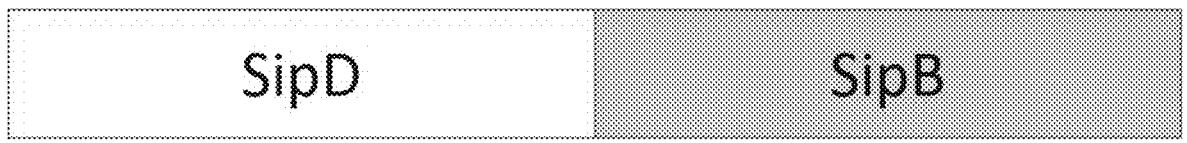
FIG. 18 is a schematic representation of the S1 Fusion (S1 or S1F). S1F is a genetic fusion of SipD and SipB. Upon protein purification, the linear model is depicted in the diagram where SipD is expressed first (light grey) with translation continuing into SipB (dark grey).
Figure 19:
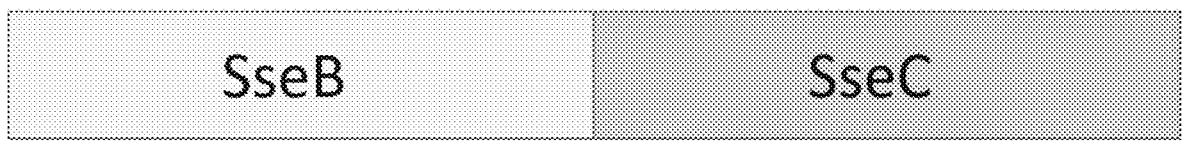
FIG. 19 is a schematic representation of the S2 Fusion (S2 or S2F). S2F is a genetic fusion of SseB and SseC. Upon protein purification, the linear model is depicted in the drawing where SseB is expressed first (light grey) with translation continuing into SipB (dark grey).

Previously, SseB was tested in a calf study to assess protective efficacy. Calves were vaccinated subcutaneously (n=6) with 2 mg SseB (a component of S2F) admixed with 50 dmLT (double mutant labile toxin from enterotoxigenic *E. coli*) or PBS (n=6). These twelve calves were challenged with *S.* Newport. Each set of calves exhibited a significant increase in body temperature by day 2 indicating a successful *S.* Newport infection (FIG. 17, top). Except for days 2 and 3, the trend of the temperatures exhibited by the SseB+dmLT group was lower than those of the PBS group. Fecal shedding was also monitored. On day 1 both groups shed $\sim10^5$ *S.* Newport/gram of feces (FIG. 17, middle). Over time, there was an increase in shedding from the sham-vaccinated calves and the majority of these calves continued shedding up to $10^5$ CFU/gram for most of the study. The sham-vaccinated animals were only able to achieve baseline levels on day 10. In contrast, the calves vaccinated with SseB+dmLT did not exhibit increased fecal shedding of *S. Newport*. Instead, day 2 and 3 shedding was maintained near $10^4$ with a drop to baseline levels at day 4. The lack of shedding on day 4 coincided with the return of normal rectal temperatures on this day. Although a slight increase was seen on day 5 for 2 animals, the remaining days saw baseline shedding levels. When the ten day total shedding was calculated, the vaccine efficacy in reducing *S. Newport* shedding was significant. The total ten day bacterial shedding for the group vaccinated with SseB+dmLT was not only lower than the sham-vaccinated group, but the variation over the ten day period was less than one log unit which is consistent with no effective increase in shedding over time (FIG. 17, bottom). Thus, the SseB+dmLT vaccine reduced disease severity relative to the control group and reduced shedding from the initial time point.

CONCLUSION

Vaccine prevention of *Salmonella* infections in livestock reduces time and money spent treating infections and reduces development of antibiotic resistance. There will be, in turn, less need for segregation and/or culling of sick animals that would be reservoirs for pathogen spread. The technology described herein for the production of this vaccine is one that is of use globally. Subunit vaccines are among the safest and there is no stigma like that encountered with genetically modified agricultural products. Thus, not only can this vaccine be used within the US, but it can be marketed for sale abroad.

```
S1fusion ((Nde-SipD-Sal-SipB-Xho) in pET28; SEQ ID NO: 13):
ATGGGCAGCAGCCATCATCATCATCATCACAGCAGCGGCCTGGTGCCGCGCGGCAG
CCATATGCTTAATATTCAAAATTATTCCGCTTCTCCTCATCCGGGGATCGTTGCCGAA
CGGCCGCAGACTCCCTCGGCGAGCGAGCACGTCGAGACTGCCGTGGTACCGTCTAC
CACAGAACATCGCGGTACAGATATCATTTCATTATCGCAGGCGGCTACTAAAATCCA
CCAGGCACAGCAGACGCTGCAGTCAACGCCACCGATCTCTGAAGAGAATAATGACG
AGCGCACGCTGGCGCGCCAGCAGTTGACCAGCAGCCTGAATGCGCTGGCGAAGTCC
GGCGTGTCATTATCCGCAGAACAAAATGAGAACCTGCGGAGCGCGTTTTCTGCGCCG
```

-continued

```
ACGTCGGCCTTATTTAGCGCTTCGCCTATGGCGCAGCCGAGAACAACCATTTCTGAT
GCTGAGATTTGGGATATGGTTTCCCAAAATATATCGGCGATAGGTGACAGCTATCTG
GGCGTTTATGAAAACGTTGTCGCAGTCTATACCGATTTTTATCAGGCCTTCAGTGAT
ATTCTTTCCAAAATGGGAGGCTGGTTATTACCAGGTAAGGACGGTAATACCGTTAAG
CTAGATGTTACCTCACTCAAAAATGATTTAAACAGTTTAGTCAATAAATATAATCAA
ATAAACAGTAATACCGTTTTATTTCCAGCGCAGTCAGGCAGCGGCGTTAAAGTAGCC
ACTGAAGCGGAAGCGAGACAGTGGCTCAGTGAATTGAATTTACCGAATAGCTGCCT
GAAATCTTATGGATCCGGTTATGTCGTCACCGTTGATCTGACGCCATTACAAAAAT
GGTTCAGGATATTGATGGTTTAGGCGCGCCGGGAAAAGACTCAAAACTCGAAATGG
ATAACGCCAAATATCAAGCCTGGCAGTCGGGTTTTAAAGCGCAGGAAGAAAATATG
AAAACCACATTACAGACGCTGACGCAAAAATATAGCAATGCCAATTCATTGTACGA
CAACCTGGTAAAAGTGCTGAGCAGTACGATAAGTAGCAGCCTGGAAACCGCCAAAA
GCTTCCTGCAAGGAGTCGACATGGTAAATGACGCAAGTAGCATTAGCCGTAGCGGA
TATACCCAAAATCCGCGCCTCGCTGAGGCGGCTTTTGAAGGCGTTCGTAAGAACACG
GACTTTTTAAAAGCGGCGGATAAAGCTTTTAAAGATGTGGTGGCAACGAAAGCGGG
CGACCTTAAAGCCGGAACAAAGTCCGGCGAGAGCGCTATTAATACGGTGGGTCTAA
AGCCGCCTACGGACGCCGCCCGGGAAAAACTCTCCAGCGAAGGGCAATTGACATTA
CTGCTTGGCAAGTTAATGACCCTACTGGGCGATGTTTCGCTGTCTCAACTGGAGTCT
CGTCTGGCCGGTATGGCAGGCGATGATTGAGTCACAAAAAGAGATGGGGATTCAGGT
ATCGAAAGAATTCCAGACGGCTCTGGGAGAGGCTCAGGAGGCGACGGATCTCTATG
AAGCCAGTATCAAAAAGACGGATACCGCCAAGAGTGTTTATGACGCTGCGACCAAA
AAACTGACGCAGGCGCAAAATAATTGCAATCGCTGGACCCGGCTGACCCCGGCTA
TGCACAAGCTGAAGCCGCGGTAGAACAGGCCGGAAAAGAAGCGACGAGGCGAAA
GAGGCCTTAGATAAGGCCACGGATGCGACGGTTAAAGCAGGCACAGACGCCAAAG
CGAAAGCCGAGAAAGCGGATAACATTCTGACCAAATTCCAGGGAACGGCTAATGCC
GCCTCTCAGAATCAGGTTTCCCAGGGTGAGCAGGATAATCTGTCAAATGTCGCCCGC
CTCACTATGCTCATGGCCATGTTTATTGAGATTGTGGGCAAAAATACGGAAGAAAGC
CTGCAAAACGATCTTGCGCTTTTCAACGCCTTGCAGGAAGGGCGTCAGGCGGAGAT
GGAAAAGAAATCGGCTGAATTCCAGGAAGAGACGCGCAAAGCCGAGGAAACGAAC
CGCATTATGGGATGTATCGGGAAAGTCCTCGGCGCGCTGCTAACCATTGTCAGCGTT
GTGGCCGCTGTTTTTACCGGTGGGGCGAGTCTGGCGCTGGCTGCGGTGGGACTTGCG
GTAATGGTGGCCGATGAAATTGTGAAGGCGGCGACGGGAGTGTCGTTTATTCAGCA
GGCGCTAAACCCGATTATGGAGCATGTGCTGAAGCCGTTAATGGAGCTGATTGGCA
AGGCGATTACCAAAGCGCTGGAAGGATTAGGCGTCGATAAGAAAACGGCAGAGAT
GGCCGGCAGCATTGTTGGTGCGATTGTCGCCGCTATTGCCATGGTGGCGGTCATTGT
GGTGGTCGCAGTTGTCGGGAAAGGCGCGGCGGCGAAACTGGGTAACGCGCTGAGCA
AAATGATGGGCGAAACGATTAAGAAGTTGGTGCCTAACGTGCTGAAACAGTTGGCG
CAAAACGGCAGCAAACTCTTTACCCAGGGGATGCAACGTATTACTAGCGGTCTGGG
TAATGTGGGTAGCAAGATGGGCCTGCAAACGAATGCCTTAAGTAAAGAGCTGGTAG
GTAATACCCTAAATAAAGTGGCGTTGGGCATGGAAGTCACGAATACCGCAGCCCAG
TCAGCCGGTGGTGTTGCCGAGGGCGTATTTATTAAAAATGCCAGCGAGGCGCTTGCT
GATTTTATGCTCGCCCGTTTTGCCATGGATCAGATTCAGCAGTGGCTTAAACAATCC
GTAGAAATATTTGGTGAAAACCAGAAGGTAACGGCGGAACTGCAAAAAGCCATGTC
TTCTGCGGTACAGCAAAATGCGGATGCTTCGCGTTTTATTCTGCGCCAGAGTCGCGC
ATAA
```

S1F (SEQ ID NO: 14)

```
MGSSHHHHHHSSGLVPRGSHMLNIQNYSASPHPGIVAERPQTPSASEHVETAVVPST
TEHRGTDIISLSQAATKIHQAQQTLQSTPPISEENNDERTLARQQLTSSLNALAKSGVSLS
AEQNENLRSAFSAPTSALFSASPMAQPRTTISDAEIVVDMVSQNISAIGDSYLGVYENVVA
VYTDFYQAFSDILSKMGGWLLPGKDGNTVKLDVTSLKNDLNSLVNKYNQINSNTVLFP
AQSGSGVKVATEAEARQWLSELNLPNSCLKSYGSGYVVTVDLTPLQKMVQDIDGLGAP
GKDSKLEMDNAKYQAWQSGFKAQEENMKTTLQTLTQKYSNANSLYDNLVKVLSSTISS
SLETAKSFLQGVDMVNDASSISRSGYTQNPRLAEAAFEGVRKNTDFLKAADKAFKDVV
ATKAGDLKAGTKSGESAINTVGLKPPTDAAREKLSSEGQLTLLGKLMTLLGDVSLSQL
ESRLAVWQAMIESQKEMGIQVSKEFQTALGEAQEATDLYEASIKKTDTAKSVYDAATK
KLTQAQNKLQSLDPADPGYAQAEAAVEQAGKEATEAKEALDKATDATVKAGTDAKA
KAEKADNILTKFQGTANAASQNQVSQGEQDNLSNVARLTMLMAMFIEIVGKNTEESLQ
NDLALFNALQEGRQAEMEKKSAEFQEETRKAEETNRIMGCIGKVLGALLTIVSVVAAVF
TGGASLALAAVGLAVMVADEIVKAATGVSFIQQALNPIMEHVLKPLMELIGKAITKALE
GLGVDKKTAEMAGSIVGAIVAAIAMVAVIVVVAVVGKGAAAKLGNALSKMMGETIKK
LVPNVLKQLAQNGSKLFTQGMQRITSGLGNVGSKMGLQTNALSKELVGNTLNKVALG
MEVTNTAAQSAGGVAEGVFIKNASEALADFMLARFAMDQIQQWLKQSVELFGENQKVT
AELQKAMSSAVQQNADASRFILRQSRA
```

S2fusion ((Nde-SseB-Sac-SseC-Bam) in pET15; SEQ ID NO: 15)

```
ATGGGCAGCAGCCATCATCATCATCATCACAGCAGCGGCCTGGTGCCGCGCGGC
AGCCATATGTCTTCAGGAAACATCTTATGGGAAGTCAAAACCCTATTGTGTTTAAA
AATAGCTTCGGCGTCAGCAACGCTGATACCGGGAGCCAGGATGACTTATCCCAGCA
AAATCCGTTTGCCGAAGGGTATGGTGTTTTGCTTATTCTCCTTATGGTTATTCAGGCT
ATCGCAAATAATAAATTTATTGAAGTCCAGAAGAACGCTGAACGTGCCAGAAATAC
CCAGGAAAAGTCAATGAGATGGATGAGGTGATTGCTAAAGCAGCCAAAGGGGAT
GCTAAAACCAAAGAGGAGGTGCCTGAGGATGTAATTAAATACATGCGTGATAATGG
TATTCTCATCGATGGTATGACCATTGATGATTATATGGCTAAATATGGCGATCATGG
GAAGCTGGATAAAGGTGGCCTACAGGCGATCAAAGCGGCTTTGGATAATGACGCCA
ACCGGAATACCGATCTTATGAGTCAGGGGCAGATAACAATTCAAAAAATGTCTCAG
GAGCTTAACGCTGTCCTTACCCAACTGACAGGGCTTATCAGTAAGTGGGGGGAAATT
TCCAGTATGATAGCGCAGAAAACGTACTCACCGCGGATGAATCGAATTCACAGTAA
TAGCGACAGCGCCGCAGGAGTAACCGCCTTAACACATCATCACTTAAGCAATGTCA
GTTGCGTTTCCTCGGGTTCGCTGGAAAGCGCCAGCATCGTGTGAATTCTACTTTTG
GCGATGGCAACGCCGCGTGTCTGCTATCCGGGAAAATTAGTCTTCAGGAGGCAAGC
```

-continued

AATGCGTTGAAGCAACTGCTTGATGCCGTACCCGGAAATCATAAGCGTCCATCATTG
CCTGACTTTTTGCAGACCAATCCCGCGGTTTTATCAATGATGATGACGTCATTAATAC
TCAACGTCTTTGGTAATAACGCTCAATCGTTATGCCAACAGCTTGAGCGGGCAACTG
AGGTGCAAAATGCATTACGTAATAAGCAGGTAAAGGAGTATCAGGAGCAGATCCAG
AAAGCGATAGAGCAGGAGGATAAAGCGCGTAAAGCGGGTATTTTTGGCGCTATTTT
TGACTGGATTACCGGCATATTTGAAACCGTGATTGGCGCCTTAAAAGTTGTGGAAGG
TTTTCTGTCCGGAAATCCCGCAGAAATGGCTAGCGGCGTAGCTTATATGGCCGCAGG
TTGTGCAGGAATGGTTAAAGCCGGAGCCGAAACGGCAATGATGTGCGGTGCTGACC
ACGATACCTGTCAGGCAATTATTGACGTGACAAGTAAGATTCAATTTGGTTGTGAAG
CCGTCGCGCTGGCACTGGATGTTTTCCAGATTGGCCGTGCTTTTATGGCGACGAGAG
GTTTATCTGGCGCAGCTGCAAAAGTGCTTGACTCCGGTTTTGGCGAGGAAGTGGTTG
AGCGTATGGTAGGTGCAGGGGAAGCAGAAATAGAGGAGTTGGCTGAAAAGTTTGGC
GAAGAAGTGAGCGAAAGTTTTTCCAAACAATTTGAGCCGCTTGAACGTGAAATGGC
TATGGCGAATGAGATGGCAGAGGAGGCTGCCGAGTTTTCTCGTAACGTAGAAAATA
ATATGACGCGAAGCGCGGGAAAAAGCTTTACGAAAGAGGGGGTGAAAGCCATGGC
AAAAGAAGCGGCAAAAGAAGCCCTGGAAAAATGTGTGCAAGAAGGTGGAAAGTTC
CTGTTAAAAAAATTCCGTAATAAAGTTCTCTTCAATATGTTCAAAAAAATCCTGTAT
GCCTTACTGAGGGATTGTTCATTTAAAGGCTTACAGGCTATCAGATGTGCAACCGAG
GGCGCCAGTCAGATGAATACTGGCATGGTTAACACAGAAAAAGCGAAGATCGAAAA
GAAAATAGAGCAATTAATAACTCAGCAACGGTTTCTGGATTTCATAATGCAACAAA
CAGAAAACCAGAAAAAGATAGAACAAAAACGCTTAGAGGAGCTTTATAAGGGGAG
CGGTGCCGCGCTTAGAGATGTATTAGATACCATTGATCACTATAGTAGCGTTCAGGC
GAGAATAGCTGGCTATCGCGCTTAA

S2F (SEQ ID NO: 16):

MGSSHHHHHHSSGLVPRGSHMSSGNILWGSQNPIVFKNSFGVSNADTGSQDDLSQQ
NPFAEGYGVLLILLMVIQAIANNKFIEVQKNAERARNTQEKSNEMDEVIAKAAKGDAKT
KEEVPEDVIKYMRDNGILIDGMTIDDYMAKYGDHGKLDKGGLQAIKAALDNDANRNT
DLMSQGQITIQKMSQELNAVLTQLTGLISKWGEISSMIAQKTYSPRMNRIHSNSDSAAGV
TALTHHHLSNVSCVSSGSLGKRQHRVNSTFGDGNAACLLSGKISLQEASNALKQLLDAV
PGNHKRPSLPDFLQTNPAVLSMMMTSLILNVFGNNAQSLCQQLERATEVQNALRNKQV
KEYQEQIQKAIEQEDKARKAGIFGAIFDWITG1FETVIGALKVVEGFLSGNPAEMASGVA
YMAAGCAGMVKAGAETAMMCGADHDTCQAIIDVTSKIQFGCEAVALALDVFQIGRAF
MATRGLSGAAAKVLDSGFGEEVVERMVGAGEAEIEELAEKFGEEVSESFSKQFEPLERE
MAMANEMAEEAAEFSRNVENNMTRSAGKSFTKEGVKAMAKEAAKEALEKCVQEGGK
FLLKKFRNKVLFNMFKKILYALLRDCSFKGLQAIRCATEGASQMNTGMVNTEKAKIEK
KIEQLITQQRFLDFIMQQTENQKKIEQKRLEELYKGSGAALRDVLDTIDHYSSVQARIAG
YRA

*Salmonella typhimurium* pathogenicity island 2, partial sequence (SEQ ID NO: 23):

ATGAATCGAATTCACAGTAATAGCGACAGCGCCGCAGGAGTAACCGCCTTAACACA
TCATCACTTAAGCAATGTCAGTTGCGTTTCCTCGGGTTCGCTGGGAAAGCGCCAGCA
TCGTGTGAATTCTACTTTTGGCGATGGCAACGCCGCGTGTCTGCTATCCGGGAAAAT
TAGTCTTCAGGAGGCAAGCAATGCGTTGAAGCAACTGCTTGATGCCGTACCCGGAA
ATCATAAGCGTCCATCATTGCCTGACTTTTTGCAGACCAATCCCGCGGTTTTATCAAT
GATGATGACGTCATTAATACTCAACGTCTTTGGTAATAACGCTCAATCGTTATGCCA
ACAGCTTGAGCGGGCAACTGAGGTGCAAAATGCATTACGTAATAAGCAGGTAAAGG
AGTATCAGGAGCAGATCCAGAAAGCGATAGAGCAGGAGGATAAAGCGCGTAAAGC
GGGTATTTTTGGCGCTATTTTTGACTGGATTACCGGCATATTTGAAACCGTGATTGGC
GCCTTAAAAGTTGTGGAAGGTTTTCTGTCCGGAAATCCCGCAGAAATGGCTAGCGGC
GTAGCTTATATGGCCGCAGGTTGTGCAGGAATGGTTAAAGCCGGAGCCGAAACGGC
AATGATGTGCGGTGCTGACCACGATACCTGTCAGGCAATTATTGACGTGACAAGTAA
GATTCAATTTGGTTGTGAAGCCGTCGCGCTGGCACTGGATGTTTTCCAGATTGGCCG
TGCTTTTATGGCGACGAGAGGTTTATCTGGCGCAGCTGCAAAAGTGCTTGACTCCGG
TTTTGGCGAGGAAGTGGTTGAGCGTATGGTAGGTGCAGGGGAAGCAGAAATAGAGG
AGTTGGCTGAAAAGTTTGGCGAAGAAGTGAGCGAAAGTTTTTCCAAACAATTTGAG
CCGCTTGAACGTGAAATGGCTATGGCGAATGAGATGGCAGAGGAGGCTGCCGAGTT
TTCTCGTAACGTAGAAAATAATATGACGCGAAGCGCGGGAAAAAGCTTTACGAAAG
AGGGGGTGAAAGCCATGGCAAAAGAAGCGGCAAAAGAAGCCCTGGAAAAATGTGT
GCAAGAAGGTGGAAAGTTCCTGTTAAAAAAATTCCGTAATAAAGTTCTCTTCAATAT
GTTCAAAAAAATCCTGTATGCCTTACTGAGGGATTGTTCATTTAAAGGCTTACAGGC
TATCAGATGTGCAACCGAGGGCGCCAGTCAGATGAATACTGGCATGGTTAACACAG
AAAAAGCGAAGATCGAAAAGAAAATAGAGCAATTAATAACTCAGCAACGGTTTCTG
GATTTCATAATGCAACAAACAGAAAACCAGAAAAAGATAGAACAAAAACGCTTAG
AGGAGCTTTATAAGGGGAGCGGTGCCGCGCTTAGAGATGTATTAGATACCATTGATC
ACTATAGTAGCGTTCAGGCGAGAATAGCTGGCTATCGCGCTTAA

*Salmonella typhimurium* pathogenicity island 2, partial sequence (SEQ ID NO: 24):

M N R I H S N S D S A A G V T A L T H H H L S N V S C V S S G S L G
K R Q H R V N S T F G D G N A A C L L S G K I S L Q E A S N A L K Q
L L D A V P G N H K R P S L P D F L Q T N P A V L S M M M T S L I L
N V F G N N A Q S L C Q Q L E R A T E V Q N A L R N K Q V K E Y Q
E Q I Q K A I E Q E D K A R K A G I F G A I F D W I T G I F E T V I G
A L K V V E G F L S G N P A E M A S G V A Y M A A G C A G M V K A
G A E T A M M C G A D H D T C Q A I I D V T S K I Q F G C E A V A L
A L D V F Q I G R A F M A T R G L S G A A A K V L D S G F G E E V V
E R M V G A G E A E I E E L A E K F G E E V S E S F S K Q F E P L E R
E M A M A N E M A E E A A E F S R N V E N N M T R S A G K S F T K
E G V K A M A K E A A K E A L E K C V Q E G G K F L L K K F R N K

-continued

```
V L F N M F K K I L Y A L L R D C S F K G L Q A I R C A T E G A S Q
M N T G M V N T E K A K I E K K I E Q L I T Q Q R F L D F I M Q Q T
E N Q K K I E Q K R L E E L Y K G S G A A L R D V L D T I D H Y S S
V Q A R I A G Y R A -
```

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed:

1. A method treating a subject infected by a *Salmonella enterica*, comprising administering to the subject a composition comprising *Salmonella* pathogenicity island 1 (SPI-1) protein SipD and *Salmonella* pathogenicity island 2 (SPI-2) protein Sseb; a physiologically acceptable carrier; and, an adjuvant, wherein the composition is administered in an amount so as to elicit an immune response in the subject.

2. A method treating a subject infected by *Salmonella enterica*, comprising administering to the subject a composition comprising *Salmonella* pathogenicity island 2 (SPI-2) protein SseB; a physiologically acceptable carrier; and, an adjuvant, wherein the composition is administered in an amount so as to elicit an immune response in the subject.

* * * * *